US011753481B2

(12) United States Patent
Buatois et al.

(10) Patent No.: US 11,753,481 B2
(45) Date of Patent: Sep. 12, 2023

(54) BISPECIFIC ANTIBODIES AGAINST CEACAM5 AND CD47

(71) Applicant: LamKap Bio Beta AG, Schwyz Pfäffikon (CH)

(72) Inventors: Vanessa Buatois, Contamine-Sarzin (FR); Dirk Hose, Pfäffikon (CH); Anja Seckinger, Lachen (CH)

(73) Assignee: LAMKAP BIO BETA LTD, Schwyz Pfäffikon (CH)

( * ) Notice: Subject to any disclaimer, the term of this patent is extended or adjusted under 35 U.S.C. 154(b) by 0 days.

(21) Appl. No.: 17/554,941

(22) Filed: Dec. 17, 2021

(65) Prior Publication Data

US 2022/0195067 A1   Jun. 23, 2022

Related U.S. Application Data

(60) Provisional application No. 63/135,996, filed on Jan. 11, 2021.

(30) Foreign Application Priority Data

Dec. 18, 2020   (EP) ..................... 20215766

(51) Int. Cl.
C07K 16/46    (2006.01)
C07K 16/30    (2006.01)
A61P 35/00    (2006.01)
C07K 16/28    (2006.01)
A61K 39/00    (2006.01)

(52) U.S. Cl.
CPC .......... *C07K 16/3007* (2013.01); *A61P 35/00* (2018.01); *C07K 16/2803* (2013.01); *A61K 2039/505* (2013.01); *C07K 2317/21* (2013.01); *C07K 2317/31* (2013.01); *C07K 2317/41* (2013.01); *C07K 2317/76* (2013.01); *C07K 2317/92* (2013.01)

(58) Field of Classification Search
CPC .................................................. C07K 16/468
See application file for complete search history.

(56) References Cited

U.S. PATENT DOCUMENTS

| | | | |
|---|---|---|---|
| 6,294,372 | B1 | 9/2001 | Buri et al. |
| 6,946,292 | B2 | 9/2005 | Kanda et al. |
| 7,425,446 | B2 | 9/2008 | Kanda et al. |
| 7,521,051 | B2 | 4/2009 | Collins et al. |
| 8,008,449 | B2 | 8/2011 | Korman et al. |
| 8,067,232 | B2 | 11/2011 | Kanda et al. |
| 8,354,509 | B2 | 1/2013 | Carven et al. |
| 8,383,796 | B2 | 2/2013 | Korman et al. |
| 8,642,292 | B2 | 2/2014 | Sandig et al. |
| 2005/0147614 | A1 | 7/2005 | Begent et al. |
| 2011/0064653 | A1 | 3/2011 | Hansen et al. |
| 2012/0184716 | A1 | 7/2012 | Fischer et al. |
| 2014/0242079 | A1 | 8/2014 | Bacac et al. |
| 2014/0242080 | A1 | 8/2014 | Jaeger et al. |

FOREIGN PATENT DOCUMENTS

| | | |
|---|---|---|
| EP | 2282773 B1 | 1/2014 |
| EP | 2681244 B1 | 11/2017 |
| EP | 3623388 A1 | 3/2020 |
| EP | 3831849 A1 | 6/2021 |
| WO | WO-2003099196 A2 | 12/2003 |
| WO | WO-2004063351 A2 | 7/2004 |
| WO | WO-2004099249 A2 | 11/2004 |
| WO | WO-2005018572 A2 | 3/2005 |
| WO | WO-2005018669 A1 | 3/2005 |
| WO | WO-2005056759 A2 | 6/2005 |
| WO | WO-2005063815 A2 | 7/2005 |
| WO | WO-2005092925 A2 | 10/2005 |
| WO | WO-2005110474 A2 | 11/2005 |
| WO | WO-2006019447 A1 | 2/2006 |
| WO | WO-2006023420 A2 | 3/2006 |
| WO | WO-2006047350 A2 | 5/2006 |
| WO | WO-2006085967 A2 | 8/2006 |
| WO | WO-2006105338 A2 | 10/2006 |
| WO | WO-2006116260 A2 | 11/2006 |
| WO | WO-2007005874 A2 | 1/2007 |
| WO | WO-2007008943 A2 | 1/2007 |
| WO | WO-2007021841 A2 | 2/2007 |
| WO | WO-2007024249 A2 | 3/2007 |
| WO | WO-2007041635 A2 | 4/2007 |
| WO | WO-2007044616 A2 | 4/2007 |
| WO | WO-2007048077 A2 | 4/2007 |

(Continued)

OTHER PUBLICATIONS

Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Harris (Biotechnology, vol. 11, p. 1293-1297, 1993) (Year: 1993).*
Colman P. M. (Research in Immunology, 145:33-36, 1994) (Year: 1994).*
Kearns (Molecular Cancer Therapeutics, vol. 14, No. 7, p. 1625-1636, 2015) (Year: 2015).*
Rudikoff et al. (Proceedings of the National Academy of Sciences USA, vol. 79, p. 1979-1983, 1982) (Year: 1982).*
Bacac, M., et al., "A Novel Carcinoembryonic Antigen T-Cell Bispecific Antibody (CEA TCB) for the Treatment of Solid Tumors," Clin. Cancer Res., 22(13):3286-3297, American Association for Cancer Research, United States (2016)).

(Continued)

*Primary Examiner* — Michael Allen
(74) *Attorney, Agent, or Firm* — STERNE, KESSLER, GOLDSTEIN & FOX P.L.L.C.

(57) ABSTRACT

The present invention relates to bispecific antibodies which bind to human carcinoembryonic antigen CEACAM5 and human CD47. In addition, the present invention relates to polynucleotides encoding such bispecific antibodies and vectors and host cells comprising such polynucleotides. The invention further relates to methods for selecting and producing such antibodies and to methods of using such antibodies in the treatment of diseases. The invention also relates to the therapeutic use of the bispecific antibodies in monotherapy and in combination therapy.

10 Claims, 10 Drawing Sheets

Specification includes a Sequence Listing.

(56) References Cited

FOREIGN PATENT DOCUMENTS

| | | |
|---|---|---|
| WO | WO-2007071426 A1 | 6/2007 |
| WO | WO-2007106707 A2 | 9/2007 |
| WO | WO-2008022152 A2 | 2/2008 |
| WO | WO-2008036688 A2 | 3/2008 |
| WO | WO-2008091798 A2 | 7/2008 |
| WO | WO-2008091954 A2 | 7/2008 |
| WO | WO-2008092117 A2 | 7/2008 |
| WO | WO-2008098115 A2 | 8/2008 |
| WO | WO-2008121160 A2 | 10/2008 |
| WO | WO-2008140603 A2 | 11/2008 |
| WO | WO-2008150494 A1 | 12/2008 |
| WO | WO-2008156712 A1 | 12/2008 |
| WO | WO-2009101611 A1 | 8/2009 |
| WO | WO-2009114335 A2 | 9/2009 |
| WO | WO-2010027423 A1 | 3/2010 |
| WO | WO-2010027827 A2 | 3/2010 |
| WO | WO-2010027828 A2 | 3/2010 |
| WO | WO-2010033736 A1 | 3/2010 |
| WO | WO-2010077634 A1 | 7/2010 |
| WO | WO-2012023053 A2 | 2/2012 |
| WO | WO-2013012414 A1 | 1/2013 |
| WO | WO-2013019906 A1 | 2/2013 |
| WO | WO-2013088259 A2 | 6/2013 |
| WO | WO-2013173223 A1 | 11/2013 |
| WO | WO-2014087248 A2 | 6/2014 |
| WO | WO-2014113510 A1 | 7/2014 |
| WO | WO-2015026634 A1 | 2/2015 |
| WO | WO-2015112534 A2 | 7/2015 |
| WO | WO-2016007235 A1 | 1/2016 |
| WO | WO-2016156537 A1 | 10/2016 |
| WO | WO-2017055389 A1 | 4/2017 |
| WO | WO-2017118657 A1 | 7/2017 |
| WO | WO-2017118675 A1 | 7/2017 |
| WO | WO-2017196793 A1 | 11/2017 |
| WO | WO-2018057955 A1 | 3/2018 |
| WO | WO-2018098384 A1 | 5/2018 |
| WO | WO-2019016411 A1 | 1/2019 |
| WO | WO-2019234576 A1 | 12/2019 |
| WO | WO-2022130348 A1 | 6/2022 |

OTHER PUBLICATIONS

Beauchemin, N., and Arabzadeh, A., "Carcinoembryonic antigen-related cell adhesion molecules (CEACAMs) in cancer progression and metastasis," Cancer Metastasis Rev. 32(3-4):643-671, Springer Science+Business Media, Germany (2013).
Berinstein, N.L.,"Carcinoembryonic antigen as a target for therapeutic anticancer vaccines: a review," J. Clin. Oncol. 20(8):2197-2207, American Society of Clinical Oncology, United States (2002).
ClinicalTrials.gov, "A Study of RO7172508 in Patients With Locally Advanced and/or Metastatic CEA-Positive Solid Tumors," Clinical Trial Identifier: NCT03539484, accessed at https://clinicaltrials.gov/ct2/show/NCT03539484, accessed on Jul. 26, 2022, 10 pages.
ClinicalTrials.gov, "A Phase Ib Study to Evaluate the Safety, Efficacy, and Pharmacokinetics of Cibisatamab in Combination With Atezolizumab After Pretreatment With Obinutuzumab in Participants With Previously Treated Metastatic Colorectal Adenocarcinoma," Clinical Trial Identifier: NCT03866239, accessed at https://clinicaltrials.gov/ct2/show/NCT03866239, accessed on Jul. 26, 2022, 11 pages.
ClinicalTrials.gov, "Study to Evaluate Safety, Pharmacokinetics, Pharmacodynamics, and Preliminary Anti-Tumor Activity of RO7122290 in Combination With Cibisatamab With Obinutuzumab Pre-Treatment," Clinical Trial Identifier: NCT04826003, accessed at https://clinicaltrials.gov/ct2/show/NCT048260Q3, accessed on Jul. 26, 2022, 22 pages.
Dheilly, E., et al., "Selective Blockade of the Ubiquitous Checkpoint Receptor CD47 Is Enabled by Dual-Targeting Bispecific Antibodies," Mol. Ther. 25(2):523-533, Cell Press, United States (2017).

Gold, P. and Freedman, S.O., "Demonstration of Tumor-Specific Antigens in Human Colonic Carcinomata by Immunological Tolerance and Absorption Techniques," J Exp. Med. 121(3):439-462, Rockefeller University Press, United States (1965).
Greenbaum, U., et al., "Chimeric Antigen Receptor Therapy: How Are We Driving in Solid Tumors?" Biol. Blood Marrow Transplant 26(10): 1759-1769, Elsevier, Netherlands (2020).
Hammarstrom, S., "The carcinoembryonic antigen (CEA) family: structures, suggested functions and expression in normal and malignant tissues," Semin. Cancer Biol. 9(2):67-81, Academic Press, United States (1999).
Hayashi, H., et al., "Molecular cloning of mouse alpha-1,6-fucosyltransferase and expression of its mRNA in the developing cerebrum," DNA Seq. 11(1-2):91-96, Taylor & Francis, United Kingdom (2000).
Huang, Y., et al., "Targeting CD47: the achievements and concerns of current studies on cancer immunotherapy," J. Thorac. Dis. 9(2):E168-E174, AME Publishing Company, Hong Kong (2017).
International Search Report and Written Opinion for International Application No. PCT/IB2021/061983, European Patent Office, Netherlands, dated Oct. 5, 2022, 11 pages.
Johnson, G., and Wu, T.T., "Kabat database and its applications: 30 years after the first variability plot," Nucleic Acids Res. 28:214-218, Oxford University Press, United Kingdom (2000).
Kabat, E.A., et al., "Evolutionary and structural influences on light chain constant (CL) region of human and mouse immunoglobulins," Proc. Natl. Acad. Sci. USA 72(7):2785-2788, National Academy of Sciences, United States (1975).
Kabat, E.A., et al., Sequences of Proteins of Immunological Interest, 5th Ed. Public Health Service, National Institutes of Health, Bethesda, MD (1991).
Kaur, S., et al., "Preclinical and Clinical Development of Therapeutic Antibodies Targeting Functions of CD47 in the Tumor Microenvironment," Antib. Ther. 3(3):179-192, Oxford Academic, United Kingdom (2020).
Kuespert, K., et al., "CEACAMs: their role in physiology and pathophysiology," Curr. Opin. Cell Biol. 18(5):565-571, Elsevier, Netherlands (2006).
Kuroki, M., et al., "Molecular cloning of nonspecific cross-reacting antigens in human granulocytes," J. Biol. Chem. 266(18):11810-11817, American Society for Biochemistry and Molecular Biology, United States (1991).
Melero, I., et al., "Pharmacokinetics (PK) and pharmacodynamics (PD) of a novel carcinoembryonic antigen (CEA) T-cell bispecific antibody (CEA CD3 TCB) for the treatment of CEA-expressing solid tumors," 2017 ASCO Annual Meeting, Abstract 2549 and Poster No. 41, J. Clin Oncol. 35(15S): Abstract 2549, United States (May 20, 2017). Accessed at https://meetinglibrary.asco.org/record/148867/abstract on Jul. 26, 2022.
Niwa, R., et al., "Defucosylated chimeric anti-CC chemokine receptor 4 IgG1 with enhanced antibody-dependent cellular cytotoxicity shows potent therapeutic activity to T-cell leukemia and lymphoma," Cancer Res. 64(6):2127-33, American Association for Cancer Research, United States (2004).
Oberst, M.D., et al., "CEA/CD3 bispecific antibody MEDI-565/AMG 211 activation of T cells and subsequent killing of human tumors is independent of mutations commonly found in colorectal adenocarcinomas," MAbs. 6(6):1571-1584, Taylor & Francis, United Kingdom (2014).
Piccione, E.C., et al., "A bispecific antibody targeting CD47 and CD20 selectively binds and eliminates dual antigen expressing lymphoma cells," MAbs. 7(5):946-956, Taylor & Francis, United Kingdom (2015).
Pils, S., et al., "CEACAM3: an innate immune receptor directed against human-restricted bacterial pathogens," Int. J. Med. Microbiol. 298(7-8):553-560, Elsevier, Netherlands (2008).
Pishvaian, M., et al., "Phase 1 Dose Escalation Study of MEDI-565, a Bispecific T-Cell Engager that Targets Human Carcinoembryonic Antigen, in Patients With Advanced Gastrointestinal Adenocarcinomas," Clin. Colorectal Cancer 15(4):345-351, Elsevier, Netherlands (2016).
Ramirez-Solis, R., et al., "Genomic DNA microextraction: a method to screen numerous samples," Anal. Biochem. 201(2):331-335, Elsevier, Netherlands (1992).

(56) References Cited

OTHER PUBLICATIONS

Rillahan, C.D., et al., "Global metabolic inhibitors of sialyl- and fucosyltransferases remodel the glycome," Nat. Chem. Biol. 8(7):661-668, Nature Portfolio, Germany (2012).

Schmitter, T., et al., "Granulocyte CEACAM3 is a phagocytic receptor of the innate immune system that mediates recognition and elimination of human-specific pathogens," J. Exp. Med. 199(1):35-46, Rockefeller University Press, United States (2004).

Sonnichsen, R., et al., "Individual Susceptibility Analysis Using Patient-derived Slice Cultures of Colorectal Carcinoma," Clin. Colorectal Cancer 17(2):e189-e199, Elsevier, Netherlands (2018).

Tabernero, J., et al., "Phase Ia and Ib studies of the novel carcinoembryonic antigen (CEA) T-cell bispecific (CEA CD3 TCB) antibody as a single agent and in combination with atezolizumab: Preliminary efficacy and safety in patients with metastatic colorectal cancer (mCRC)," J. Clin. Oncol. 35(15S): Abstract 3002, United States (2017).

Van Bommel, P.E., et al., "CD20-selective inhibition of CD47-SIRPα "don't eat me" signaling with a bispecific antibody-derivative enhances the anticancer activity of daratumumab, alemtuzumab and obinutuzumab," Oncoimmunol. 7(2):e1386361, Taylor & Francis, United Kingdom (2018).

Weiskopf, K., et al., "Cancer immunotherapy targeting the CD47/SIRPα axis," Eur. J. Cancer. 76:100-109, Elsevier, Netherlands (2017).

Xu, J., et al., "Chimeric antigen receptor-T cell therapy for solid tumors require new clinical regimens," Expert Rev. Anticancer Ther. 17(12):1099-1106, Informa, United Kingdom (2017).

Yamane-Ohnuki, N., et al., "Establishment of FUT8 knockout Chinese hamster ovary cells: an ideal host cell line for producing completely defucosylated antibodies with enhanced antibodydependent cellular cytotoxicity," Biotechnol. Bioeng. 87(5):614-622, Wiley, United States (2004).

\* cited by examiner

```
                        SEQUENCE LISTING

<160> NUMBER OF SEQ ID NOS: 50

<210> SEQ ID NO 1
<211> LENGTH: 5
<212> TYPE: PRT
<213> ORGANISM: Artificial Sequence
<220> FEATURE:
<223> OTHER INFORMATION: Common heavy chain CDRH1

<400> SEQUENCE: 1

Ser Tyr Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Common heavy chain CDRH2

<400> SEQUENCE: 2

Ala Ile Ser Gly Ser Gly Gly Ser Thr Tyr Tyr Ala Asp Ser Val Lys
1               5                   10                  15

Gly

<210> SEQ ID NO 3
<211> LENGTH: 7
<212> TYPE: PRT
<213> ORGANISM: Artificial Sequence
<220> FEATURE:
<223> OTHER INFORMATION: Common heavy chain CDRH3

<400> SEQUENCE: 3

Ser Tyr Gly Ala Phe Asp Tyr
1               5

<210> SEQ ID NO 4
<211> LENGTH: 116
<212> TYPE: PRT
<213> ORGANISM: Artificial Sequence
<220> FEATURE:
<223> OTHER INFORMATION: Common heavy chain VH

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Lys Ser Tyr Gly Ala Phe Asp Tyr Trp Gly Gln Gly Thr Leu Val
                100                 105                 110

Thr Val Ser Ser
        115

<210> SEQ ID NO 5
<211> LENGTH: 229
<212> TYPE: PRT
<213> ORGANISM: Artificial Sequence
<220> FEATURE:
<223> OTHER INFORMATION: Common heavy chain (VH-CH1)

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Lys Ser Tyr Gly Ala Phe Asp Tyr Trp Gly Gln Gly Thr Leu Val
                100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro
225

<210> SEQ ID NO 6
<211> LENGTH: 445
<212> TYPE: PRT
<213> ORGANISM: Artificial Sequence
<220> FEATURE:
<223> OTHER INFORMATION: common heavy chain (VH-CH1-CH2-CH3)

<400> SEQUENCE: 6

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly

<210> SEQ ID NO 7
<211> LENGTH: 11
<212> TYPE: PRT
<213> ORGANISM: Artificial Sequence
<220> FEATURE:
<223> OTHER INFORMATION: CD47 binding part CDRL1

<400> SEQUENCE: 7

```
Arg Ala Ser Gln Ser Ile Ser Ser Tyr Leu Asn
1               5                   10
```

<210> SEQ ID NO 8
<211> LENGTH: 7
<212> TYPE: PRT
<213> ORGANISM: Artificial Sequence
<220> FEATURE:
<223> OTHER INFORMATION: CD47 binding part CDRL2

<400> SEQUENCE: 8

```
Ala Ala Ser Ser Leu Gln Ser
1               5
```

<210> SEQ ID NO 9
<211> LENGTH: 10
<212> TYPE: PRT
<213> ORGANISM: Artificial Sequence
<220> FEATURE:
<223> OTHER INFORMATION: CD47 binding part CDRL3

<400> SEQUENCE: 9

```
Gln Gln Met His Pro Arg Ala Pro Lys Thr
1               5                   10
```

<210> SEQ ID NO 10
<211> LENGTH: 108
<212> TYPE: PRT
<213> ORGANISM: Artificial Sequence
<220> FEATURE:
<223> OTHER INFORMATION: CD47 binding part VK

<400> SEQUENCE: 10

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
                20                  25                  30
Leu Asn Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Met His Pro Arg Ala Pro
                85                  90                  95
Lys Thr Phe Gly Gln Gly Thr Lys Val Glu Ile Lys
            100                 105
```

<210> SEQ ID NO 11
<211> LENGTH: 215
<212> TYPE: PRT
<213> ORGANISM: Artificial Sequence
<220> FEATURE:
<223> OTHER INFORMATION: CD47 binding part light chain (VKCK; K2)

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 12
<211> LENGTH: 648
<212> TYPE: DNA
<213> ORGANISM: Artificial Sequence
<220> FEATURE:
<223> OTHER INFORMATION: CD47 binding part light chain (VKCK; nucleic
      acid); (K2)

<400> SEQUENCE: 12
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag atgcacccgc gcgccccgaa gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttaa                 648

```
<210> SEQ ID NO 13
<211> LENGTH: 107
<212> TYPE: PRT
<213> ORGANISM: Artificial Sequence
<220> FEATURE:
<223> OTHER INFORMATION: CD47 binding part constant light chain kappa
      (CK)

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 14
<211> LENGTH: 13
<212> TYPE: PRT
<213> ORGANISM: Artificial Sequence
<220> FEATURE:
<223> OTHER INFORMATION: CEACAM5 binding part AC82 CDRL1;

<400> SEQUENCE: 14

Ser Gly Ser Ser Ser Asn Ile Gly Tyr Gly Leu Val Ser
1               5                   10

<210> SEQ ID NO 15
<211> LENGTH: 7
<212> TYPE: PRT
<213> ORGANISM: Artificial Sequence
<220> FEATURE:
<223> OTHER INFORMATION: CEACAM5 binding part AC82 CDRL2

<400> SEQUENCE: 15

Gly Ile Asn Lys Arg Pro Ser
1               5

<210> SEQ ID NO 16
<211> LENGTH: 10
<212> TYPE: PRT
<213> ORGANISM: Artificial Sequence
<220> FEATURE:
<223> OTHER INFORMATION: CEACAM5 binding part AC82 CDRL3

<400> SEQUENCE: 16

Gly Thr Trp Asp Phe Ser Tyr Arg Val Asp
1               5                   10

<210> SEQ ID NO 17
<211> LENGTH: 13
<212> TYPE: PRT
<213> ORGANISM: Artificial Sequence
<220> FEATURE:
<223> OTHER INFORMATION: CEACAM5 binding part AC84 CDRL1

<400> SEQUENCE: 17
```

Ser Gly Ser Ser Ser Asn Ile Gly Ile Gly Leu Val Ser
1               5                   10

<210> SEQ ID NO 18
<211> LENGTH: 7
<212> TYPE: PRT
<213> ORGANISM: Artificial Sequence
<220> FEATURE:
<223> OTHER INFORMATION: CEACAM5 binding part AC84 CDRL2

<400> SEQUENCE: 18

Asn Val Asn Thr Arg Pro Ser
1               5

<210> SEQ ID NO 19
<211> LENGTH: 10
<212> TYPE: PRT
<213> ORGANISM: Artificial Sequence
<220> FEATURE:
<223> OTHER INFORMATION: CEACAM5 binding part AC84 CDRL3

<400> SEQUENCE: 19

Gly Thr Trp Asp Phe Ser Tyr Arg Val Asp
1               5                   10

<210> SEQ ID NO 20
<211> LENGTH: 13
<212> TYPE: PRT
<213> ORGANISM: Artificial Sequence
<220> FEATURE:
<223> OTHER INFORMATION: CEACAM5 binding part AC91 CDRL1

<400> SEQUENCE: 20

Ser Gly Ser Ser Ser Asn Ile Gly Ile Gly Leu Val Ser
1               5                   10

<210> SEQ ID NO 21
<211> LENGTH: 7
<212> TYPE: PRT
<213> ORGANISM: Artificial Sequence
<220> FEATURE:
<223> OTHER INFORMATION: CEACAM5 binding part AC91 CDRL2

<400> SEQUENCE: 21

Thr Val Asn Asn Arg Pro Ser
1               5

<210> SEQ ID NO 22
<211> LENGTH: 10
<212> TYPE: PRT
<213> ORGANISM: Artificial Sequence
<220> FEATURE:
<223> OTHER INFORMATION: CEACAM5 binding part AC91 CDRL3

<400> SEQUENCE: 22

Gly Thr Phe Asp Phe Ser Tyr Gly Ile Val
1               5                   10

<210> SEQ ID NO 23
<211> LENGTH: 13
<212> TYPE: PRT
<213> ORGANISM: Artificial Sequence
<220> FEATURE:
<223> OTHER INFORMATION: CEACAM5 binding part AC100 CDRL1

<400> SEQUENCE: 23

```
Ser Gly Ser Ser Ser Asn Ile Gly Tyr Gly Leu Val Ser
1               5                   10

<210> SEQ ID NO 24
<211> LENGTH: 7
<212> TYPE: PRT
<213> ORGANISM: Artificial Sequence
<220> FEATURE:
<223> OTHER INFORMATION: CEACAM5 binding part AC100 CDRL2

<400> SEQUENCE: 24

Asn Gly Asn Ile Arg Pro Ser
1               5

<210> SEQ ID NO 25
<211> LENGTH: 10
<212> TYPE: PRT
<213> ORGANISM: Artificial Sequence
<220> FEATURE:
<223> OTHER INFORMATION: CEACAM5 binding part AC100 CDRL3

<400> SEQUENCE: 25

Gly Thr Trp Asp Phe Ser Tyr Arg Val Asp
1               5                   10

<210> SEQ ID NO 26
<211> LENGTH: 13
<212> TYPE: PRT
<213> ORGANISM: Artificial Sequence
<220> FEATURE:
<223> OTHER INFORMATION: CEACAM5 binding part AC117 CDRL1

<400> SEQUENCE: 26

Ser Gly Ser Ser Ser Asn Ile Gly Ile Gly Leu Val Ser
1               5                   10

<210> SEQ ID NO 27
<211> LENGTH: 7
<212> TYPE: PRT
<213> ORGANISM: Artificial Sequence
<220> FEATURE:
<223> OTHER INFORMATION: CEACAM5 binding part AC117 CDRL2

<400> SEQUENCE: 27

Asn Gly Asn Val Arg Pro Ser
1               5

<210> SEQ ID NO 28
<211> LENGTH: 10
<212> TYPE: PRT
<213> ORGANISM: Artificial Sequence
<220> FEATURE:
<223> OTHER INFORMATION: CEACAM5 binding part AC117 CDRL3

<400> SEQUENCE: 28

Gly Thr Trp Asp Phe Ser Tyr Arg Val Asp
1               5                   10

<210> SEQ ID NO 29
<211> LENGTH: 13
<212> TYPE: PRT
<213> ORGANISM: Artificial Sequence
<220> FEATURE:
<223> OTHER INFORMATION: CEACAM5 binding part AC22 CDRL1

<400> SEQUENCE: 29

Ser Gly Ser Ser Ser Asn Ile Ala Asn Gly Ile Val Ser
```

<210> SEQ ID NO 30
<211> LENGTH: 7
<212> TYPE: PRT
<213> ORGANISM: Artificial Sequence
<220> FEATURE:
<223> OTHER INFORMATION: CEACAM5 binding part AC22 CDRL2

<400> SEQUENCE: 30

Phe Asp Asn Leu Arg Pro Ser
1               5

<210> SEQ ID NO 31
<211> LENGTH: 10
<212> TYPE: PRT
<213> ORGANISM: Artificial Sequence
<220> FEATURE:
<223> OTHER INFORMATION: CEACAM5 binding part AC22 CDRL3

<400> SEQUENCE: 31

Gly Thr Trp Asp Phe Ser Tyr Gly Ile Val
1               5                   10

<210> SEQ ID NO 32
<211> LENGTH: 109
<212> TYPE: PRT
<213> ORGANISM: Artificial Sequence
<220> FEATURE:
<223> OTHER INFORMATION: CEACAM5 binding part AC82 VL

<400> SEQUENCE: 32

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Tyr Gly
            20                  25                  30

Leu Val Ser Trp Tyr Gln Gln Leu Pro Gly Thr Ala Pro Lys Leu Leu
        35                  40                  45

Ile Tyr Gly Ile Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Phe Ser Tyr
                85                  90                  95

Arg Val Asp Phe Gly Gly Gly Thr Lys Leu Thr Val Leu
            100                 105

<210> SEQ ID NO 33
<211> LENGTH: 109
<212> TYPE: PRT
<213> ORGANISM: Artificial Sequence
<220> FEATURE:
<223> OTHER INFORMATION: CEACAM5 binding part AC84 VL

<400> SEQUENCE: 33

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Ile Gly
            20                  25                  30

Leu Val Ser Trp Tyr Gln Gln Leu Pro Gly Thr Ala Pro Lys Leu Leu
        35                  40                  45

Ile Tyr Asn Val Asn Thr Arg Pro Ser Gly Ile Pro Asp Arg Phe Ser

```
                 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Phe Ser Tyr
                 85                  90                  95

Arg Val Asp Phe Gly Gly Gly Thr Lys Leu Thr Val Leu
                100                 105
```

<210> SEQ ID NO 34
<211> LENGTH: 109
<212> TYPE: PRT
<213> ORGANISM: Artificial Sequence
<220> FEATURE:
<223> OTHER INFORMATION: CEACAM5 binding part AC91 VL

<400> SEQUENCE: 34

```
Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Ile Gly
                 20                  25                  30

Leu Val Ser Trp Tyr Gln Gln Leu Pro Gly Thr Ala Pro Lys Leu Leu
             35                  40                  45

Ile Tyr Thr Val Asn Asn Arg Pro Ser Gly Ile Pro Asp Arg Phe Ser
     50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Phe Asp Phe Ser Tyr
                 85                  90                  95

Gly Ile Val Phe Gly Gly Gly Thr Lys Leu Thr Val Leu
                100                 105
```

<210> SEQ ID NO 35
<211> LENGTH: 109
<212> TYPE: PRT
<213> ORGANISM: Artificial Sequence
<220> FEATURE:
<223> OTHER INFORMATION: CEACAM5 binding part AC100 VL

<400> SEQUENCE: 35

```
Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Tyr Gly
                 20                  25                  30

Leu Val Ser Trp Tyr Gln Gln Leu Pro Gly Thr Ala Pro Lys Leu Leu
             35                  40                  45

Ile Tyr Asn Gly Asn Ile Arg Pro Ser Gly Ile Pro Asp Arg Phe Ser
     50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Phe Ser Tyr
                 85                  90                  95

Arg Val Asp Phe Gly Gly Gly Thr Lys Leu Thr Val Leu
                100                 105
```

<210> SEQ ID NO 36
<211> LENGTH: 109
<212> TYPE: PRT
<213> ORGANISM: Artificial Sequence
<220> FEATURE:

<223> OTHER INFORMATION: CEACAM5 binding part AC117 VL

<400> SEQUENCE: 36

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Ile Gly
                20                  25                  30

Leu Val Ser Trp Tyr Gln Gln Leu Pro Gly Thr Ala Pro Lys Leu Leu
            35                  40                  45

Ile Tyr Asn Gly Asn Val Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Phe Ser Tyr
                85                  90                  95

Arg Val Asp Phe Gly Gly Gly Thr Lys Leu Thr Val Leu
                100                 105

<210> SEQ ID NO 37
<211> LENGTH: 215
<212> TYPE: PRT
<213> ORGANISM: Artificial Sequence
<220> FEATURE:
<223> OTHER INFORMATION: CEACAM5 binding part AC82 VLCL

<400> SEQUENCE: 37

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Tyr Gly
                20                  25                  30

Leu Val Ser Trp Tyr Gln Gln Leu Pro Gly Thr Ala Pro Lys Leu Leu
            35                  40                  45

Ile Tyr Gly Ile Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Phe Ser Tyr
                85                  90                  95

Arg Val Asp Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 38

```
<211> LENGTH: 215
<212> TYPE: PRT
<213> ORGANISM: Artificial Sequence
<220> FEATURE:
<223> OTHER INFORMATION: CEACAM5 binding part AC84 VLCL

<400> SEQUENCE: 38

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Ile Gly
            20                  25                  30

Leu Val Ser Trp Tyr Gln Gln Leu Pro Gly Thr Ala Pro Lys Leu Leu
        35                  40                  45

Ile Tyr Asn Val Asn Thr Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Phe Ser Tyr
                85                  90                  95

Arg Val Asp Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 39
<211> LENGTH: 215
<212> TYPE: PRT
<213> ORGANISM: Artificial Sequence
<220> FEATURE:
<223> OTHER INFORMATION: CEACAM5 binding part AC91 VLCL

<400> SEQUENCE: 39

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Ile Gly
            20                  25                  30

Leu Val Ser Trp Tyr Gln Gln Leu Pro Gly Thr Ala Pro Lys Leu Leu
        35                  40                  45

Ile Tyr Thr Val Asn Asn Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Phe Asp Phe Ser Tyr
                85                  90                  95

Gly Ile Val Phe Gly Gly Gly Thr Lys Leu Thr Val Leu Gly Gln Pro
```

```
                    100                 105                 110
Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 40
<211> LENGTH: 215
<212> TYPE: PRT
<213> ORGANISM: Artificial Sequence
<220> FEATURE:
<223> OTHER INFORMATION: CEACAM5 binding part AC100 VLCL

<400> SEQUENCE: 40

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Tyr Gly
            20                  25                  30

Leu Val Ser Trp Tyr Gln Gln Leu Pro Gly Thr Ala Pro Lys Leu Leu
        35                  40                  45

Ile Tyr Asn Gly Asn Ile Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Phe Ser Tyr
                85                  90                  95

Arg Val Asp Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 41
<211> LENGTH: 215
<212> TYPE: PRT
```

```
<213> ORGANISM: Artificial Sequence
<220> FEATURE:
<223> OTHER INFORMATION: CEACAM5 binding part AC117 VLCL

<400> SEQUENCE: 41

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Ile Gly
            20                  25                  30

Leu Val Ser Trp Tyr Gln Gln Leu Pro Gly Thr Ala Pro Lys Leu Leu
        35                  40                  45

Ile Tyr Asn Gly Asn Val Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Phe Ser Tyr
                85                  90                  95

Arg Val Asp Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 42
<211> LENGTH: 215
<212> TYPE: PRT
<213> ORGANISM: Artificial Sequence
<220> FEATURE:
<223> OTHER INFORMATION: CEACAM5 binding part AC22 VLCL

<400> SEQUENCE: 42

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Ala Asn Gly
            20                  25                  30

Ile Val Ser Trp Tyr Gln Gln Leu Pro Gly Thr Ala Pro Lys Leu Leu
        35                  40                  45

Ile Tyr Phe Asp Asn Leu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Phe Ser Tyr
                85                  90                  95

Gly Ile Val Phe Gly Gly Gly Thr Lys Leu Thr Val Leu Gly Gln Pro
            100                 105                 110
```

```
Lys Ala Ala Pro Ser Val Thr Leu Phe Pro Ser Ser Glu Glu Leu
            115                 120                 125
Gln Ala Asn Lys Ala Thr Leu Val Cys Leu Ile Ser Asp Phe Tyr Pro
        130                 135                 140
Gly Ala Val Thr Val Ala Trp Lys Ala Asp Ser Ser Pro Val Lys Ala
145                 150                 155                 160
Gly Val Glu Thr Thr Thr Pro Ser Lys Gln Ser Asn Asn Lys Tyr Ala
            165                 170                 175
Ala Ser Ser Tyr Leu Ser Leu Thr Pro Glu Gln Trp Lys Ser His Arg
            180                 185                 190
Ser Tyr Ser Cys Gln Val Thr His Glu Gly Ser Thr Val Glu Lys Thr
            195                 200                 205
Val Ala Pro Thr Glu Cys Ser
            210                 215

<210> SEQ ID NO 43
<211> LENGTH: 106
<212> TYPE: PRT
<213> ORGANISM: Artificial Sequence
<220> FEATURE:
<223> OTHER INFORMATION: VK_SM3E

<400> SEQUENCE: 43

Glu Asn Val Leu Thr Gln Ser Pro Ser Ser Met Ser Val Ser Val Gly
1               5                   10                  15
Asp Arg Val Asn Ile Ala Cys Ser Ala Ser Ser Ser Val Pro Tyr Met
            20                  25                  30
His Trp Leu Gln Gln Lys Pro Gly Lys Ser Pro Lys Leu Leu Ile Tyr
        35                  40                  45
Leu Thr Ser Asn Leu Ala Ser Gly Val Pro Ser Arg Phe Ser Gly Ser
    50                  55                  60
Gly Ser Gly Thr Asp Tyr Ser Leu Thr Ile Ser Ser Val Gln Pro Glu
65                  70                  75                  80
Asp Ala Ala Thr Tyr Tyr Cys Gln Gln Arg Ser Ser Tyr Pro Leu Thr
            85                  90                  95
Phe Gly Gly Gly Thr Lys Leu Glu Ile Lys
            100                 105

<210> SEQ ID NO 44
<211> LENGTH: 120
<212> TYPE: PRT
<213> ORGANISM: Artificial Sequence
<220> FEATURE:
<223> OTHER INFORMATION: VH_SM3E

<400> SEQUENCE: 44

Gln Val Lys Leu Glu Gln Ser Gly Ala Glu Val Val Lys Pro Gly Ala
1               5                   10                  15
Ser Val Lys Leu Ser Cys Lys Ala Ser Gly Phe Asn Ile Lys Asp Ser
            20                  25                  30
Tyr Met His Trp Leu Arg Gln Gly Pro Gly Gln Arg Leu Glu Trp Ile
        35                  40                  45
Gly Trp Ile Asp Pro Glu Asn Gly Asp Thr Glu Tyr Ala Pro Lys Phe
    50                  55                  60
Gln Gly Lys Ala Thr Phe Thr Thr Asp Thr Ser Ala Asn Thr Ala Tyr
65                  70                  75                  80
Leu Gly Leu Ser Ser Leu Arg Pro Glu Asp Thr Ala Val Tyr Tyr Cys
            85                  90                  95
```

Asn Glu Gly Thr Pro Thr Gly Pro Tyr Tyr Phe Asp Tyr Trp Gly Gln
            100                 105                 110

Gly Thr Leu Val Thr Val Ser Ser
        115                 120

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
gtctgaagca ttatgtgttg aagc                                      24

<210> SEQ ID NO 46
<211> LENGTH: 23
<212> TYPE: DNA
<213> ORGANISM: Artificial Sequence
<220> FEATURE:
<223> OTHER INFORMATION: Primer

<400> SEQUENCE: 46
gtgagtacat tcattgtact gtg                                       23

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
ttgtgtgact cttaactctc agag                                      24

<210> SEQ ID NO 48
<211> LENGTH: 25
<212> TYPE: DNA
<213> ORGANISM: Artificial Sequence
<220> FEATURE:
<223> OTHER INFORMATION: Primer

<400> SEQUENCE: 48
gaggccactt gtgtagcgcc aagtg                                     25

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
gtgagtccat ggctgtcact g                                         21

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
cctgacttgg ctattctcag                                           20

BISPECIFIC ANTIBODIES AGAINST CEACAM5 AND CD47

REFERENCE TO SEQUENCE LISTING

The content of the electronically submitted sequence listing in ASCII text file (Name: 4130_0050002_Seqlisting_ST25.txt; Size: 37,800 bytes; and Date of Creation: Dec. 17, 2021) filed with the application is incorporated herein by reference in its entirety.

FIELD OF THE INVENTION

The present invention relates to bispecific antibodies which bind to human carcinoembryonic antigen CEACAM5 (CEA) and to human CD47 (CEAxCD47 bispecific antibodies). In addition, the present invention relates to polynucleotides encoding such bispecific antibodies and vectors and host cells comprising such polynucleotides. The invention further relates to methods for selecting and producing such antibodies and to methods of using such antibodies in the treatment of diseases. The invention also relates to the therapeutic use of the CEAxCD47 bispecific antibodies in monotherapy and in combination therapy, especially with CEAxCD3 T-cell bispecific antibodies (TCB) and/or inhibitors of PD-1 or PD-L1.

BACKGROUND OF THE INVENTION

CEA belongs to the family of CEA-related cell adhesion molecules (CEACAMs) that comprises 12 closely related proteins in humans encoded by 22 genes divided among the CEACAM and pregnancy-specific glycoproteins (PSG) subgroups on chromosome 19q13 (Beauchemin N & Arabzadeh A, Cancer Metastasis Rev. 2013). CEACAMs are involved in a variety of physiological processes such as cell-cell recognition and modulate cellular processes ranging from the shaping of tissue architecture and neovascularization to the regulation of insulin homeostasis, and T-cell proliferation; CEACAMs have also been identified as receptors for host-specific viruses and bacteria (Kuespert K et al., Curr Opin Cell Biol. 2006). CEA (CEACAM5 or CD66e; UniProtKB—P06731) is present early in embryonic and fetal development and maintains its expression in normal adult tissues. Its main site of expression is in columnar epithelial and goblet cells of the colon, particularly in the upper third of the crypt and at the free luminal surface.

CEA is (over-) expressed in tumors of epithelial origin, including but not limited to colorectal, gastric, lung, and pancreatic carcinomas (reviewed in Beauchemin N & Arabzadeh A, Cancer Metastasis Rev. 2013), where it loses its apical expression resulting in distribution over the entire cell surface (Hammarström, Semin Cancer Biol 1999).

A method for treating CEA expressing cancer by a combination of a human PD-1 axis antagonist and a T-cell redirecting and activating anti-CEA/anti-CD3 bispecific antibody is mentioned in US20140242079 and WO2017118657 (each of which is incorporated by reference in its entirety) and clinical results have been presented at ASCO annual meeting 2017 (Tabernero et al., J Clin Oncol 35, 2017 (suppl; abstr 3002)).

A method of treating tumors by administering immune checkpoint antagonists binding two or more different targets of an immune checkpoint pathway, and a T-cell redirecting agent binding to CEA and a T-cell surface antigen is mentioned in WO2015112534. A class I antibody binding to CEACAM5 and granulocytes is mentioned in US20110064653.

Human CD47 (UniProtKB—Q08722 (CD47 HUMAN; IAP)) is a transmembrane protein that binds the ligands thrombospondin-1 (TSP-1) and signal-regulatory protein alpha (SIRPα; CD172a; UniProtKB P78324) and can act as a "don't eat me" signal to the immune system, especially for macrophages which express SIRPα. Potent inhibition (low IC50) of the binding of SIRPα to CD47 on the surface of tumor cells is a measure to increase the phagocytosis of tumor cells by macrophages. CD47 is involved in a range of cellular processes, including apoptosis, proliferation, adhesion, and migration. Furthermore, it plays a key role in immune and angiogenic responses. CD47 is overexpressed in tumor cells from patients with both hematological and solid tumors. Antibodies against CD47 are described in the state of the art and have shown promising preclinical and early clinical activity in different tumor entities, including hematological malignancies such as lymphoma and solid tumors, for example gastric cancer (Weiskopf K., European Journal of Cancer 76 (2017) 100-109; Huang Y et al., J Thorac Dis 2017; 9(2):E168-E174; Kaur et al., Antibody Therapeutics, 3 (2020) 179-192). Antibodies of the IgG1 subclass that bind CD47 can result in the depletion of platelets and reduction of red blood cells (RBC) and hemoglobin in a Fc-dependent manner (see e.g. US20140140989). For avoiding this adverse effect, in WO2017196793 there is described a mutant form of the IgG4 subclass of an anti-CD47 antibody (IgG4PE, with the S228P mutation as well as a L235E mutation to reduce FcγR binding). Such anti-CD47 antibody with severely reduced FcγR binding and effector function does not result in such platelet depletion. A single domain bispecific antibody against CD47 and CD20 was described by von Bommel P E et al. (Oncoimmunol. 7 (2018) e386361) and Piccione E C et al. (mAbs 7 (2015)946-956). Dheilly E. et al. (Mol. Thera. 25 (2017) 523-533; see also WO2014087248) describe a bispecific antibody against CD19 and CD47.

Bispecific antibodies against CEACAM5 and CD47 comprising a common heavy chain of SEQ ID NO:5 (VH-CH1) and a CD47-interacting variable light chain region VL of SEQ ID NO:10 are described in WO2019234576, EP19213002, and U.S. 62/943,726 (incorporated by reference in their entirety). A bispecific antibody against CD19 and CD47 comprising a common heavy chain of SEQ ID NO:5 and a CD47-interacting variable light chain region VL of SEQ ID NO:10 is described in WO2014087248 (incorporated by reference in its entirety). WO2018098384 relates to a bispecific antibody co-targeting CD47 and CEACAM5. EP3623388 relates to bispecific binding molecules comprising a tumor-targeting arm and a fusion protein with low affinity for blocking the interaction between CD47 and SIRPα. WO 2018/057955 relates to bispecific antibodies binding both CD47 and mesothelin and comprising a common heavy chain. WO2019016411 relates to bispecific antibody molecules targeting CD47 and a tumor antigen.

Considerable progress has been made in the treatment of hematological malignancies. That is in contrast to the advances made in the treatment of several types of advanced solid tumors. Despite certain progress in the treatment of locally advanced or especially metastatic solid cancer types, progression-free (PFS) and overall survival (OS) of patients suffering from advanced cancer like colorectal cancer, pancreatic cancer, lung cancer etc. is still rather limited and there is usually no cure. Much hope has been put into cancer immunotherapy and there are certain, but limited, successes.

Tumors develop measures to protect their cells from destruction by T-effector cells and other immune cells like macrophages. Cancer immunotherapy-based strategies in the last decade(s) have had some success in counteracting these tumor protective measures and re-directing T cells against cancer cells. The most prominent examples of such strategies are inhibitors/activators of certain immune checkpoints. For example, checkpoint inhibitors like PD-1 axis antagonists have shown to re-activate T-effector cells to fight certain solid cancers. But not all solid tumor types are responsive to PD-1 axis antagonists, and, even in those responsive types, often much less than 50% of patients have a relevant benefit from e.g. treatment with an anti-PD-1 or PD-L1 antibody. For example, less than 10% of the patients with advanced colorectal cancer are egligible for therapy with inhibitors of the PD-1 axis (especially the approximately 4% of advanced colorectal cancer patients showing Microsatellite Instability MSI in their cancer have some benefit).

Adoptive T-cell therapy with chimeric antigen receptor (CAR) T-cells and therapy with T-cell bispecific antibodies delivered promising clinical results in hematological malignancies. But clinical studies with adoptive T-cell therapies, e.g. CAR T-cells, in various solid tumors mostly showed no or only minor response rates (e.g. Xu et al., Expert Review of Anticancer Therapy 2017, 17, 1099-1106; Greenbaum et al., Biol Blood Marrow Transplant 2020 October; 26(10): 1759-1769).

US20140242079, WO2017055389, US20140242080, and Bacac et al. (Clin. Cancer Res., 22(13), 3286-97 (2016)) (each of which is incorporated by reference in its entirety) describe CEAxCD3 T-cell bispecific antibodies. T-cell bispecific antibodies from WO2017055389 show strongly increased T-cell activating potency/efficacy compared to cibisatamab in preclinical studies, one of these higher potency CEAxCD3 T-cell bispecific antibodies was in clinical development (RO7172508 in NCT03539484). As used herein, "TCB2014" refers to a bispecific antibody binding to CEA and CD3 in the 2+1 format as described in US20140242080, comprising as CDRs the CDRs as shown in SEQ ID NO:270-276 and 290-296 of US20140242080 (see also CDRs of SEQ ID NO:4-10 and 24-30 of US20140242079, incorporated by reference in its entirety). Tabernero et. al.'s presentation at the ASCO annual meeting 2017 (J Clin Oncol 35, 2017 (suppl; abstr 3002)) included phase 1 clinical data in patients with advanced/metastatic colorectal cancer, with the CEAxCD3 bispecific antibody RO 6958688 (cibisatamab) in monotherapy and in combination with the anti-PD-L1 antibody atezolizumab. Stable disease and partial responses have been found in cibisatamab monotherapy as well as in combination with the PD-L1 inhibitor atezolizumab. Since 2017 no new clinical data have been published for Cibisatamab CEAxCD3. One trial using Q3W 100 mg cibisatamab plus the PD-L1 inhibitor atezolizumab and pretreatment with the B-cell killing anti-CD20 antibody Obinutuzumab (to avoid formation of anti drug antibodies ADA as reported for cibisatamab) has been posted March 2019 (ClinicalTrials.gov. Identifier NCT038666339). To date, no data have been published. Recently a new clinical trial with Q3W 100 mg Cibisatamab plus atezolizumab plus RO712290 has been posted (April 2021, NCT04826003) in patients with advanced colorectal cancer showing Microsatellite Stability. RO712290 is a bispecific fusion protein binding to the Fibroblast activating Protein (FAP) and to the T-cell costimulatory factor 4-1BB, causing an additional activation of T-cells leading to increased efficacy/killing of tumor cells if combined with CEAxCD3, but also increased toxicity, e.g. increased cytokine release. MEDI-565 (AMG211), a further bispecific CEAxCD3 antibody, a single-chain antibody, has been in clinical development, and results from clinical trials with that antibody have been published (e.g. induction of stable disease, see e.g. M. Pishvaian et al., Clin Colorectal Cancer. 2016 December; 15(4) 345-351).

Increased efficacy was reported when the CEAxCD3 bispecific antibody was combined with a PD-L1 inhibiting antibody. These data show that efficacy can be achieved with a CEAxCD3 bispecific antibody in advanced solid tumors. But overall in monotherapy and also in the combination with a PD-L1 inhibitor, most of the patients in the clinical study were still progressing and those responding showed at best partial responses and stable disease, but no complete responses have been achieved.

One approach to get increased efficacy with a T-cell bispecific antibody like CEAxCD3 cibisatamb is the combination with a second medicine causing additional T-cell activation via an agonistic effect on costimulatory T-cell receptors like 4-1BB or CD28 and others. A well known side effect of T-cell bispecific antibodies is the induction of a cytokine release syndrome CRS which can be higher grade, e.g. grade 3 or even grade 5 (death). Addition of bispecific antibodies targeting T-cell costimulatory receptors to T-cell bispecific antibodies can cause considerable increase of cytokine release and therefore increased risk of higher grade CRS.

Another approach to get better results could be for example to add to T-cell bispecific antibodies not only an inhibitor of PD-1 checkpoint axis, but to add further checkpoint inhibitors or agonists. But so far, there are no promising clinical data for such a combination approach in advanced solid cancer like colorectal cancer etc available. Limited availability of T-cells within advanced solid tumors is certainly an important mechanism limiting the efficacy achievable with T-cell bispecific antibodies plus PD-1 axis inhibitors and/or other checkpoint inhibitors or plus bispecific agonists at T-cell costimulatory receptors.

T-cell bispecific antibodies TAAxCD3 (TAA=Tumor associated antigen like CEA and many others) are highly efficient in patients with hematological malignancies like Multiple Myeloma, B-cell malignancies like e.g. diffuse large B-cell lymphoma, follicular lymphoma etc. Clinical results with Cibisatamab CEAxCD3 show that there is efficacy of TAAxCD3 also in advanced solid tumors (see text above) but much less than achieved in hematological malignancies. Adding PD-1 axis inhibitors may add efficacy, but if at all only limited. Adding a bispecific antibody or fusion protein agonistic at a costimulatory T-cell receptor like CD28 or 4-1BB increases efficacy in preclinical tests, but also toxicity, e.g. increased cytokine release. Instead of aiming for additional activation of T-cells, it could be more successful to add a therapeutic agent re-directing to the tumor cells other immune cells, especially macrophages. This invention deals with bispecific antibodies CEAxCD47 re-directing and activating macrophages against CEACAM5-expressing solid tumors in 1. monotherapy and/ or 2. as a combination therapy especially with CEAxCD3 T-cell bispecific antibodies to increase the tumor cell killing effect of the CEAxCD3 bispecific antibodies. a and to avoid, in contrast to the combination with bispecific agonists at T-cell co-stimulatory receptors, increased risk of CRS.

Bispecific antibodies against CEACAM5 and CD47 are described in WO2019234576. One exemplary bispecific antibody described in WO2019234576 is K2AC22 (SEQ ID NO:65 of WO2019234576 shows the light chain of the CEACAM5 binding part of K2AC22, SEQ ID NO:6 of WO2019234576 shows the common heavy chain of K2AC22 and SEQ ID NO:10 shows the light chain of the CD47 binding part of K2AC22). However, there is still a need for improved bispecific antibodies against CEACAM5 and CD47, for example improved antibodies that combine high efficacy with low toxicity, low immunogenicity and favourable pharmacokinetic properties. It is thus an object of the present invention to provide new bispecific antibodies against CEACAM5 and CD47 which are advantageous over bispecific antibodies against CEACAM5 and CD47 of the prior art.

SUMMARY OF THE INVENTION

The present invention provides new bispecific antibodies with a first binding part capable of binding to human CEACAM5 and a second binding part capable of binding to human CD47. The bispecific antibodies according to the invention induce high phagocytic activity against tumor cells, both against tumor cells expressing CEACAM5 in high amounts and against tumor cells expressing CEACAM5 in low amounts. In one embodiment, the bispecific antibodies induce their anti-tumor cells effects mainly via optimized phagocytosis/antibody-dependent cellular phagocytosis (ADCP) due to involvement of immune cells, especially macrophages. In one embodiment, the bispecific antibodies according to the invention show a decreased ratio of CEACAM3 to CEACAM5 binding affinity respectively increased ratio of KD relative to CEACAM5-CD47 antibody K2AC22. In one embodiment, the bispecific antibodies according to the invention inhibit the binding of SIRPα to CD47 expressed on tumor cells, and increase phagocytosis of tumor cells. The disclosed bispecific antibodies that specifically bind to human CEACAM5 and human CD47 are also suitable for use in the treatment of tumors, especially in the treatment of solid tumors.

In one aspect, the present invention provides a bispecific antibody (further named also as a "CEAxCD47 bispecific antibody", or a "bispecific antibody according to the invention") comprising a first binding part specifically binding to human CEACAM5 (further named also as "CEA") and a second binding part specifically binding to human CD47 (further named also as "CD47") characterized in that:

a) the first binding part comprises as heavy chain variable region a heavy chain variable region comprising a CDRH1 of SEQ ID NO:1, a CDRH2 of SEQ ID NO:2 and a CDRH3 of SEQ ID NO:3, b) the first binding part comprises as light chain variable region a light chain variable region comprising a CDRL set selected from the group consisting of b1) a CDRL1 of SEQ ID NO:14, CDRL2 of SEQ ID NO:15, and CDRL3 of SEQ ID NO:16, or b2) a CDRL1 of SEQ ID NO:17, CDRL2 of SEQ ID NO:18, and CDRL3 of SEQ ID NO:19, b3) a CDRL1 of SEQ ID NO:20, CDRL2 of SEQ ID NO:21, and CDRL3 of SEQ ID NO:22, b4) a CDRL1 of SEQ ID NO:23, CDRL2 of SEQ ID NO:24, and CDRL3 of SEQ ID NO:25, and b5) a CDRL1 of SEQ ID NO:26, CDRL2 of SEQ ID NO:27, and CDRL3 of SEQ ID NO:28, c) the second binding part comprises as heavy chain variable region a heavy chain variable region comprising a CDRH1 of SEQ ID NO:1, a CDRH2 of SEQ ID NO:2 and a CDRH3 of SEQ ID NO:3, and as light chain variable region a light chain variable region comprising a CDRL1 of SEQ ID NO:7, a CDRL2 of SEQ ID NO:8, and a CDRL3 of SEQ ID NO:9.

The invention comprises further embodiments of this aspect:

In one embodiment, the invention relates to a bispecific antibody, comprising a first binding part specifically binding to human CEACAM5 and a second binding part specifically binding to human CD47 characterized in that a) the first and second binding parts comprise each as heavy chain variable region a heavy chain variable region comprising a CDRH1 of SEQ ID NO:1, a CDRH2 of SEQ ID NO:2 and a CDRH3 of SEQ ID NO:3, b) the first binding part comprises as light chain variable region a light chain variable region comprising a CDRL1 of SEQ ID NO:14, CDRL2 of SEQ ID NO:15, and CDRL3 of SEQ ID NO:16, and c) the second binding part comprises as light chain variable region a light chain variable region comprising a CDRL1 of SEQ ID NO:7, a CDRL2 of SEQ ID NO:8, and a CDRL3 of SEQ ID NO:9.

In one embodiment, the invention relates to a bispecific antibody, comprising a first binding part specifically binding to human CEACAM5 and a second binding part specifically binding to human CD47 characterized in that a) the first and second binding parts comprise each as heavy chain variable region a heavy chain variable region comprising a CDRH1 of SEQ ID NO:1, a CDRH2 of SEQ ID NO:2 and a CDRH3 of SEQ ID NO:3, b) the first binding part comprises as light chain variable region a light chain variable region comprising a CDRL1 of SEQ ID NO:17, CDRL2 of SEQ ID NO:18, and CDRL3 of SEQ ID NO:19, and c) the second binding part comprises as light chain variable region a light chain variable region comprising a CDRL1 of SEQ ID NO:7, a CDRL2 of SEQ ID NO:8, and a CDRL3 of SEQ ID NO:9.

In one embodiment, the invention relates to a bispecific antibody, comprising a first binding part specifically binding to human CEACAM5 and a second binding part specifically binding to human CD47 characterized in that a) the first and second binding parts comprise each as heavy chain variable region a heavy chain variable region comprising a CDRH1 of SEQ ID NO:1, a CDRH2 of SEQ ID NO:2 and a CDRH3 of SEQ ID NO:3, b) the first binding part comprises as light chain variable region a light chain variable region comprising a CDRL1 of SEQ ID NO:20, CDRL2 of SEQ ID NO:21, and CDRL3 of SEQ ID NO:22, and c) the second binding part comprises as light chain variable region a light chain variable region comprising a CDRL1 of SEQ ID NO:7, a CDRL2 of SEQ ID NO:8, and a CDRL3 of SEQ ID NO:9.

In one embodiment, the invention relates to a bispecific antibody, comprising a first binding part specifically binding to human CEACAM5 and a second binding part specifically binding to human CD47 characterized in that a) the first and second binding parts comprise each as heavy chain variable region a heavy chain variable region comprising a CDRH1 of SEQ ID NO:1, a CDRH2 of SEQ ID NO:2 and a CDRH3 of SEQ ID NO:3, b) the first binding part comprises as light chain variable region a light chain variable region comprising a CDRL1 of SEQ ID NO:23, CDRL2 of SEQ ID NO:24, and CDRL3 of SEQ ID NO:25, and c) the second binding part comprises as light chain variable region a light chain variable region comprising a CDRL1 of SEQ ID NO:7, a CDRL2 of SEQ ID NO:8, and a CDRL3 of SEQ ID NO:9.

In one embodiment, the invention relates to a bispecific antibody, comprising a first binding part specifically binding to human CEACAM5 and a second binding part specifically binding to human CD47 characterized in that a) the first and second binding parts comprise each as heavy chain variable region a heavy chain variable region comprising a CDRH1 of SEQ ID NO:1, a CDRH2 of SEQ ID NO:2 and a CDRH3 of SEQ ID NO:3, b) the first binding part comprises as light chain variable region a light chain variable region comprising a CDRL1 of SEQ ID NO:26, CDRL2 of SEQ ID NO:27, and CDRL3 of SEQ ID NO:28, and c) the second binding part comprises as light chain variable region a light chain variable region comprising a CDRL1 of SEQ ID NO:7, a CDRL2 of SEQ ID NO:8, and a CDRL3 of SEQ ID NO:9.

In one embodiment, the invention relates to a bispecific antibody according to the invention, characterized in comprising in the first binding part as variable heavy chain region a variable heavy chain region of SEQ ID NO:4 and as variable light chain region a variable light chain region selected from the group consisting of SEQ ID NO:32, SEQ ID NO:33, SEQ ID NO:34, SEQ ID NO:35, and SEQ ID NO:36 and comprising in the second binding part as variable heavy chain region a heavy chain variable chain region of SEQ ID NO:4 and as variable light chain region a variable light chain region of SEQ ID NO:10.

In one embodiment, the invention relates to a bispecific antibody according to the invention, characterized in comprising in the first binding part as variable heavy chain region a variable heavy chain region of SEQ ID NO:4 and as variable light chain region a variable light chain region of SEQ ID NO:32 and comprising in the second binding part as variable heavy chain region a variable chain region of SEQ ID NO:4 and as variable light chain region a variable light chain region having of SEQ ID NO:10.

In one embodiment, the invention relates to a bispecific antibody according to the invention, characterized in comprising in the first binding part as variable heavy chain region a variable heavy chain region of SEQ ID NO:4 and as variable light chain region a variable light chain region of SEQ ID NO:33 and comprising in the second binding part as variable heavy chain region a variable chain region of SEQ ID NO:4 and as variable light chain region a variable light chain region having of SEQ ID NO:10.

In one embodiment, the invention relates to a bispecific antibody according to the invention, characterized in comprising in the first binding part as variable heavy chain region a variable heavy chain region of SEQ ID NO:4 and as variable light chain region a variable light chain region of SEQ ID NO:34 and comprising in the second binding part as variable heavy chain region a variable chain region of SEQ ID NO:4 and as variable light chain region a variable light chain region having of SEQ ID NO:10.

In one embodiment, the invention relates to a bispecific antibody according to the invention, characterized in comprising in the first binding part as variable heavy chain region a variable heavy chain region of SEQ ID NO:4 and as variable light chain region a variable light chain region of SEQ ID NO:35 and comprising in the second binding part as variable heavy chain region a variable chain region of SEQ ID NO:4 and as variable light chain region a variable light chain region having of SEQ ID NO:10.

In one embodiment, the invention relates to a bispecific antibody according to the invention, characterized in comprising in the first binding part as variable heavy chain region a variable heavy chain region of SEQ ID NO:4 and as variable light chain region a variable light chain region of SEQ ID NO:36 and comprising in the second binding part as variable heavy chain region a variable chain region of SEQ ID NO:4 and as variable light chain region a variable light chain region having of SEQ ID NO:10.

In one embodiment, the invention relates to a bispecific antibody according to the invention, characterized in comprising in the first binding part a heavy chain of SEQ ID NO:5 and a light chain selected from the group consisting of SEQ ID NO:37, SEQ ID NO:38, SEQ ID NO:39, SEQ ID NO:40, and SEQ ID NO:41 and comprising in the second binding part a heavy chain of SEQ ID NO:5 and a light chain having of SEQ ID NO:11.

In one embodiment, the invention relates to a bispecific antibody according to the invention, characterized in comprising in the first binding part a heavy chain of SEQ ID NO:5 and a light chain of SEQ ID NO:37 and comprising in the second binding part a heavy chain of SEQ ID NO:5 and a light chain having of SEQ ID NO:11.

In one embodiment, the invention relates to a bispecific antibody according to the invention, characterized in comprising in the first binding part a heavy chain of SEQ ID NO:5 and a light chain of SEQ ID NO:38 and comprising in the second binding part a heavy chain of SEQ ID NO:5 and a light chain having of SEQ ID NO:11.

In one embodiment, the invention relates to a bispecific antibody according to the invention, characterized in comprising in the first binding part a heavy chain of SEQ ID NO:5 and a light chain of SEQ ID NO:39 and comprising in the second binding part a heavy chain of SEQ ID NO:5 and a light chain having of SEQ ID NO:11.

In one embodiment, the invention relates to a bispecific antibody according to the invention, characterized in comprising in the first binding part a heavy chain of SEQ ID NO:5 and a light chain of SEQ ID NO:40 and comprising in the second binding part a heavy chain of SEQ ID NO:5 and a light chain having of SEQ ID NO:11.

In one embodiment, the invention relates to a bispecific antibody according to the invention, characterized in comprising in the first binding part a heavy chain of SEQ ID NO:5 and a light chain of SEQ ID NO:41 and comprising in the second binding part a heavy chain of SEQ ID NO:5 and a light chain having of SEQ ID NO:11.

In one embodiment, the invention relates to a bispecific antibody that comprises CEACAM5 binding parts that are the same as those in the K2AC82, K2AC84, K2AC91, K2AC100, or K2AC117 bispecific antibody. In such an embodiment, the bispecific antibody comprises:

the light chain CDRs of SEQ ID NO:14-16, VL of SEQ ID NO:32, and/or VLCL of SEQ ID NO:37 (K2AC82), the CDRs of SEQ ID NO:17-19, VL of SEQ ID NO:33, and/or VLCL of SEQ ID NO:38 (K2AC84), the CDRs of SEQ ID NO:20-22, VL of SEQ ID NO:34, and/or VLCL of SEQ ID NO:39 (K2AC91), the CDRs of SEQ ID NO:23-25, VL of SEQ ID NO:35, and/or VLCL of SEQ ID NO:40 (K2AC100), the CDRs of SEQ ID NO:26-28, VL of SEQ ID NO:36, and/or VLCL of SEQ ID NO:41 (K2AC117), or derivatives comprising the CDR regions and/or the light and heavy chains of said antibodies as described above.

In one embodiment, the constant and variable framework region sequences are human.

In one embodiment, the bispecific antibody according to the invention is characterized in that each of the first and second binding part comprises an immunoglobulin heavy chain and an immunoglobulin light chain. In one embodiment, the bispecific antibody according to the invention is a full-length antibody. In one embodiment, the bispecific antibody according to the invention is characterized in being of human IgG1 type.

In one embodiment, the bispecific antibody according to the invention is characterized in comprising a first binding part specific for CEA, comprising a lambda light chain variable domain (VL) and a lambda light chain constant (CL) domain and a second binding part specific for CD47, comprising a kappa light chain variable domain (VK) and a kappa light chain constant domain (CK) (κλ bispecific antibody, κλ body). In one such embodiment the second binding part comprises as light chain LC (CD47 VKCK) the light chain of SEQ ID NO:11. The kappa light chain of SEQ ID NO:11 comprises as variable light chain domain the variable light chain domain of SEQ ID NO:10 (Mab CD47 VK) and as constant light chain domain the constant light chain domain of SEQ ID NO:13 (CD47 CK).

In one embodiment, the bispecific antibody according to the invention is of fully human bispecific IgG (especially IgG1) format and in addition a κλ bispecific antibody.

In one embodiment, the bispecific antibody according to the invention is characterized in being a κλ bispecific antibody and comprising a common heavy chain (cHC). In one embodiment, the common heavy chain comprises as variable heavy chain domain VH a variable heavy chain domain of SEQ ID NO:4. In one embodiment, the bispecific antibody according to the invention is characterized in comprising a common heavy chain VH-CH1 of SEQ ID NO:5. In one embodiment, the bispecific antibody according to the invention is characterized in comprising a common heavy chain (VH-CH1-CH2-CH3) of SEQ ID NO:6.

In one embodiment, the bispecific antibody according to the invention is characterized in being monovalent for the first binding part and monovalent for the second binding part.

In one embodiment, the bispecific antibody according to the invention is characterized in competing for binding to CEACAM5 with anti-CEACAM5 antibody SM3E, which comprises as VK and VH domains VK and VH of sequences SEQ ID NO:43 and 44. In one embodiment, the bispecific antibody according to the invention is characterized in not competing for binding to CEACAM5 with cibisatamab and/or with MEDI-565 (AMG211; (M D Oberst et al., mAbs 6 (2014) 1571-1584)). In one embodiment, the bispecific CEAxCD47 antibodies according to the invention can be administered in parallel with CEAxCD3 bispecific antibodies cibisatamab and/or MEDI-565.

In another embodiment, the bispecific antibody according to the invention is characterized in being glycoengineered to have an Fc region with modified oligosaccharides. In another embodiment, the bispecific antibody according to the invention is characterized in comprising a Fc region that has been glycoengineered to have a reduced number of fucose residues as compared to the same bispecific antibody that has not been glycoengineered.

In one embodiment, the bispecific antibody according to the invention comprises a reduced amount of fucose in the oligosaccharide chain(s).

In one embodiment, the bispecific antibody according to the invention is characterized in that 50% to 100% of the N-linked oligosaccharides in the Fc region are nonfucosylated.

In one embodiment, the bispecific antibody according to the invention is characterized in that the fucose amount in the oligosaccharide chain(s) of the bispecific antibody according to the invention is reduced by 80% to 100% compared to the fucose content of the respective antibody, if no afucosylation method is applied.

In one embodiment, the bispecific antibody is characterized that 80% to 100% of the N-linked oligosaccharides in the Fc region are bisected and nonfucosylated. Afucosylated bispecific antibodies binding to CEACAM5 and CD47 in general and their production and purification are described in WO2019234576, U.S. 62/943,726 and EP19213002.

In one embodiment, the bispecific antibody according to the invention is characterized in comprising one, two or three amino acid substitutions in the Fc region selected from the group consisting of mono-substitutions S239D, I332E, G236A, of bi-substitutions I332E and G236A, S239D and I332E, S239D and G236A, and triple-substitution S329D and I332E and G236A; and a Fc region which has been glycoengineered to have a reduced number of fucose residues as compared to the same but non-glycoengineered bispecific antibody.

In one embodiment, the bispecific antibodies according to the invention are characterized by a ratio of the KD values for the binding to recombinant CEACAM3 and recombinant CEACAM5 of a factor of 100 or more (Example 3, Table 2).

In one embodiment, the bispecific antibodies according to the invention are characterized by a ratio of the KD values for the binding to recombinant CEACAM3 and recombinant CEACAM5 of a factor of between 100 and 200.

In one embodiment, bispecific antibodies of this invention have a relative uncoupling of binding to CEACAM5 and CEACAM3 (discriminative binding). Despite an, in comparison to bispecific CEAxCD47 antibody K2AC22, increased binding to the full length recombinant human CEACAM5 protein, the binding to full length recombinant human CEACAM3 does not increase proportionally. The quotient/ratio of the KD for the binding to the full length CEACAM3 vs. CEACAM5 shows an increase from 83 (K2AC22) to 137 (K2AC84) to 146 (K2AC100). This equals a 65%-76% increase in discriminative binding (Example 3, Table 2).

In one embodiment, the bispecific antibodies according to the invention are characterized in a concentration dependent phagocytosis (ADCP of CEACAM5 expressing tumor cell lines by human macrophages). ADCP is measured according to the invention as phagocytosis index (EC50 and/or maximum) by imaging, usually with an E:T ratio of 1:3 (human macrophages:target cells (tumor cells); see e.g. FIG. 2 and Tables 6 to 9 for EC50 values and for max. index of phagocytosis Emax). Results in FIG. 2 have been obtained with E:T of 1:3. Details of the assay are described in Example 7; imaging assay based on CellInsight™ CX5 High Content Screening Platform. If not otherwise stated, phagocytosis index values are measured by such imaging method.

In one embodiment, the bispecific antibodies according to the invention are characterized in an at least 8% increase in the maximum of phagocytosis index (Emax) of LoVo tumor cells in comparison to the phagocytosis index of K2AC22. In one embodiment, the increase is between 8% and 20% for LoVo tumor cells in comparison to the phagocytosis index of K2AC22. In one embodiment, the bispecific antibody according to the invention is characterized in an at least 8% increase in the maximum of phagocytosis index of Ls174T tumor cells in comparison to the phagocytosis index of K2AC22. In one embodiment, the increase is between 8% and 25% for Ls174T tumor cells in comparison to the phagocytosis index of K2AC22. (Example 7, Table 5). LoVo and LS174T are tumor cells with rather low expression of CEACAM5 (see Table 3 under Example 5).

In one embodiment, the bispecific antibodies according to the invention inhibit the interaction between human CD47 and human SIRPα. In one embodiment, the bispecific antibodies according to the invention inhibit the interaction between CD47 and SIRPα on MKN-45 cells with an IC50 which is a factor of 10 or more lower than the IC50 measured for K2AC22 under the same experimental conditions. In one embodiment, said factor is between 10 and 30. In one embodiment, the bispecific antibodies according to the invention inhibit the interaction between CD47 and SIRPα on MKN-45 cells with an IC50 of 0.1 nM or lower. In one embodiment, the bispecific antibodies according to the invention inhibit the interaction between CD47 and SIRPα on MKN-45 cells with an IC50 of 0.1 nM to 0.04 nM (see Example 10 and Table 12).

In one embodiment, the bispecific antibodies according to the invention are characterized in possessing two or more of the following properties: having a ratio of the KD values for the binding to recombinant CEACAM3 and recombinant CEACAM5 of a factor of 100 or more, having a relative uncoupling of binding to CEACAM5 and CEACAM3, having a concentration dependent ADCP, having at least an 8% increase in the maximum of phagocytosis index (Emax) of LoVo tumor cells in comparison to the phagocytosis index of K2AC22, and having the ability to inhibit the interaction between human CD47 and human SIRPα at more than 10 times lower IC50 compared to K2AC22.

Bispecific antibody K2AC22 is a bispecific antibody binding to human CEACAM5 and human CD47 and described in WO2019234576. K2AC22 comprises a common heavy chain of SEQ ID NO:6, in the CEACAM5 binding part the light chain of SEQ ID NO:42, and in the CD47 binding part the light chain of SEQ ID NO:11; CDRs of K2AC22 are shown in SEQ ID NO:1-3, 7-9, and 29-31 (Table 1).

In one embodiment, the bispecific antibody according to the invention is characterized in binding to recombinant human CD47 with a binding affinity (KD) of 100 nM to 600 nM, and in one embodiment with a binding affinity of 100 nM to 500 nM (measured by biolayer interferometry).

In one embodiment, the bispecific antibody according to the invention is characterized in binding to recombinant human CEACAM5 with a KD between 2 nM and 10 nM (Example 3, Table 2). In one embodiment, the bispecific antibodies of the invention have a 10-fold to 50-fold higher binding affinity (lower KD), and in one embodiment 20-fold to 50-fold, compared to the state of the art bispecific antibody K2AC22 (Example 3, Table 2).

In one embodiment, the bispecific antibodies according to the invention are useful for combination treatment with CEAxCD3 T-cell bispecific antibodies like cibisatamab.

In one embodiment, the bispecific antibody according to the invention is characterized in specifically binding to CEACAM5 but is not competing with TCB2014 and cibisatamab for binding to CEACAM5 on tumor cells, e.g. MKN-45 and LS174T (Example 8).

In one embodiment, the bispecific antibody according to the invention is characterized in that bispecific antibody TCB2014, binding to human CEACAM5 and CD3ε (supra), in a concentration of 300 nM, does not shift the EC50 of the binding curve of the bispecific antibody according to the invention to MKN-45 cells or in another embodiment to LS174T cells by more than a factor of 3, in one embodiment towards higher concentrations (Example 8 and FIG. 5). In such case the bispecific antibody according to the invention and TCB2014 are defined as "not competitive" and considered able to bind simultaneously to CEA without significantly interfering in binding to said CEA. In such case the bispecific antibody according to the invention and TCB2014 are defined as "not competitive" and considered able to bind simultaneously to CEA without significantly interfering in their binding to said CEA and can therefore develop its effect on phagocytosis (CEAxCD47) undisturbed and also its effect on T-cell activation (TCB2014 and cibisatamab) undisturbed, even if therapeutic levels of both drugs are simultaneously present in the blood and/or tumor tissue. This facilitates combination treatment of TCB2014 or cibisatamab with CEAxCD47 bispecific antibodies of the invention.

In one embodiment, the CEAxCD47 bispecific antibodies of the invention combined with CEAxCD3 bispecific antibody TCB2014 show at least additive or even synergistic % killing of tumor cells in an assay containing e.g. LoVo or LS174T tumor cells and human macrophages and T-cells derived from the same volunteer human donor.

In one embodiment, the CEAxCD47 bispecific antibodies of the invention, combined with CEAxCD3 bispecific antibody TCB2014 show at least additive or even synergistic % killing of tumor cells in an assay containing e.g. LoVo or LS174T tumor cells and human macrophages and T-cells derived from the same volunteer human donor.

The present invention further provides an expression vector comprising one or more polynucleotides encoding a bispecific antibody according to the invention.

The present invention further provides a host cell comprising the expression vector according to the invention.

The present invention further provides a method for the production of a bispecific antibody according to the invention, characterized in comprising:

a) culturing a host cell comprising an expression vector encoding said bispecific antibody under conditions which permit the production of said antibody of the invention, and b) isolating said antibody wherein said antibody is capable of specifically binding to CEACAM5 and CD47.

The second polypeptide encoding the antibody of the invention can be one polypeptide encoding all respective two different light chains and the common heavy chain or separate polypeptides, encoding separately the respective light and heavy chains. Also, the expression vector can be one, two or three vectors expressing the respective two different light chains and the common heavy chain.

The present invention further provides a method of inducing cell lysis of a tumor cell comprising contacting the tumor cell with a bispecific antibody according to the invention. The tumor cell is a human tumor cell, preferably in a patient. In one embodiment of a method to induce cell lysis of a tumor cell, the tumor cell is a colorectal cancer cell, NSCLC (non-small cell lung cancer) cell, gastric cancer cell, pancreatic cancer cell, breast cancer cell, or another tumor cell expressing CEACAM5.

The present invention further provides a method of treating a subject having a cancer that expresses CEACAM5, the method comprising administering to the subject a therapeutically effective amount of a bispecific antibody according to the invention.

The present invention further provides a method of increasing survival time in a subject having a cancer that expresses CEACAM5, said method comprising administering to said subject a therapeutically effective amount of a bispecific antibody according to the invention. A further embodiment of the invention is such a method according to the invention, characterized in that the cancer is colorectal cancer, non-small cell lung cancer (NSCLC), gastric cancer, pancreatic cancer, or breast.

The present invention further provides a method of treating a subject having a cancer that expresses CEACAM5, the method comprising administering to the subject a therapeutically effective amount of a bispecific antibody according to the invention. A further embodiment of the invention is such a method according to the invention, characterized in that a bispecific antibody according to the invention is administered in combination with chemotherapy or radiation therapy to a human subject.

The present invention further provides a bispecific antibody according to the invention, for use in the manufacture of a medicament for treating a subject having a cancer that expresses CEACAM5. A further embodiment of the invention is a bispecific antibody according to the invention, for use in such manufacture of a medicament according to the invention, characterized in that the cancer is selected from the group consisting of colorectal cancer, non-small cell lung cancer (NSCLC), gastric cancer, pancreatic cancer and breast cancer.

The present invention further provides a bispecific antibody according to the invention, for use in simultaneous, separate, or sequential combination with a second bispecific antibody comprising a third binding part specifically binding to human CEACAM5, and a fourth binding part specifically binding to human CD3ε in the treatment of a subject having a cancer that expresses CEACAM5. A further embodiment of the invention is a bispecific antibody according to the invention, for use in simultaneous, separate, or sequential combination with TCB2014 or cibisatamab in the treatment of a subject having a cancer that expresses CEACAM5.

A further embodiment of the invention is a bispecific antibody according to the invention, for use in simultaneous, separate, or sequential combination with said second bispecific antibody in the treatment of a subject having a cancer that expresses CEACAM5.

A further embodiment of the invention is a bispecific antibody according to the invention, for use according to the invention, characterized in that the bispecific antibody according to the invention and the second bispecific antibody are administered to said subject alternately in 6 to 15 day intervals.

A further embodiment of the invention is a bispecific antibody according to the invention, for use according to the invention, characterized in that the bispecific antibody according to the invention and the second bispecific antibody are administered to said subject simultaneously in 6 to 15 day intervals.

A further embodiment of the invention is a first bispecific antibody according to the invention, comprising a first binding part, specifically binding to human CEACAM5 and a second binding part, specifically binding to human CD47 according to the invention, for use according to the invention, characterized in that said cancer is colorectal cancer, non-small cell lung cancer (NSCLC), gastric cancer, pancreatic cancer and breast cancer.

A further embodiment of the invention is a method for the treatment of a human patient diagnosed with a tumor (cancer), especially a solid tumor, especially a solid cancer that expresses CEACAM5 especially colorectal cancer, non-small cell lung cancer (NSCLC), gastric cancer, pancreatic cancer and breast cancer, comprising administering an effective amount of an bispecific antibody according to the invention and a second bispecific antibody as described above, against CEA and CD3 (in one embodiment TCB2014, in one embodiment cibisatamab), to the human patient, the method comprising subsequently:

administering to the patient a dose of 0.1 to 10 mg/kg, in a further embodiment of 0.5 to 10 mg/kg, in a further embodiment of 1 to 2 mg/kg of said second anti CEAxCD3 antibody, e.g. weekly over 4 to 12 weeks or q2w, over 4 to 12 weeks and administering after these 4 to 12 weeks and after waiting for additional 2 or 3 or 4 elimination half-lives of said anti CEAxCD3 antibody to the patient a dose of 0.1 to 20 mg/kg of an antibody according to the invention, administering to the patient said antibody according to the invention q1, q2w, q3w or optionally q4w for e.g. 12 more weeks, waiting 2 or 3 or 4 elimination half-lives of said antibody according to the invention and then optionally repeating said cycle of CEA x CD3 bispecific antibody administration followed by administration of the bispecific antibody according to the invention and optionally repeat again that cycle etc.

As said CEA x CD3 bispecific antibody and the CEA x CD47 bispecific antibody according to the invention are not competitive, the two bispecific antibodies can also be administered in a manner ("simultaneous manner") that the patient experiences therapeutically effective plasma and tissue concentrations of both bispecific antibodies in parallel, e.g. by administration to the patient at about the same time a dose of 0.1 to 10 mg/kg, in a further embodiment of 0.5 to 10 mg/kg, in a further embodiment of 1 to 2 mg/kg of the CEA x CD3 bispecific antibody and a dose of 3 to 30 mg/kg in a further embodiment of 1 to 10 mg/kg of the CEA x CD47 bispecific antibody according to the invention, followed by one or more of these combined administrations at a frequency of q1w or q2w or q3w or optionally q4w. The term "q1w" means administration once a week; q2w means administration every two weeks etc.

For safety reasons it may be needed in one embodiment to start the therapy with the said second antibody CEAxCD3 w/o adding a bsAb of the invention and to start simultaneous administration of the two bsAb only after cytokine release syndrome (CRS) typical for a CEAxCD3 is over (usually after 2 or 3 doses of a TAAxCD3 antibody).

The present invention further provides a pharmaceutical composition comprising an antibody according to the invention and a pharmaceutically acceptable excipient or carrier.

The present invention further provides a pharmaceutical composition comprising an antibody according to the invention for use as a medicament. In one such embodiment the present invention provides a pharmaceutical composition comprising an antibody according to the invention for use as a medicament in the treatment of solid tumor disorders. In one embodiment, the pharmaceutical composition comprises an antibody according to the invention for use as a medicament in the treatment of colorectal cancer, NSCLC (non-small cell lung cancer), gastric cancer, pancreatic cancer or breast cancer.

The present invention further provides a composition comprising a bispecific antibody according to the invention, for use in simultaneous, separate, or sequential combination in the treatment of a subject having a cancer that expresses CEACAM5, with TCB2014 or cibisatamab as defined above, whereby said second bispecific antibody in a concentration of 300 nM does not shift the EC50 of the binding curve to MKN-45 and/or LS174T cells of the bispecific antibody according to the invention by more than a factor of 3, in one embodiment towards higher concentrations. A further embodiment of the invention is such a composition according to the invention, characterized in that the cancer is colorectal cancer, non-small cell lung cancer (NSCLC), gastric cancer, pancreatic cancer, or breast cancer.

The present invention further provides the use of an antibody according to the invention for the manufacture of a pharmaceutical composition.

The present invention further provides use of an antibody according to the invention and a pharmaceutically acceptable excipient or carrier for the manufacture of a pharmaceutical composition.

The present invention further provides use of an antibody according to the invention for the manufacture of a medicament in the treatment of solid tumor disorders. A further embodiment of the invention is such use of an antibody according to the invention in the treatment of colorectal cancer, NSCLC (non-small cell lung cancer), gastric cancer, pancreatic cancer or breast cancer.

Another aspect of the invention provides a method of inducing cell lysis of a tumor cell comprising contacting the tumor cell with the bispecific antibody of any of above described embodiments. In some embodiments, the tumor cell is a colorectal cancer cell, NSCLC (non-small cell lung cancer), gastric cancer cell, pancreatic cancer cell or breast cancer cell. In one embodiment, the cell lysis is induced by antibody dependent cellular phagocytosis and/or antibody dependent cell mediated cytotoxicity of the bispecific antibody according to the invention.

Another aspect of the invention provides a method of treating a subject having a cancer that abnormally expresses CEACAM5, the method comprising administering to the subject a therapeutically effective amount of the bispecific antibody of any of above described embodiments.

Another aspect of the invention provides a method of treating a subject having a cancer that abnormally expresses CEACAM5, the method comprising administering to the subject a therapeutically effective amount of the bispecific antibody of any of above described embodiments in combination with a bispecific antibody binding to human CEA and human CD3. As the CEAxCD3 bispecific antibodies and the CEAxCD47 bispecific antibodies according to the invention are not or only minimally competing they can be not only given sequentially but also in parallel (simultaneously) which may well be an advantage because tumor cell killing via engagement of T-cells by the CEAxCD3 bispecific antibody and at the same time via engagement of macrophages by the CEAxCD47 bispecific antibody according to the invention may be additive or even synergistic, which means efficacy is increased if both drugs are given in parallel.

Another aspect of the invention provides a method of increasing progression free survival and/or overall survival time in a subject having a cancer that abnormally expresses CEACAM5, said method comprising administering to said subject a therapeutically effective amount of the bispecific antibody of any of above described embodiments. In one embodiment, the cancer is colorectal cancer, non-small cell lung cancer (NSCLC), gastric cancer, pancreatic cancer or breast cancer or another cancer expressing CEACAM5.

In certain embodiments of these methods, the bispecific antibody according to the invention is administered in combination with chemotherapy or radiation therapy. In one embodiment, the subject is a patient suffering from colorectal cancer or lung cancer or gastric cancer or pancreatic cancer or breast cancer or another cancer expressing CEACAM5.

Another aspect of the invention provides a method of treating a subject having a cancer that abnormally expresses CEACAM5, the method comprising administering to the subject a therapeutically effective amount of the bispecific antibody of any of above described embodiments in combination with a bispecific antibody against human CEA and human CD3epsilon.

Another aspect of the invention provides a method of increasing progression free survival time and/or overall survival time in a subject having a cancer that abnormally expresses CEACAM5, said method comprising administering to said subject a therapeutically effective amount of the bispecific antibody of any of above described embodiments. In one embodiment, the cancer is colorectal cancer, non-small cell lung cancer (NSCLC), gastric cancer, pancreatic cancer, or breast cancer.

In certain embodiments of these methods, the bispecific antibody according to the invention is administered in combination with chemotherapy or radiation therapy. In one embodiment, the subject is a cancer patient with colorectal cancer or lung cancer or gastric cancer or pancreatic cancer or breast cancer or another CEACAM5 expressing cancer.

Another embodiment of the invention provides the use of a bispecific antibody according to the invention for any of the above described methods of treatment. In one embodiment, the cancer is selected from the group consisting of colorectal cancer, non-small cell lung cancer (NSCLC), gastric cancer, pancreatic cancer, and breast cancer.

BRIEF DESCRIPTION OF THE FIGURES

(FIG. 1A) SK-CO-1 cells, (FIG. 1B) MKN-45 cells, (FIG. 1C) HPAF-II cells, (FIG. 1D) SNU-C1 cells, (FIG. 1E) Ls174T cells and (FIG. 1F) LoVo cells. The EC50 of the bispecific antibodies according to the invention are lower than the EC50 of K2AC22, and the maximal binding (MFI) of the bispecific antibodies according to the invention is higher than the maximal binding of K2AC22.

FIGS. 2A-2F show the data obtained with macrophages derived from PBMCs (Peripheral Blood Mononuclear Cells) of six different human donors ((FIG. 2A) donor 862; (FIG. 2B) donor 872; (FIG. 2C) donor 873; (FIG. 2D) donor 863; (FIG. 2E) donor 874 and (FIG. 2F) donor 866). With most of the donors, phagocytosis induced by the two antibodies according to the invention is superior to K2AC22.

FIG. 3A shows the data obtained with MKN-45 as target cells and with macrophages derived from PBMCs (Peripheral Blood Mononuclear Cells) of two human donors (donor (D) 830; donor (D) 831) and FIG. 3B shows the data obtained with SNU-C1 as target cells and with macrophages derived from two human donors (donor (D) 831; donor (D) 833). With the donors, phagocytosis induced by the antibodies according to the invention is superior to K2AC22.

DETAILED DESCRIPTION OF THE INVENTION

Figure 1A:
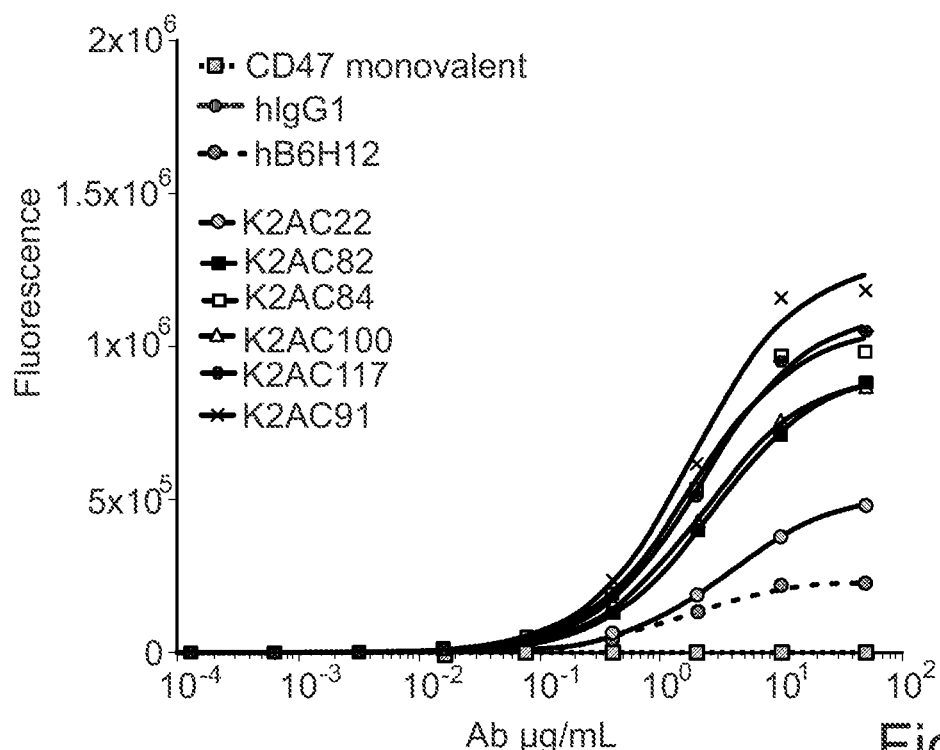
FIGS. 1A-1F. Concentration dependent binding of five CD47xCEACAM5 bispecific antibodies according to the invention (K2AC82, K2AC84, K2AC91, K2AC100, and K2AC117) as compared to state of the art bispecific CEAxCD47 antibody K2AC22. These figures also show the binding of the corresponding anti-CD47 monovalent antibody, of an irrelevant hIgG1 control (hIgG1, line under the line for CD47 monovalent), and of a bivalent anti-CD47 mAb (hB6H12, dotted line) on six CEACAM5-expressing cancer cell lines.
Figure 1B:
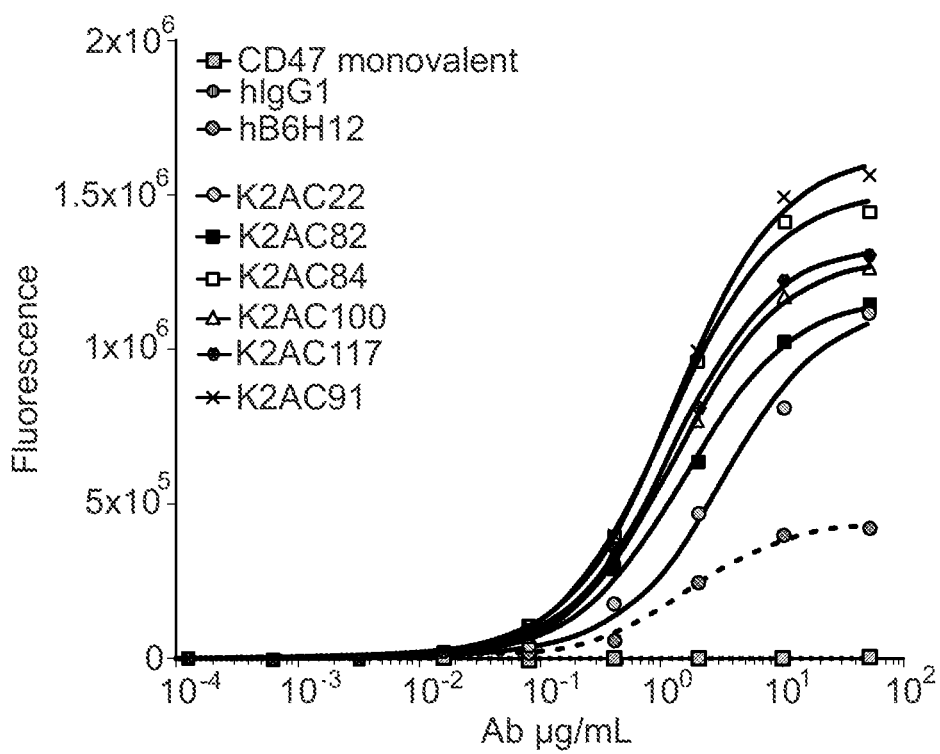
Figure 1C:
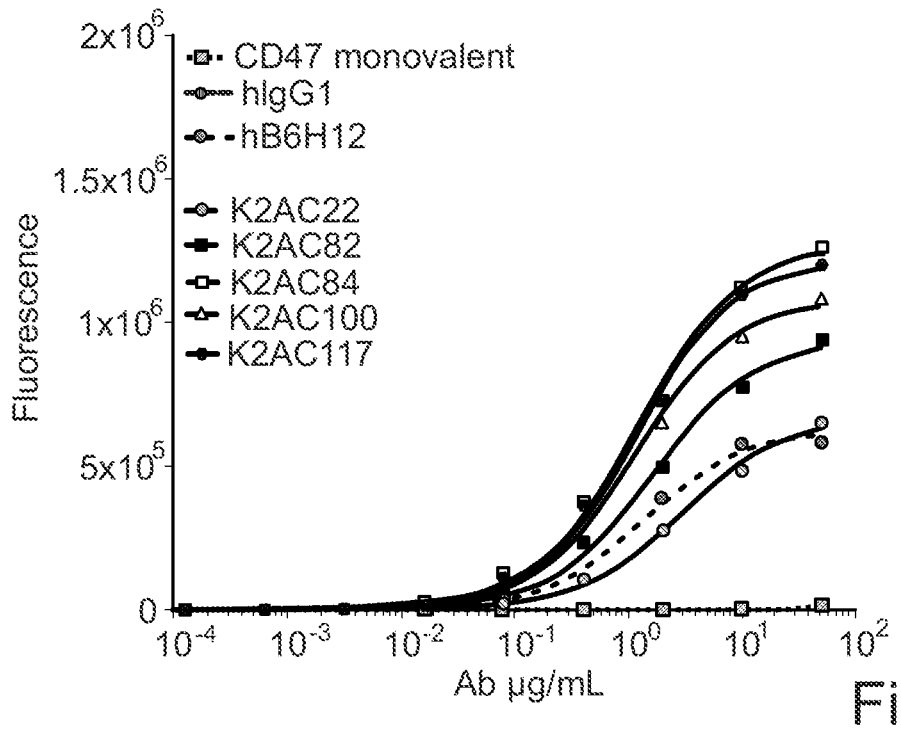
Figure 1D:
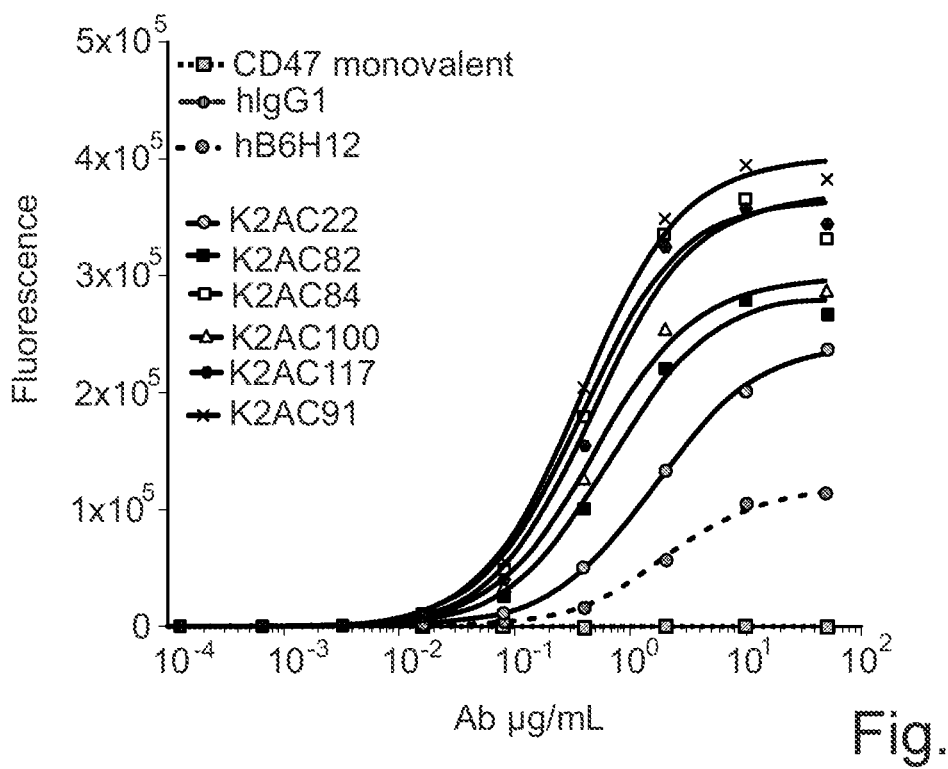
Figure 1E:
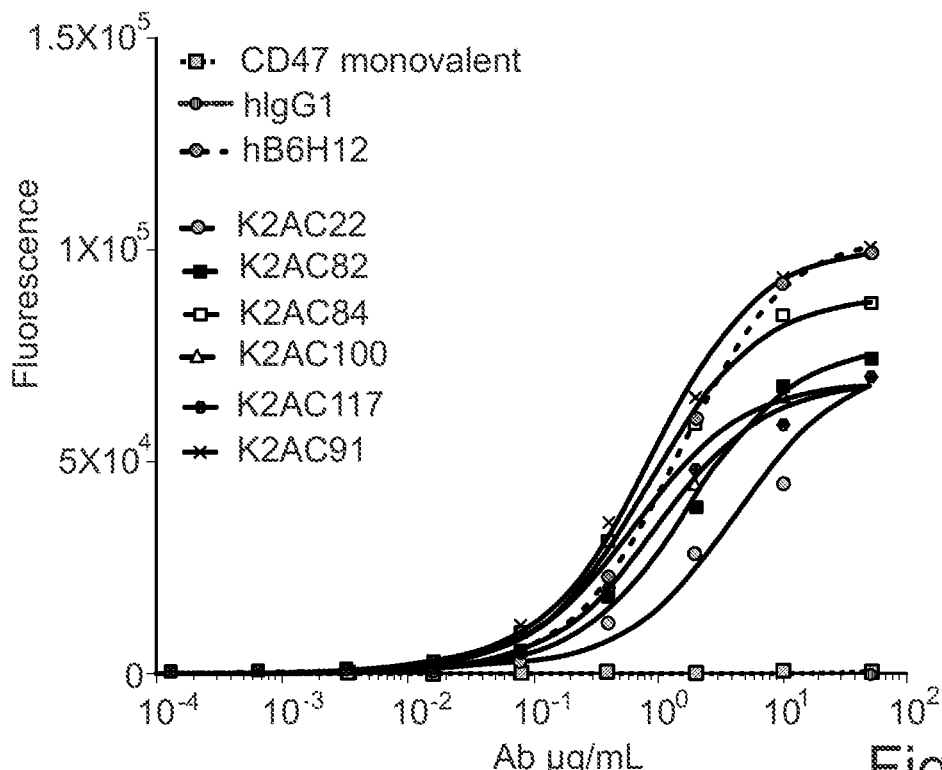
Figure 1F:
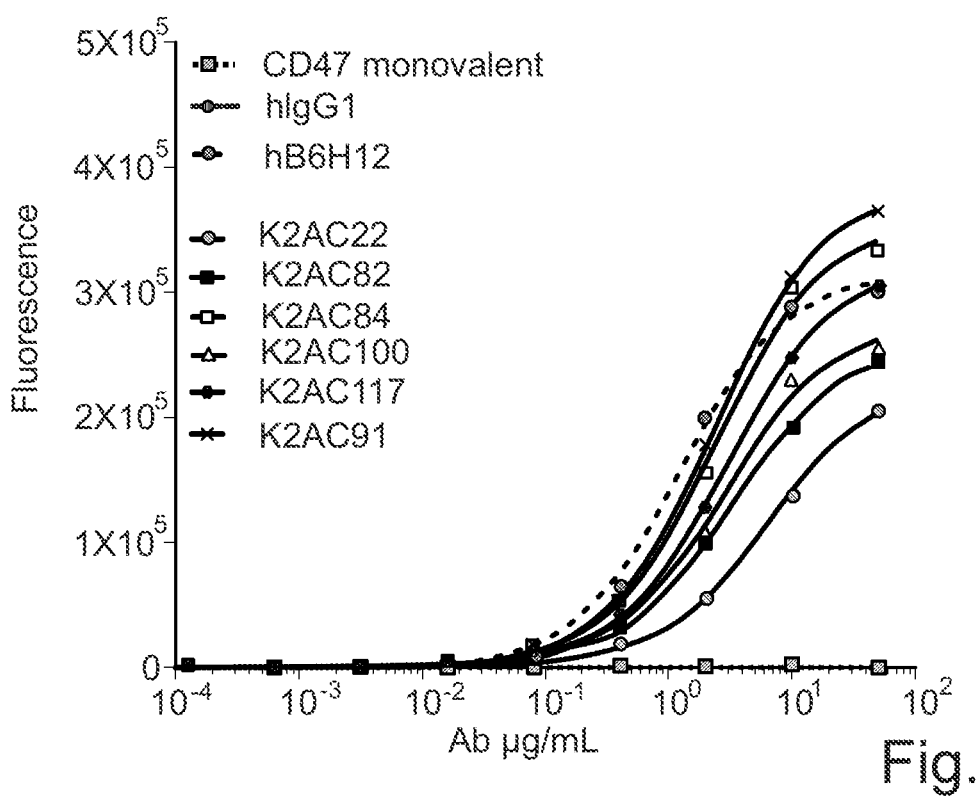
Figure 2A:
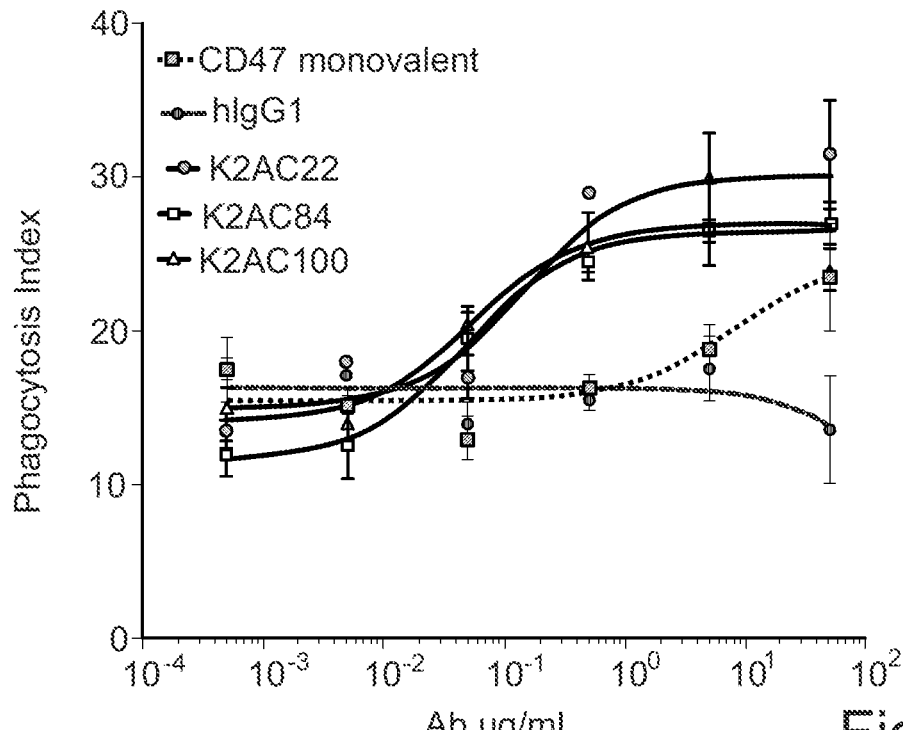
FIGS. 2A-2F. Concentration dependent phagocytosis of LoVo cancer cells induced by two CEACAM5xCD47 bispecific antibodies according to the invention (K2AC84 and K2AC100) as compared to the state of the art CEACAM5xCD47 bispecific antibody K2AC22. These figures also show the phagocytosis induced by the corresponding anti-CD47 monovalent antibody and an isotype control hIgG1.
Figure 2B:
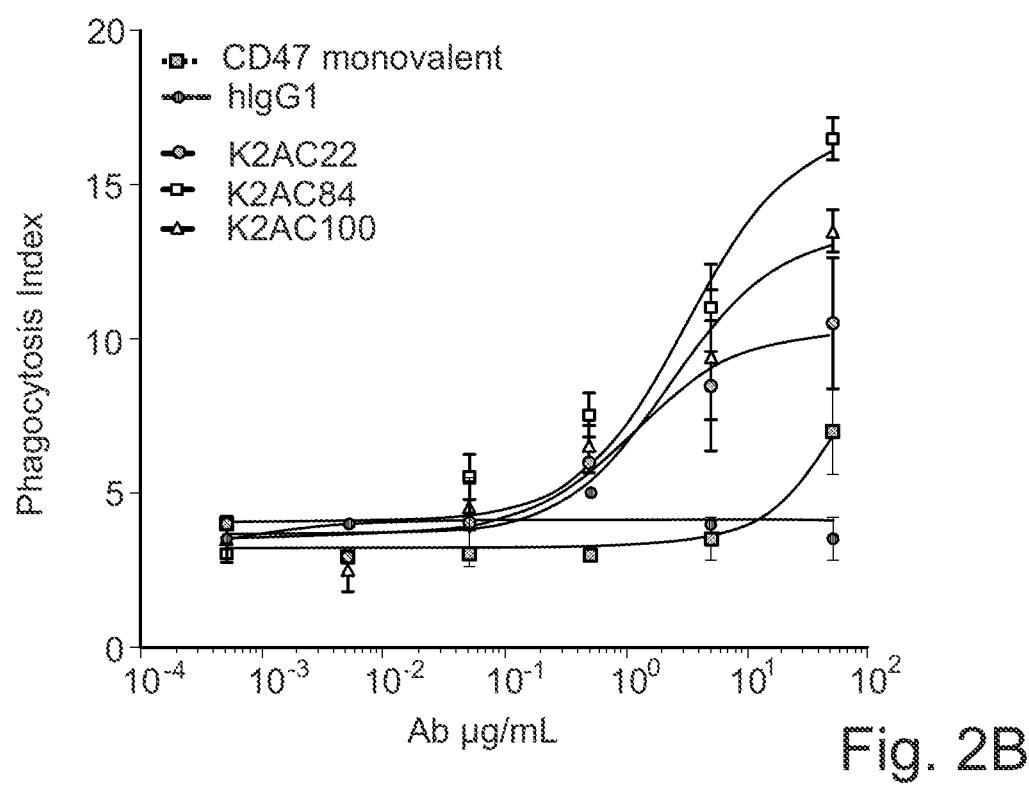
Figure 2C:
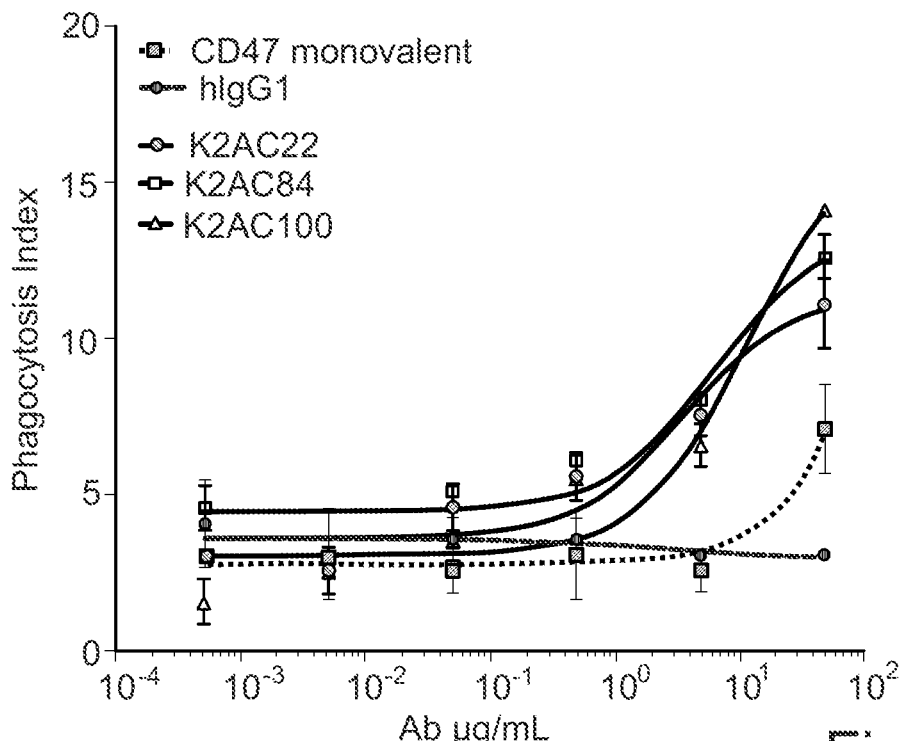
Figure 2D:
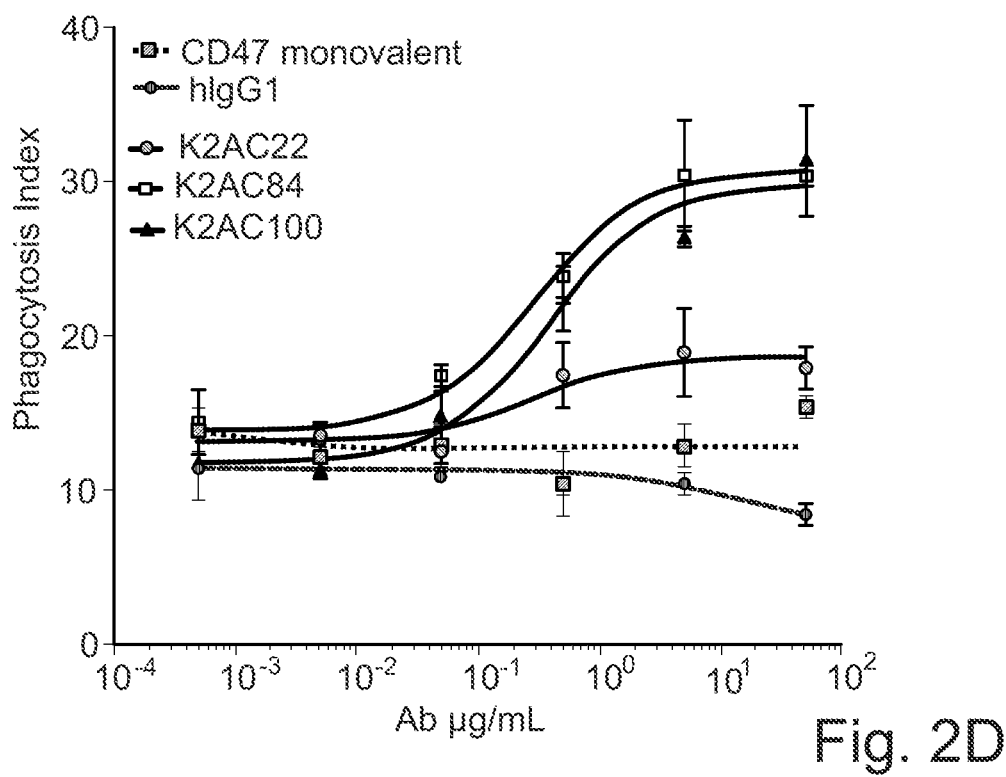
Figure 2E:
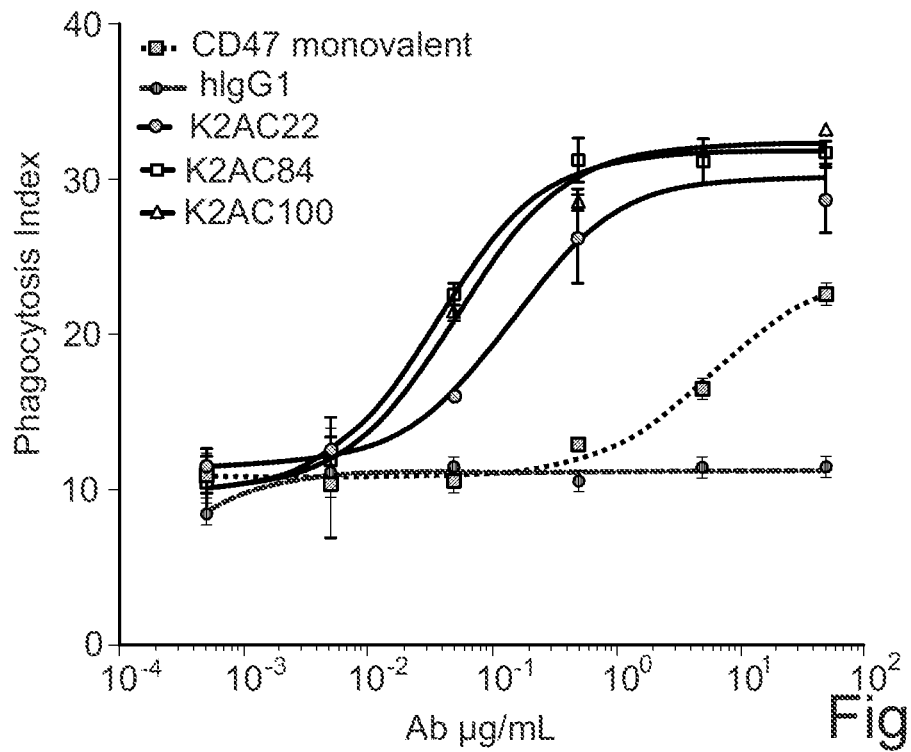
Figure 2F:
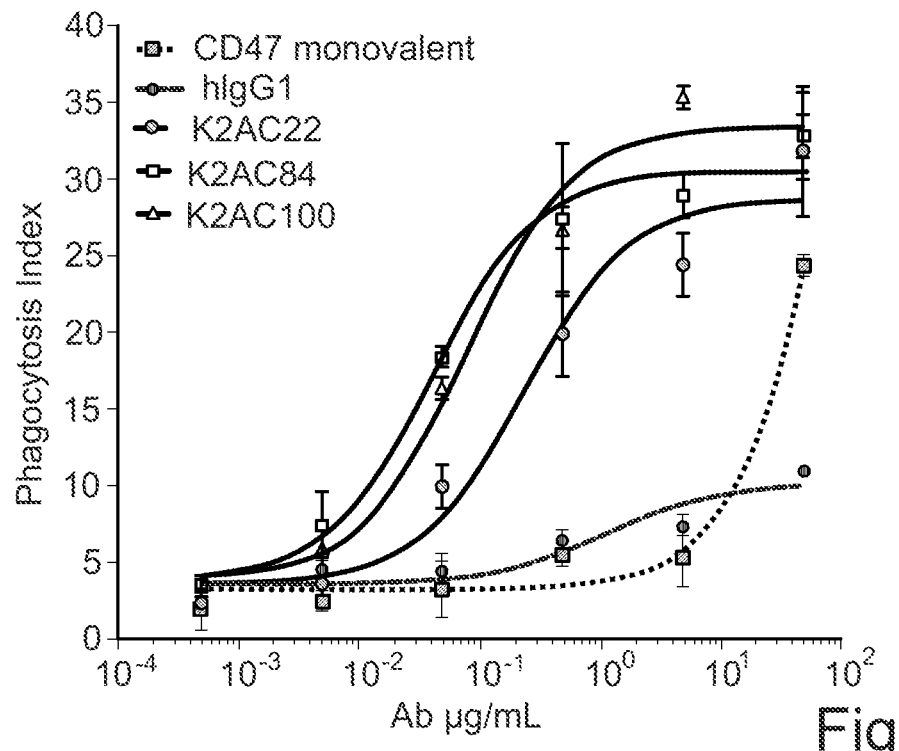

Terms are used herein as generally used in the art, unless otherwise defined as follows.

The antibodies according to the invention have one or more beneficial properties out of the following properties:
- ratio of KD values for the binding to CEACAM3 vs. CEACAM5,
- maximum of phagocytosis index (Emax) in low CEA expressing tumor cells, and/or
- inhibition (low IC50) of the binding of SIRPα to CD47 on the surface of tumor cells.

The antibodies according to the invention show surprisingly a beneficial ratio of binding to CEACAM3 vs. CEACAM5 as shown in Example 3 and Table 2. For example, K2AC100 shows a 25-fold higher binding affinity (lower KD) to CEACAM5 but surprisingly only a 14-fold higher binding affinity (lower KD) to CEACAM3, compared to the binding affinities (KD) of K2AC22. Similarly, K2AC84 shows a 46-fold higher binding affinity (KD) to CEACAM5 but surprisingly only a 28-fold higher binding affinity (KD) to CEACAM3, compared to the binding affinities (KD) of K2AC22. Thus, the ratio of the KD value for the binding to CEACAM3 to the KD value for the binding to CEACAM5 is 83 for K2AC22, but is 146 for K2AC100 and 137 for K2AC84.

While several family members like CEACAM5 or CEACAM6 are expressed by epithelial cells, other family members, such as CEACAM3 (CGM1 or CD66d; UniProtKB—P40198), are exclusively expressed on human granulocytes, a cell type e.g. involved in the clearance of bacterial infection (Kuespert K et al., Curr Opin Cell Biol. 2006; Pils S et al., Int J Med Microbiol. 2008). Despite the high sequence homology between CEACAM5 and CEACAM3, CEACAM3 does not support cell-cell adhesion in contrast to other members of the CEACAM family, but rather mediates the opsonin-independent recognition and elimination of a restricted set of Gram-negative bacteria including *Neisseria gonorrhoeae*, *Hemophilus influenzae*, and *Moraxella catarrhalis* (Kuroki et al., J. Biol. Chem. 1991; Pils S et al., Int J Med Microbiol. 2008). CEACAM3 is discussed as phagocytic receptor of the innate immune system (Schmitter et al., J Exp Med. 2004). According to the knowledge of the inventors a bispecific antibody against CEACAM5 and CD47, if considerably binding also to CEACAM3, would have an adverse effect on neutrophil granulocytes and could decrease the numbers of neutrophils, i.e. induce neutropenia by increased phagocytosis. This could increase the risk of developing bacterial infections which can, without immediate medical intervention, become life-threatening. High binding affinity is characterized by a low KD. The distribution of a CEA targeting bispecific antibody between CEACAM 5 and CEACAM3 is determined by the ratio of the binding affinities to these two CEACAM family members. A high ratio of the KD for binding to CEACAM3 versus the KD for the binding to CEACAM5 means less binding of the bispecific antibody to CEACAM3 compared to binding to CEACAM5, which would be beneficial.

The antibodies according to the invention show surprisingly a beneficial maximum value of phagocytosis index (Emax), in one embodiment in low CEA expressing tumor cells (like LoVo cell line) in comparison to the phagocytosis index of K2AC22 in the respective cell line. According to Table 5 bispecific antibodies of this invention show a 8.5 to 17% higher maximum of the phagocytosis index curve of LoVo cells (4000 CEACAM5 on cell surface) compared to the bispecific antibody of the state of art K2AC22. For LS174T cells (26000 CEACAM5 on cell surface) the maximum of the phagocytosis index is between 8.7 to 20.6% higher for the antibodies of the invention compared to K2AC22 (Table 5). In higher CEACAM5 expressing cells like SNU-C1 or MKN-45 the increase of Emax is lower.

A higher percentage of patients could be therefore successfully treated with bispecific antibodies according to the invention.

As disclosed in Examples 5 and 11, CEA expression in malignant cells can vary significantly in terms of RNA-expression or enumeration of cell surface CEA molecules. The CEA expressing cancer cell lines used to study phagocytosis activity of the bispecific antibodies of this invention express on average 108,000 CEA targets on the cell surface (Example 5, Table 3). Organoids derived from fresh tumor tissue of cancer patients (colorectal and lung) have been investigated by the methods described in Example 11. The average expression of CEACAM5 of these primary organoids has been found as 28,000 CEACAM5 targets per cell, i.e. a factor of approx 4 lower than average expression on the cell lines as shown in Table 3. Bispecific antibodies being improved for phagocytosis of malignant cells with lower CEACAM5 expression could thus be favorable for use in tumor therapy. Given the heterogenous and/or rather low expression e.g. in lung adenocarcinoma, in colorectal cancer and other CEACAM5 expressing tumors, such patients may be therefore successfully treated with CEAxCD47 bispecific antibodies of this invention.

Figure 4:
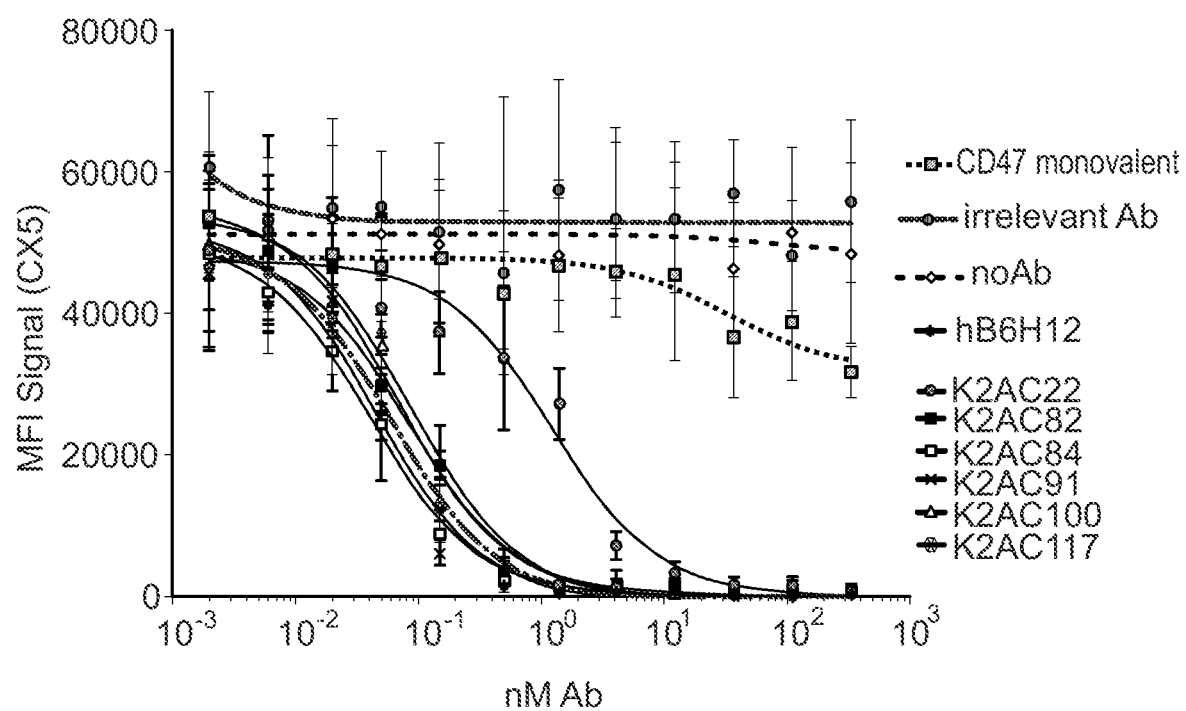
FIG. 4. CD47/SIRPα blocking activity by five CEACAM5xCD47 bispecific antibodies according to the invention (K2AC82, K2AC84, K2AC91, K2AC100 and K2AC177) as compared to the state of the art CEACAM5xCD47 bispecific antibody K2AC22. This figure also shows the CD47/SIRPα blocking activity by the corresponding anti-CD47 monovalent antibody. Two negative controls were added for comparison, with the addition of an hIgG1 isotype control (hIgG1) or without any Ab. The bivalent mAb hB6H12 was added as positive control. All the five CEACAM5xCD47 bispecific antibodies according to the invention (K2AC82, K2AC84, K2AC91, K2AC100 and K2AC177) showed an improved blocking activity as compared to the state of the art CEACAM5xCD47 bispecific antibody K2AC22.

The antibodies according to the invention show surprisingly a beneficial inhibition (low IC50) of the binding of SIRPα to CD47 on the surface of tumor cells in comparison to antibody K2AC22, as shown in Example 10 and FIG. 4. The interaction of SIRPα on macrophages with CD47 on tumor cells inhibits the phagocytosis of the tumor cells, that means effective inhibition of this interaction increases phagocytosis.

As used herein the term "Emax" describes the maximal activity of a compound. For example, in a cell killing assay, an Emax describes the elimination/killing of cancer cells (e.g. labelled with calcein AM, see Example 7) by macrophages within a given timeframe. This is of presumed high clinical importance as the total number of tumor infiltrating macrophages is limited: if for example double the number of tumor cells are eliminated per time interval, this equals half the number of macrophages need to be present to eliminate the same number of tumor cells per time.

As used herein the term "EC50" describes the compound concentration at which half of maximal activity (Emax/2) is reached. A low EC50 is useful in order to need to infuse a lower amount of compound and therefore to achieve e.g. lower production cost compared to a higher EC50 and/or potentially also lower rate of side effects. Emax and EC50 therefore describe different aspects of compound activity. For two compounds of comparable Emax, the EC50 becomes important as the same therapeutic effect could be achieved at a lower concentration and thus less amount of drug to be given and potentially lower rate of side effects to be achieved.

As used herein, the terms "antigen binding part" and "binding part" refer in their broadest sense to a part of an antibody that specifically binds an antigenic determinant such as CEA, CD47 and CD3.

More specifically, as used herein, a binding part that binds membrane-bound human carcinoembryonic antigen (CEA, same as CEACAM5) or to CD47 specifically binds to CEA or CD47, more particularly to cell surface or membrane-bound CEA or CD47. Therefore, each binding part binds either to CEA or CD47. By "specifically binding, specific for, binding to" is meant that the binding is selective for the antigen and can be discriminated from unwanted or non-specific interactions. In some embodiments, the extent of binding of an anti-target antibody to an unrelated, non-target protein is about 10-fold preferably >100-fold less than the binding of the antibody to said target as measured, e.g., by biolayer interferometry e.g. Octet®, surface plasmon resonance (SPR) e.g. Biacore®, enzyme-linked immunosorbent (ELISA) or flow cytometry (FACS). Targets are the proteins discussed herein—e.g. CEA, CD47, and CD3c.

The phrases specifically binding to CEA and CD47, binding to CEA and CD47, and specific for CEA and CD47 refer in one embodiment to an antibody, e.g., bispecific antibody, that is capable of binding to the targets CEA and CD47 with sufficient affinity such that the antibody is useful as a therapeutic agent in targeting tumor cells expressing CEACAM5 and CD47. Reference to binding to MKN-45, SNU-C1, LS174T, SK-CO-1, HPAF-II and/or LoVo cells with a particular EC50 value refers to an EC50 value measured by flow cytometry (see Example 6).

As used herein, the term "antibody" refers to an antibody comprising two heavy chains and two light chains. In one embodiment, the antibody is a full-length antibody. As used herein, the term "antibody heavy chain" refers to an antibody heavy chain, consisting of a variable region and a constant region as defined for a full-length antibody. As used herein, the term "antibody light chain" refers to an antibody light chain, consisting of a variable region and a constant region as defined for a full-length antibody.

The term "full-length antibody" denotes an antibody consisting of two "full-length antibody heavy chains" and two "full-length antibody light chains". A "full-length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3. A "full-length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full-length antibody domains are linked together via inter-polypeptide disulphide bonds between the CL domain and the CH1 domain and between the hinge regions of the full-length antibody heavy chains. Examples of typical full-length antibodies are natural antibodies like IgG (e.g. IgG 1 and IgG2), IgM, IgA, IgD, and IgE. The full-length antibody according to the invention is in one embodiment of human IgG1 type, in one further embodiment comprising one or more amino acid substitutions in the Fc part as defined below and/or being glycoengineered at polysaccharide chain attached to Asn297. The full-length antibody according to the invention comprise two binding parts each formed by a pair of VH and VL, one binding to CEA and the other binding to CD47.

As used herein and mentioned above, "Complementarity determining region(s)" (CDR(s)) describe the non-contiguous antigen combining sites (also known as antigen binding regions) found within the variable region of both heavy and light chain polypeptides. CDRs are also referred to as "hypervariable regions" (HVRs), and that term is used interchangeably herein with the term "CDR" in reference to the portions of the variable region that form the antigen binding regions. This particular region has been described by Kabat et al., Sequences of Proteins of Immunological Interest, 5th Ed. Public Health Service, National Institutes of Health, Bethesda, Md. (1991); which is incorporated herein by reference. The appropriate amino acid residues which encompass the CDRs as defined by Kabat are set forth below in the sequence list table. The exact residue numbers which encompass a particular CDR will vary depending on the sequence and size of the CDR. Those skilled in the art can routinely determine which residues comprise a particular CDR given the variable region amino acid sequence of the antibody. As used herein the term "comprising a CDRL1 of SEQ ID NO:x" refers to that the CDRL1 region of the referred variable light chain is of SEQ ID NO:x (comprising as CDRL1 a CDRL1 of SEQ ID NO:x). This is true also for the other CDRs. Unless otherwise indicated, HVR residues are numbered herein according to Kabat et al., supra and named as "CDRs" and references to the numbering of other specific amino acid residue positions in the bispecific antibodies according to the invention are also according to the Kabat numbering system.

As used herein, the terms "Fc region" and "Fc domain" refer to a C-terminal region of an IgG heavy chain; in case of an IgG1 antibody, the C-terminal region comprises —CH2-CH3 (see above). Although the boundaries of the Fc region of an IgG heavy chain might vary slightly, the human IgG heavy chain Fc region is usually defined to stretch from the amino acid residue at position Cys226 to the carboxyl-terminus. Constant regions are well known in the state of the art and e.g. described by Kabat, E. A., (see e.g. Johnson, G., and Wu, T. T., Nucleic Acids Res. 28 (2000) 214-218; Kabat, E. A., et al, Proc. Natl. Acad. Sci. USA 72 (1975) 2785-2788).

An IgG molecule carries two N-linked oligosaccharides in its Fc region, one on each heavy chain. As any glycoprotein, an antibody is produced as a population of glycoforms which share the same polypeptide backbone but have different oligosaccharides attached to the glycosylation sites. Antibodies with a reduced fucose content in glycan moieties exhibit higher antibody-dependent cellular cytotoxicity (ADCC) activity compared to a normally fucosylated antibody (Niwa R et al., Cancer Res, 64, 2127-33, 2004). A cell line with knockout of both alleles for the gene responsible for fucose addition ($\alpha$1,6-fucosyltransferase; FUT8) is described in U.S. Pat. Nos. 6,946,292, 7,425,446, 8,067,232 (each of which is incorporated by reference in its entirety). Using such a cell line the bispecific antibodies according to the invention can be produced with glycan moieties having a reduced fucose content and increased ADCC and antibody-dependent cellular phagocytosis (ADCP). Another technology which can be used to produce antibodies with reduced fucose content is described in U.S. Pat. No. 8,642,292 (incorporated herein by reference). This technology is designed to configure the stable integration of a heterologous bacterial enzyme into an antibody producer cell line like a CHO cell line or others. By this measure, the de novo synthesis of fucose from D-mannose is blocked. If in addition production cells are cultivated in fucose free medium, as a result antibodies with a stable level of afucosylation are produced. An exemplary method to produce and purify the afucosylated bispecific antibodies of this invention is described in Example 9 (1. and 2.).

Mutations within the Fc domain can also alter binding properties of the Fc domain to the different Fc receptors (WO2004063351, WO2004099249; WO2005018669, WO2005063815, WO2005110474, WO2005056759, WO2005092925, WO2005018572, WO2006019447, WO2006116260, WO2006023420, WO2006047350, WO2006085967, WO2006105338, WO2007021841, WO2007008943, WO2007024249, WO2007041635, WO2007048077, WO2007044616, WO2007106707, WO2008022152, WO2008140603, WO2008036688, WO2008091798, WO2008091954, WO2008092117, WO2008098115, WO2008121160, WO2008150494, WO2010033736, WO2014113510 (each of which is incorporated by reference in its entirety)).

The term "epitope" includes any polypeptide determinant capable of specific binding to an antibody. In certain embodiments, "epitope" includes chemically active surface groupings of molecules such as amino acids, sugar side chains, phosphoryl, or sulfonyl, and, in certain embodiments, may have specific three-dimensional structural characteristics, and or specific charge characteristics. An epitope is a region of a target that is bound by an antibody. In one embodiment, the bispecific antibody of the invention binds to the N-terminal domain of CEACAM5 (Ig-like V-type domain of amino acids 35-144, UniProtKB—P06731). Binding location of the CEAxCD47 bispecific antibodies to CEACAM5 is achieved via epitope binning. In epitope binning, antibodies are tested in a pairwise combinatorial manner, and antibodies that compete for the same binding region are grouped together into bins. Competition testing is performed herein with anti-CEA antibodies according to the state of the art and as described herein. In one embodiment, the bispecific antibody of the invention competes for binding to CEACAM5 with reference antibody SM3E. Competition is measured by an assay wherein biotinylated human CEACAM5 in a concentration of 0.5 µg/ml is immobilized and incubated with serial dilution (from 67 nM to 0.09 nM) of the reference. CEAxCD47 bispecific antibodies of the present invention are added at 0.1 µg/ml for 1 hour at room temperature. The plate is washed and the bound CEAxCD47 bispecific antibodies are detected.

As used herein, the term "a common heavy chain" (cHC) refers to a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH-HR-CH2-CH3. Common heavy chains suitable for the bispecific antibodies according to the invention are heavy chains of an anti-CD47 antibody as described in WO2012023053, WO2013088259, WO2014087248, and WO2016156537 (each of which is incorporated by reference in its entirety). In one embodiment, common heavy chain of the bispecific antibody according to the invention comprises as heavy chain CDRs a CDRH1 of SEQ ID NO:1, a CDRH2 of SEQ ID NO:2 and a CDRH3 of SEQ ID NO:3. In one embodiment, the cHC of the bispecific antibody according to the invention comprises as heavy chain variable region VH a VH region of SEQ ID NO:4. In one embodiment, the Fab part of the common heavy chain cHC of the bispecific antibody according to the invention is of SEQ ID NO:5 (VH-CH1). In one embodiment, the common heavy chain cHC of the bispecific antibody according to the invention is of SEQ ID NO:6 (VH-CH1-CH2-CH3). SEQ ID NO:6, is a heavy chain comprising in addition an IgG1 Fc part. In one embodiment, the antibody according to the invention is a κλ bispecific antibody comprising a cHC (κλ Body).

The κλ Body format allows the affinity purification of bispecific antibodies which are undistinguishable from a standard IgG molecule and with characteristics that are undistinguishable from a standard monoclonal antibody (see e.g. WO2013088259, WO2012023053), promising no or low immunogenicity potential in patients.

Bispecific antibodies of the invention, comprising a common heavy chain, can be made for example according to WO2012023053 (incorporated by reference in its entirety). The methods described in WO2012023053 generate bispecific antibodies that are identical in structure to a human immunoglobulin. This type of molecule is composed of two copies of a unique heavy chain polypeptide, a first light chain variable region fused to a constant Kappa domain and second light chain variable region fused to a constant Lambda domain. One binding site displays specificity to CEA and the other site displays specificity to CD47, wherein to each the heavy and the respective light chain contribute. The light chain variable regions can be of the Lambda or Kappa family and are preferably fused to a Lambda and Kappa constant domains, respectively. This is preferred in order to avoid the generation of non-natural polypeptide junctions. However, it is also possible to obtain bispecific antibodies of the invention by fusing a Kappa light chain variable domain to a constant Lambda domain for a first specificity or fusing a Lambda light chain variable domain to a constant Kappa domain for the second specificity. The other light chain is then always fully kappa (VL and CL) or fully lambda (so called hybrid formats of kappa lambda bispecific antibodies). The bispecific antibodies described in WO 2012023053 are "κλ Bodies". This κλ-Body format allows the affinity purification of a bispecific antibody that is undistinguishable from a standard IgG molecule with characteristics that are undistinguishable from a standard monoclonal antibody and, therefore, favourable as compared to previous formats including e.g. amino acid bridges or other unnatural elements.

As used herein, the terms "CEA" and "CEACAM5" refer to human carcinoembryonic antigen (CEA, CEACAM-5 or CD66e) which is a cell surface glycoprotein and a tumor-associated antigen (Gold and Freedman, J Exp. Med., 121: 439-462, 1965; Berinstein N L, J Clin Oncol., 20:2197-2207, 2002). UniProtKB-P0731 provides an exemplary human CEACAM5 sequence. As used herein, the term "CEACAM3" refers to human CEACAM3 (UniProtKB—P40198 (CEAM3 HUMAN) which is also a member of the carcinoembryonic antigen-related cell adhesion molecule (CEACAM) family.

In one embodiment, the bispecific antibody according to the invention is not competitive with TCB2014. Bispecific anti-CEACAM5 x anti-CD3ε antibody cibisatamab is described in Bacac et al. (Clin. Cancer Res., 22(13), 3286-97 (2016)). The antibody chains of TCB2014 are described in US20140242079 (SEQ ID NO:1, 2, 21, 22, 23, and 27 of US20140242079 (incorporated by reference in its entirety). A further bispecific CEAxCD3 Mab (TCB2017) is described in WO2017055389 as molecule B "2+1 IgG CrossFab, inverted" with charge modifications (VH/VL exchange in CD3 binder, charge modification in CEA binder, humanized CEA binder) (see SEQ ID NOs 34, 36-38 of WO2017055389 (incorporated by reference in its entirety)). As used herein in one embodiment "bispecific CEA x CD3 antibody" refers to antibody TCB2014, cibisatamab or antibody TCB2017.

Cibisatamab, TCB2014 and TCB2017 bind to epitopes of CEACAM5 located proximal to the cell membrane. In contrast the CEAxCD47 bispecific antibodies of this invention bind to an epitope distal of the cell membrane close to the N-terminus of CEACAM5 and are not competing with cibisatamab, TCB2014 and TCB2017 for binding to CEACAM5.

As used herein, the terms "specifically binding to CD47," "binding to CD47," and "CD47 binding part" refer in the context of the bispecific antibodies according to the invention to specificity for human CD47. Human CD47 is a multi-pass membrane protein and comprises three extracellular domains (amino acids 19-141, 198-207, and 257-268; see UniProtKB—Q08722). As used herein the "binding affinity to CD47" is measured quantitatively (KD) by biolayer interferometry (Octet® Technology) and/or surface plasmon resonance (Biacore™ Technology). In one embodiment, binding of the bispecific antibody according to the invention to CD47 occurs via one or more of said extracellular domains.

In one embodiment, the second binding part of the antibody according to the invention (specifically binding to human CD47) is characterized by a light chain comprising as light chain CDRs a CDRL1 of SEQ ID NO:7, a CDRL2 of SEQ ID NO:8, and a CDRL3 of SEQ ID NO:9, and a heavy chain comprising as heavy chain CDRs a CDRL1 of SEQ ID NO:1, a CDRL2 of SEQ ID NO:2, and a CDRL3 of SEQ ID NO:3. In one embodiment, the second binding part of the antibody according to the invention (specifically binding to human CD47) is characterized by a kappa light chain variable region of SEQ ID NO:10. In one embodiment, the second binding part of the antibody according to the invention (specifically binding to human CD47) is characterized by a kappa light chain of SEQ ID NO:11. In one embodiment, the second binding part of the antibody according to the invention (specifically binding to human CD47) is characterized by a heavy chain variable region of SEQ ID NO:4. In one embodiment, the second binding part of the antibody according to the invention (specifically binding to human CD47) is characterized by a heavy chain of SEQ ID NO:5. In one embodiment, the second binding part of the antibody according to the invention (specifically binding to human CD47) is characterized by a heavy chain of SEQ ID NO:6.

As used herein, the term "characterized by a heavy chain of SEQ ID NO:5" refers, as shown in Table 1, to the VH-CH1 part of the heavy chain which is the Fab part of the antibody according to the invention. Such heavy chain can comprise in addition, and according to common knowledge, further parts as hinge region, CH2, CH3, and can be in any antibody format, like in the F(ab')2 format. The preferred format is the common heavy chain format as described above As used herein, the terms "specifically binding to CEA," "binding to CEA," and "CEA binding part" refer to binding of a bispecific antibody according of the invention to recombinant human CEACAM5, wherein said antibody binds to recombinant human CEACAM3 with a KD value of 100 fold or higher compared to the KD value of the binding to recombinant human CEACAM5. The term "KD", as used herein, refers to the equilibrium dissociation constant between the bispecific antibody according to the invention and its antigen CEACAM5 or CEACAM3 and is specified in nM and can be e.g. measured by surface plasmon resonance and/or biolayer interferometry (Example 3).

Binding to CEA (CEACAM5) on cells is measured by using different tumor cell lines like LoVo, LS174T, MKN-45, SNU-C1, SK-CO-1, HPAF-II. The concentration of the antibody according to the invention is varied in an appropriate range in regard to a resulting EC50 value and Emax value for binding to cells as defined above. Binding curves of bispecific antibodies of the invention are shown in FIGS. 1A-1F, EC50 and Emax are listed in Table 4.

As used herein, the term "membrane-bound human CEA" refers to human carcinoembryonic antigen (CEA) that is bound to a membrane-portion of a cell or to the surface of a cell, in particular, the surface of a tumor cell.

As used herein, the terms "bispecific antibody binding to human CEA and human CD3" and "CEAxCD3 Mab" mean a bispecific antibody that binds to human CEACAM5 and CD3ε. Such antibodies are for example cibisatamab, "TCB2014" and "TCB2017". As used herein "TCB2014" refers to a bispecific antibody binding to CEA and CD3 as described in US20140242079 (incorporated by reference in its entirety) as SEQ ID NO:1, 2, 21, and 22. As used herein "TCB2017" refers to molecule B in the "2+1 IgG CrossFab, inverted" format with charge modifications (VH/VL exchange in CD3 binder, charge modification in CEA binder, humanized CEA binder); SEQ ID NOs 34, 36-38 of WO2017055389 (incorporated by reference in its entirety)). Further CEAxCD3 Mabs are described in WO2007071426, WO2013012414, WO2015112534, WO2017118675, US20140242079 and WO2017055389 (each of which is incorporated by reference in its entirety). A further CEAxCD3 Mab is cibisatamab (former R06958688) (see e.g. Bacac et al., Clin. Cancer Res., 22(13), 3286-97 (2016)). In one embodiment, said CEAxCD47 Mab according to the invention is not competitive and/or does not bind to the same epitope of human CEACAM5 as TCB2014 or TCB2017.

As used herein "CD3ε" and "CD3" refer to human CD3ε (UniProtKB—P07766 (CD3E HUMAN). The terms "antibody against CD3ε (CD3)" and "anti CD3ε (CD3) antibody" relate to an antibody that specifically binds to CD3ε. In one embodiment, the antibody against CD3ε specifically binds to the same epitope as anti-CD3 antibody SP34 (BD Biosciences Catalog No. 565983).

In one embodiment, the bispecific antibody of the invention does not compete with TCB2014 and/or TCB2017 for binding on CEA as presented on MKN-45 and/or LS174T cells. Therefore, TCB2014 in a concentration of 300 nM (TCB2014) or 30 nM (TCB2017) do not shift the EC50 of the phagocytosis index curve of said the bispecific antibody of the invention for MKN-45 and/or LS174T cells by more than a factor of 3, in one embodiment towards higher concentrations.

The concentration of 300 nM TCB2014 has been selected because concentrations of this magnitude have been measured in the plasma of patients treated with therapeutically effective doses of cibisatamab like 100 mg iv (for PK datra for cibisatamab see Melero et al., ASCO 2017, Abstract 2549 and Poster No. 41, Abstract in Journal of Clinical Oncology 35, no. 15 suppl (May 20, 2017) 2549-2549), for the respective clinical results see Tabernero et al., J. Clin. Oncol. 35, 2017 (suppl. Abstr. 3002)). In a currently actively recruiting study of cibisatamab in combination with a PD-L1 inhibitor 100 mg of cibisatamab are administered (ClinicalTrials.gov Identifier: NCT03866239). TCB2017 is in pre-clinical investigations approx. 10 to 100 times more potent than TCB2014 (as measured by binding affinity or tumor cell lysis in a T-cell dependent cellular cytotoxicity TDCC assay; see WO2017055389). Therefore, the shift of the EC50 of the phagocytosis curves of the bispecific antibodies of the invention by TCB2017 has been tested at 30 nM of TCB2017.

Competition in binding can be determined by flow cytometry-based measurement of the binding curve to MKN-45 cells and determination of the EC50 of this binding curve. Non-competition means that EC50 is shifted by less than a factor of 3, in one embodiment to towards higher concentrations, if 300 nM of TCB2014 are added to the assay. 300 nM are a concentration in the range of therapeutically active doses/plasma-concentrations of CEA x CD3 bispecific antibody (TCB2014) (Tabernero et al., J. Clin. Oncol. 35, 2017 (suppl. Abstr. 3002)). Non-competition by TCB2017 means that EC50 is shifted by less than a factor of 3 if 30 nM of TCB2017 are added to the assay.

As used herein, the term "not competitive" means that a second antibody (bispecific antibody against CEAxCD3c, like TCB2014 or TCB2017) in a concentration of 300 nM (TCB2014) or 30 nM (TCB2017) does not shift the EC50 of the binding curve of the bispecific antibody of the invention to MKN-45 cells by more than a factor of 3, in one embodiment towards higher concentrations.

As used herein the term "ADCP" refers to antibody-dependent cellular phagocytosis. As used herein phagocytosis, EC50 value of phagocytosis, maximum of phagocytosis, and phagocytosis index according to the invention refer to phagocytosis measured with tumor cell lines like e.g. LoVo, LS174T, SNU-C1 and/or MKN-45 by "imaging." An appropriate imaging method, with incubation at an effector (macrophages):target (tumor) cell ratio of e.g. 1:1 or 1:3 and with the "phagocytosis index" as readout (imaging determined ADCP") is described in Example 7. As used herein "phagocytosis of said bispecific antibody" means phagocytosis caused/induced by said antibody.

The terms "human IgG" and "hIgG" refer to a human antibody isotype. As used in experimental setups, these terms refer to a commercially available clinical-grade homogeneous preparation of human immunoglobulin IgG (available e.g. from Bio-Rad) that does not bind specifically to CD47 and CEACAM5.

Therapeutic Applications and Methods of Using Anti-CEA Antigen Binding Molecules The CEACAM x CD47 bispecific antibodies according to the invention are optimized for treatment of solid tumors mainly by macrophages mediated phagocytosis of the tumor cells, but also by ADCC, either in monotherapy or in combination therapy together with a CEAxCD3 T-cell bispecific antibodies like cibisatamab, TCB2014 or TCB2017 and/or PD-1 axis antagonist. The antibody according to the invention and the CEAxCD3 T-cell bispecific antibody can be administered as described below.

In a particular embodiment, the disease resp. solid tumor is a cancer that expresses or even overexpresses CEACAM5, including but not limited to the group of colorectal tumors, non-small cell lung tumors, gastric tumors, pancreatic tumors, and breast tumors. In a particular embodiment, the tumor is a colorectal tumor. In a particular embodiment the tumor is a gastric tumor or a gastroesophageal junction tumor. In a particular embodiment the tumor is a gastric tumor/gastroesophageal junction tumor expressing CEACAM5 and HER-2. In a particular embodiment the tumor is a lung tumor. All therapeutic applications methods of use, uses, combinations, etc. described herein are especially embodiments for the treatment of these tumors/diseases.

The inventors recognize that the antibodies according to the invention show low or no anti-drug antibody (ADA) formation potential respectively loss of drug exposure due to neutralizing ADA respectively loss of efficacy.

In one embodiment, the invention provides a method of treating carcinomas (cancer, tumors, for example, human carcinomas), especially CEACAM5 expressing tumors, in vivo. This method comprises administering to a subject a pharmaceutically effective amount of a composition containing a bispecific antibody of the invention. By "subject" is meant a human subject, in one embodiment a patient suffering from cancer/tumor/carcinoma.

CEACAM5 expression can be found in various tumor entities, especially in colorectal carcinoma, pancreatic adenocarcinoma, gastric cancer, non-small cell lung cancer, breast cancer among others. In healthy, normal glandular epithelia in the gastrointestinal tract, CEACAM5 is mainly expressed in a polarized pattern on the apical surface of the cells. This polarized expression pattern limits the accessibility by anti-CEA mono or bispecific antibodies which are administered systemically and therefore limits potential toxicity to healthy tissues. Together with the low affinity CD47 binding of the antibody of the invention this leads to no or limited phagocytosis of such normal cells by the antibody of the invention. This polarized expression pattern gets lost in the cells of gastrointestinal and other malignant tumors. CEACAM5 is expressed equally over the whole cell surface of the cancer cells that means cancer cells are much better accessible to an antibody of the invention than normal, healthy cells and can be selectively killed by the CEAxCD47 bispecific antibodies of the invention respectively by the combinations mentioned above. Expression of CEACAM5 in cancer cells is mostly higher than the expression in non-malignant cells.

In one embodiment, the bispecific antibodies of this invention can be used in monotherapy for the treatment of advanced solid tumors, in one embodiment CEACAM5 expressing tumors. In one embodiment, a bispecific antibody according to the invention is used in combination with a CEAxCD3 Mab in simultaneous, separate, or sequential combination. In one embodiment, a bispecific antibody according to the invention is used in combination with a CEAxCD3 Mab and/or a PD-1 axis antagonist in simultaneous, separate, or sequential combination. In one embodiment, a bispecific antibody according to the invention is used in combination with a PD-1 axis antagonist in simultaneous, separate, or sequential combination. Such PD-1 axis antagonists are described e.g. in WO2017118675. Such combinations attack the solid cancer by macrophages and T-cells. One CEAxCD3 Mab is in clinical development (cibisatamab; see ClinicalTrials.gov Identifier: NCT03866239) MEDI-565 was in clinical development but no active clinical trial could be identified in clinicaltrials.gov. In one embodiment, as bispecific antibody against CEA and CD3, antibody TCB2014 or cibisatamab is used.

The binder to CEA used in TCB2014 and cibisatamab has been derived from anti-CEA antibody PR1A3 (see e.g. EP2681244B1). This antibody binds to the so called B3 domain of CEA located proximal to the cell membrane. TCB2014 has a low nM binding affinity to CEA and shows efficacy in high doses (between 40 and 600 mg per dose and patient; (see e.g. Tabernero et al., J. Clin. Oncol. 35, 2017 (suppl. Abstr. 3002)). At highest doses nearly all CEA targets on the cell surfaces are occupied by the TCB2014. According to the knowledge of the inventors, combination of cibisatamab, TCB2014 or TCB2017 with CEAxCD47 may generate therapeutic plasma levels of both drugs at the same time and achieves best results (additive or even synergistic), if both drugs are non-competitive for the CEA antigen respectively binding to different epitopes which are not overlapping.

As used herein the terms "combination, simultaneous, separate, or sequential combination" of a an antibody according to the invention and a second bispecific antibody, binding to human CEA and human CD3ε refer to any administration of the two antibodies (or three antibodies in case of the combination of an antibody of the invention, a CEAxCD3 Mab and a PD-1 axis antagonist), either separately or together, where the two or three antibodies are administered as part of an appropriate dose regimen designed to obtain the benefit of the combination therapy, for example in separate, sequential, simultaneous, concurrent, chronologically staggered or alternating administration. Thus, the two or three antibodies can be administered either as part of the same pharmaceutical composition or in separate pharmaceutical compositions. The antibody according to the invention can be administered prior to, at the same time as, or subsequent to the administration of the second bispecific antibody, or in some combination thereof. Where the antibody according to the invention is administered to the patient at repeated intervals the second bispecific antibody can be administered prior to, at the same time as, or subsequent to, each administration of the antibody of the invention or some combination thereof, or at different intervals in relation to the treatment with the antibody of the invention, or in a single dose prior to, at any time during, or subsequent to the course of treatment with the antibody of the invention. In one embodiment, the antibody according to the invention and the second bispecific antibody are administered in alternating administration, in one embodiment, in intervals of 6 to 15 days between administration of the antibody of the invention and the second antibody. In such alternating administration the first dose can be the antibody of the invention or the second antibody.

The term "PD-1 axis antagonist" refers to an anti-PD-1 antibody or an anti-PD-L1 antibody. Anti-PD-1 antibodies are e.g. pembrolizumab (Keytruda®, MK-3475), nivolumab, pidilizumab, lambrolizumab, MEDI-0680, PDR001, and REGN2810. Anti-PD-1 antibodies are described e.g. in 5 WO200815671, WO2013173223, WO2015026634, U.S. Pat. Nos. 7,521,051, 8,008,449, 8,354,509, WO20091 14335, WO2015026634, WO2008156712, WO2015026634, WO2003099196, WO2009101611, WO2010/027423, WO2010/027827, WO2010/027828, WO2008/156712, and WO2008/156712 (each of which is incorporated by reference in its entirety).

Anti-PD-L1 antibodies are e.g. atezolizumab, MDX-1 105, durvalumab and avelumab. Anti-PD-L1 antibodies are e.g. described in WO2015026634, WO2013/019906, WO2010077634, U.S. Pat. No. 8,383,796, WO2010077634, WO2007005874, and WO2016007235 (each of which is incorporated by reference in its entirety).

With regard to combined administration of the antibody according to the invention and the second bispecific antibody, both compounds may be present in one single dosage form or in separate dosage forms, for example in two different or identical dosage forms.

If the antibody of the invention and the second antibody are not competing in regard to CEACAM5, in one embodiment both antibodies if desired by the physician, can be administered simultaneously. If the antibody of the invention and the second antibody are competing in regard to CEACAM5, in one embodiment both antibodies are administered in alternating administration.

The antibody of the invention will typically be administered to the patient in a dose regimen that provides for the most effective treatment of the cancer (from both efficacy and safety perspectives) for which the patient is being treated, as known in the art. Preferably tumor cells are attacked at the same time by T-cells and macrophages, to achieve full therapeutic potential of this approach, CEAxCD3 and CEAxCD47 bispecific antibody according to the invention have to be non-competitive regarding binding to CEA on cell surface.

As discussed above, the amount of the antibody administered and the timing of the administration of the antibody of the invention can depend on the type (e.g. gender, age, weight) and condition of the patient being treated, the severity of the disease or condition being treated, and on the route of administration. For example, the antibody of the invention and the second antibody can be administered to a patient in doses ranging from 0.1 to 100 mg/kg of body weight per day or per week in single or divided doses, or by continuous infusion. In one embodiment, each of the antibodies of the invention and the second antibody is administered to a patient in doses ranging from 0.1 to 30 mg/kg. In some instances, dosage levels below the lower limit of the aforesaid range may be adequate, while in other cases still larger doses may be employed without causing any harmful side effect.

As used herein, the term "half-life of the antibody" refers to the elimination half-life of said antibody as measured in a usual pharmacokinetic assay. An antibody according to the invention and the second bispecific antibody against CEA and CD3 have elimination half-life of 3-14 days.

In another aspect, the invention is also directed to the use of the bispecific antibody according to the invention in the treatment of disease, particularly cell proliferation disorders wherein CEACAM5 is expressed, particularly wherein CEACAM5 is abnormally expressed (e.g., overexpressed or expressed in a different pattern on the cell surface) compared to normal tissue of the same cell type. Such disorders include, but are not limited to colorectal cancer, NSCLC (non-small cell lung cancer), gastric cancer, gastroesophageal cancer, pancreatic cancer and breast cancer. CEACAM5 expression levels may be determined by different state of the art methods known (e.g., via immunohistochemistry assay, immunofluorescence assay, immunoenzyme assay, ELISA, flow cytometry, radioimmunoassay etc.).

In one aspect, bispecific antibodies of the invention can be used for targeting cells in vivo or in vitro that express CEACAM5. The bispecific antibodies of the invention are particularly useful in the prevention of tumor formation, eradication of tumors and inhibition of tumor growth or metastasis via the induction of ADCP and ADCC of tumor cells. The bispecific antibodies of the invention can be used to treat any tumor expressing CEACAM5. Particular malignancies that can be treated with the bispecific antibodies of the invention include, but are not limited to, colorectal cancer, non-small cell lung cancer, gastric cancer, gastroesophageal junction cancer, pancreatic cancer, and breast cancer.

The bispecific antibodies of the invention are administered to a mammal, preferably a human, in a pharmaceutically acceptable dosage form such as those discussed below, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes. The bispecific antibodies of the invention also are suitably administered by intra tumoral, peritumoral, intralesional, or perilesional routes, to exert local as well as systemic therapeutic effects.

For the treatment of disease, the appropriate dosage of bispecific antibodies of the invention will depend on the type of disease to be treated, the severity and course of the disease, previous therapy, the patient's clinical history and response to the antibody, and the discretion of the attending physician. The bispecific antibody of the invention is suitably administered to the patient at one time or over a series of treatments. The present invention provides a method for selectively killing tumor cells (also named herein as cancer cells) expressing CEACAM5.

This method comprises interaction of the bispecific antibodies of the invention with said tumor cells. These tumor cells may be from a human carcinoma including colorectal carcinoma, non-small cell lung carcinoma (NSCLC), gastric carcinoma, gastroesophageal junction cancer, pancreatic carcinoma and breast carcinoma.

In another aspect, the invention is directed to the use of the bispecific antibodies of the invention for the manufacture of a medicament for treating a disease related to abnormal CEACAM5 expression. In a particular embodiment, the disease is a cancer that expresses or even overexpresses CEACAM5, including but not limited to colorectal tumors, non-small cell lung tumors, gastric tumors, gastroesophageal junction tumors, pancreatic tumors, and breast tumors. In a particular embodiment, the tumors are colorectal tumors.

Compositions, Formulations, Dosages, and Routes of Administration

In one aspect, the present invention is directed to pharmaceutical compositions comprising the bispecific antibodies of the present invention and a pharmaceutically acceptable carrier. The present invention is further directed to the use of such pharmaceutical compositions in the method of treatment of disease, such as cancer, or in the manufacture of a medicament for the treatment of disease, such as cancer. Specifically, the present invention is directed to a method for the treatment of disease, and more particularly, for the treatment of cancer, the method comprising administering a therapeutically effective amount of the pharmaceutical composition of the invention.

In one aspect, the present invention encompasses pharmaceutical compositions, combinations, and methods for treating human carcinomas, tumors, as defined above. For example, the invention includes pharmaceutical compositions for use in the treatment of human carcinomas comprising a pharmaceutically effective amount of an antibody of the present invention and a pharmaceutically acceptable carrier.

The bispecific antibody compositions of the invention can be administered using conventional modes of administration including, but not limited to, intravenous, intraperitoneal, oral, intralymphatic or direct intratumoral administration. Intravenous administration or subcutaneous administration are preferred.

In one aspect of the invention, therapeutic formulations containing the bispecific antibodies of the invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or liquid formulations. Acceptable carriers, excipients, or stabilizers are nontoxic to recipients at the dosages and concentrations employed. The formulations to be used for in vivo administration must be sterile. This is readily accomplished by filtration through sterile filtration membranes. The most effective mode of administration and dosage regimen for the pharmaceutical compositions of this invention depends upon the severity and course of the disease, the patient's condition and response to treatment and the judgment of the treating physician. Accordingly, the dosages of the compositions may be flat doses or may be adapted to the individual patient, e.g. the body weight. Nevertheless, an effective dose of the compositions of this invention will generally be in a range from 0.1 to 30 mg/kg.

The bispecific antibodies of this invention have a molecular weight in a magnitude of 150 kDa per Mol. They carry in one embodiment a Fc part. The elimination half-life in patients is in a range of 3 to 14 days. This half-life allows for, but not limited to administration once a day, once a week, or once every two weeks or even 4 weeks.

The bispecific antibodies of the present invention and their respective compositions may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The composition comprising a bispecific antibody of the present invention will be formulated, dosed, and administered in a fashion consistent with good medical practice. Factors for consideration in this context include the particular disease or disorder being treated, the particular mammal being treated, the clinic condition of the individual patient, the cause of the disease or disorder, the site of delivery of the agent, the method of administration, the scheduling of administration, and other factors known to medical practitioners.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a bispecific antibody of the invention. The label or package insert indicates that the composition is used for treating the condition of choice. Moreover, the article of manufacture may comprise (a) a first container with a composition contained therein, wherein the composition comprises a bispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Further Embodiments of the Invention

1. A bispecific antibody comprising a first binding part specifically binding to human CEACAM5 and a second binding part specifically binding to human CD47 characterized in that:
   a) the first binding part comprises as heavy chain variable region a heavy chain variable region comprising a CDRH1 of SEQ ID NO:1, a CDRH2 of SEQ ID NO:2 and a CDRH3 of SEQ ID NO:3,
   b) the first binding part comprises as light chain variable region a light chain variable region comprising a CDRL set selected from the group consisting of
     b1) a CDRL1 of SEQ ID NO:14, CDRL2 of SEQ ID NO:15, and CDRL3 of SEQ ID NO:16, or
     b2) a CDRL1 of SEQ ID NO:17, CDRL2 of SEQ ID NO:18, and CDRL3 of SEQ ID NO:19,
     b3) a CDRL1 of SEQ ID NO:20, CDRL2 of SEQ ID NO:21, and CDRL3 of SEQ ID NO:22,
     b4) a CDRL1 of SEQ ID NO:23, CDRL2 of SEQ ID NO:24, and CDRL3 of SEQ ID NO:25, and
     b5) a CDRL1 of SEQ ID NO:26, CDRL2 of SEQ ID NO:27, and CDRL3 of SEQ ID NO:28,
   c) the second binding part comprises as heavy chain variable region a heavy chain variable region comprising a CDRH1 of SEQ ID NO:1, a CDRH2 of SEQ ID NO:2 and a CDRH3 of SEQ ID NO:3,
   and as light chain variable region a light chain variable region comprising a CDRL1 of SEQ ID NO:7, a CDRL2 of SEQ ID NO:8, and a CDRL3 of SEQ ID NO:9.

2. The bispecific antibody according to embodiment 1, characterized in comprising in the first binding part as variable heavy chain region a variable heavy chain region of SEQ ID NO:4 and as variable light chain region a variable light chain region selected from the group consisting of SEQ ID NO:32, SEQ ID NO:33, SEQ ID NO:34, SEQ ID NO:35, and SEQ ID NO:36 and comprising in the second binding part as variable heavy chain region a variable heavy chain region of SEQ ID NO:4 and as variable light chain region a variable light chain region having of SEQ ID NO:10.

3. The bispecific antibody according to embodiment 1, characterized in comprising in the first binding part a heavy chain comprising SEQ ID NO:5 and a light chain selected from the group consisting of SEQ ID NO:37, SEQ ID NO:38, SEQ ID NO:39, SEQ ID NO:40, and SEQ ID NO:41 and comprising in the second binding part a heavy chain of SEQ ID NO:5 and a light chain having of SEQ ID NO:11.

4. The bispecific antibody according to any one of the preceding embodiments, characterized in comprising as heavy chain a common heavy chain of SEQ ID NO:6.

5. The bispecific antibody of any one of the preceding embodiments, wherein said antibody is monovalent for the first binding part and monovalent for the second binding part.

6. The bispecific antibody of any one of the preceding embodiments, wherein the constant and variable framework region sequences are human.

7. The bispecific antibody of any one of the preceding embodiments, wherein the light chain of the first binding part is a lambda light chain (VLCL) and the light chain of the second binding part is a kappa light chain (VKCK).

8. The bispecific antibody of any one of the preceding embodiments, wherein the antibody is human IgG1 type.

9. The bispecific antibody of any one of the preceding embodiments, wherein said antibody comprises a Fc region that has been glycoengineered to have a reduced number of fucose residues as compared to the same bispecific antibody that has not been glycoengineered.

10. The bispecific antibody of any one of the preceding embodiments, characterized in that said bispecific antibody competes for binding to CEACAM5 with anti-CEACAM5 antibody SM3E, which comprises the variable light and heavy chain regions of SEQ ID NO:43 and 44.

11. The bispecific antibody of any one of the preceding embodiments, characterized in binding to recombinant human CEACAM5 with a binding affinity (KD) of 2 to 10 nM.

12. The bispecific antibody of any one of the preceding embodiments, characterized in binding to human recombinant CD47 with a binding affinity of 100 nM to 600 nM.

13. The bispecific antibody of any one of the preceding embodiments, characterized by a ratio of the KD values for the binding to recombinant CEACAM3 and recombinant CEACAM5 of a factor of 100 or more.

14. The bispecific antibody of embodiment 13, characterized by a ratio of the KD values for the binding to recombinant CEACAM3 and recombinant CEACAM5 of a factor of between 100 and 200.

15. The bispecific antibody of any one of the preceding embodiments, characterized in an at least 8% increase in the maximum of phagocytosis index of LoVo tumor cells in comparison to the phagocytosis index of bispecific antibody K2AC22.

16. The bispecific antibody of embodiment 15, characterized in an increase in the maximum of phagocytosis index between 8% and 20% for LoVo tumor cells.

17. The bispecific antibody of any one of the preceding embodiments, characterized in an at least 8% increase in the maximum of phagocytosis index of Ls174T tumor cells in comparison to the phagocytosis index of K2AC22.

18. The bispecific antibody of embodiment 17, characterized in an increase in the maximum of phagocytosis index between 8% and 25% for Ls174T tumor cells.

19. The bispecific antibody of any one of the preceding embodiments, characterized in inhibiting the interaction between CD47 and SIRPα on MKN-45 cells with an IC50 which is a factor of 10 or more lower than the IC50 measured for K2AC22 under the same experimental conditions.

20. The bispecific antibody of embodiment 19, characterized in inhibiting the interaction between CD47 and SIRPα on MKN-45 cells with an IC50 factor of between 10 and 30.

21. The bispecific antibody of any one of the preceding embodiments, characterized in inhibiting the interaction between CD47 and SIRPα on MKN-45 cells with an IC50 of 0.1 nM or lower.

22. The bispecific antibody of embodiment 21, characterized in inhibiting the interaction between CD47 and SIRPα on MKN-45 cells with an IC50 of 0.1 nM to 0.04 nM.

23. The bispecific antibodies of any one of the preceding embodiments, characterized in not competing for binding to CEACAM5 with cibisatamab.

24. The bispecific antibody of any one of the preceding embodiments, wherein said first bispecific antibody is characterized in that a second bispecific antibody, binding to human CEACAM5 and CD3ε, in a concentration of 300 nM, does not shift the EC50 of the binding curve of the first bispecific antibody to MKN-45 cells or to LS174T cells by more than a factor of 3 towards higher concentrations.

25. The bispecific antibody of embodiment 24, wherein said second bispecific antibody is TCB2014 or cibisatamab.

26. An isolated polynucleotide or set of polynucleotides encoding a bispecific antibody according to any one of the preceding embodiments.

27. An expression vector comprising the polynucleotide or polynucleotides of embodiment 26.

28. A host cell comprising the expression vector of embodiment 27.

29. A method for the production of a bispecific antibody according to any one of embodiments 1-25, comprising a) culturing a host cell of embodiment 28 under conditions which permit the production of said bispecific antibody, and b) isolating said antibody.

30. The bispecific antibody of any one of embodiments 1-25, for use in therapy of a human cancer.

31. A bispecific antibody for use according to embodiment 30, characterized in that the cancer is a solid cancer.

32. A bispecific antibody for use according to embodiment 30, characterized in that the cancer is a colorectal cancer, NSCLC (non-small cell lung cancer), gastric cancer, pancreatic cancer, breast cancer, or another CEACAM5 expressing cancer.

33. The bispecific antibody of any one of embodiments 1-25 for use in the manufacture of a medicament for treating a subject having a cancer that expresses CEACAM5.

34. The bispecific antibody of any one of embodiments 1-25 for use in simultaneous, separate, or sequential combination with a second bispecific antibody comprising a third binding part specifically binding to human CEACAM5, and a fourth binding part specifically binding to human CD3ε in the treatment of a subject having a cancer that expresses CEACAM5.

35. The bispecific antibody of any one of embodiments 1-25 for use in simultaneous, separate, or sequential combination wherein the second bispecific antibody is TCB2014 or cibisatamab.

36. The bispecific antibody for the use according to embodiment 34 or 35, characterized in that the bispecific antibody according to the invention and the second bispecific antibody are administered to said subject simultaneously in 6 to 15 day intervals.

37. A pharmaceutical composition comprising a bispecific antibody of any one of embodiments 1-25 and a pharmaceutically acceptable excipient or carrier.

38. The pharmaceutical composition of embodiment 37, for use as a medicament.

39. The pharmaceutical composition of embodiment 37 or embodiment 38, for use as a medicament in the treatment of solid cancer.

40. The pharmaceutical composition of any one of embodiments 37-39, for use as a medicament in the treatment of colorectal cancer, NSCLC (non-small cell lung cancer), gastric cancer, pancreatic cancer, or breast cancer.

41. A method of treating a subject having a cancer that expresses CEACAM5, the method comprising administering to the subject a therapeutically effective amount of the bispecific antibody of any one of embodiments 1-25 or the pharmaceutical composition of any one of claims 37-40.

42. The method of embodiment 41, wherein the cancer is a human cancer.

43. The method of embodiment 41 or 42, wherein the subject is a patient.

44. The method of any one of embodiments 41-43, characterized in that the cancer is a colorectal cancer cell, NSCLC (non-small cell lung cancer) cell, gastric cancer cell, pancreatic cancer cell, breast cancer cell, or another tumor cell expressing CEACAM5.

45. The method of any one of embodiments 41-44, wherein the bispecific antibody is administered in combination with chemotherapy or radiation therapy.

46. A method of treating a human patient with a tumor, comprising administering an effective amount of the CEACAM5 x CD47 bispecific antibody of any one of embodiments 1-25 and a second bispecific antibody against CEACAM5 and CD3.

47. The method of embodiment 46, wherein the CEACAM5 x CD47 bispecific antibody and the CEACAM5 and CD3 antibodies are not competitive.

48. The method of embodiment 46 or 47, wherein the antibodies are administered simultaneously.

49. The method of any one of embodiments 41 to 48, wherein the patient is administered one or more doses of 0.01 to 10 mg/kg of the bispecific antibody of any one of embodiments 1-25.

50. The method of any one of embodiments 46 to 48, wherein the patient is administered one or more doses of 0.01 to 10 mg/kg of the CEACAM5 x CD3 bispecific antibody and one or more doses of 1 to 20 mg/kg of the CEACAM5 x CD47 bispecific antibody.

51. The method of any one of embodiments 46-50, wherein the second antibody is TCB2014 or cibisatamab.

52. A method of increasing survival time in a subject having a cancer that expresses CEACAM5, said method comprising administering to said subject a therapeutically effective amount of the bispecific antibody of any one of embodiments 1-25.

53. The method of embodiment 52, characterized in that the cancer is colorectal cancer, non-small cell lung cancer (NSCLC), gastric cancer, pancreatic cancer, or breast cancer.

54. The method of any one of embodiments 52 or 53, wherein the bispecific antibody is administered in combination with chemotherapy and/or radiation therapy.

55. The method of any one of embodiments 52 to 54, wherein the patient is administered one or more doses of 0.01 to 10 mg/kg of the bispecific antibody of any one of embodiments 1-25.

TABLE 1

Sequence List

| Sequence Number | Relates to |
| --- | --- |
| SEQ ID NO:1 | Common heavy chain CDRH1 |
| SEQ ID NO:2 | Common heavy chain CDRH2 |
| SEQ ID NO:3 | Common heavy chain CDRH3 |
| SEQ ID NO:4 | Common heavy chain variable region VH |
| SEQ ID NO:5 | Common heavy chain (VH-CH1) |
| SEQ ID NO:6 | common heavy chain (VH-CH1-CH2-CH3) |
| SEQ ID NO:7 | CD47 binding part CDRL1 |
| SEQ ID NO:8 | CD47 binding part CDRL2 |
| SEQ ID NO:9 | CD47 binding part CDRL3 |
| SEQ ID NO:10 | CD47 binding part light chain variable region VK |
| SEQ ID NO:11 | CD47 binding part light chain (VKCK; K2) |
| SEQ ID NO:12 | CD47 binding part light chain (VKCK; nucleic acid); (K2) |
| SEQ ID NO:13 | CD47 binding part constant light chain kappa (CK) |
| SEQ ID NO:14 | CEACAM5 binding part AC82 CDRL1; |
| SEQ ID NO:15 | CEACAM5 binding part AC82 CDRL2 |
| SEQ ID NO:16 | CEACAM5 binding part AC82 CDRL3 |
| SEQ ID NO:17 | CEACAM5 binding part AC84 CDRL1 |
| SEQ ID NO:18 | CEACAM5 binding part AC84 CDRL2 |
| SEQ ID NO:19 | CEACAM5 binding part AC84 CDRL3 |
| SEQ ID NO:20 | CEACAM5 binding part AC91 CDRL1 |
| SEQ ID NO:21 | CEACAM5 binding part AC91 CDRL2 |
| SEQ ID NO:22 | CEACAM5 binding part AC91 CDRL3 |
| SEQ ID NO:23 | CEACAM5 binding part AC100 CDRL1 |
| SEQ ID NO:24 | CEACAM5 binding part AC100 CDRL2 |
| SEQ ID NO:25 | CEACAM5 binding part AC100 CDRL3 |
| SEQ ID NO:26 | CEACAM5 binding part AC117 CDRL1 |
| SEQ ID NO:27 | CEACAM5 binding part AC117 CDRL2 |
| SEQ ID NO:28 | CEACAM5 binding part AC117 CDRL3 |
| SEQ ID NO:29 | CEACAM5 binding part AC22 CDRL1 |
| SEQ ID NO:30 | CEACAM5 binding part AC22 CDRL2 |
| SEQ ID NO:31 | CEACAM5 binding part AC22 CDRL3 |
| SEQ ID NO:32 | CEACAM5 binding part light chain variable region AC82 VL |
| SEQ ID NO:33 | CEACAM5 binding part light chain variable region AC84 VL |
| SEQ ID NO:34 | CEACAM5 binding part light chain variable region AC91 VL |
| SEQ ID NO:35 | CEACAM5 binding part light chain variable region AC100 VL |
| SEQ ID NO:36 | CEACAM5 binding part light chain variable region AC117 VL |
| SEQ ID NO:37 | CEACAM5 binding part light chain AC82 VLCL |
| SEQ ID NO:38 | CEACAM5 binding part light chain AC84 VLCL |
| SEQ ID NO:39 | CEACAM5 binding part AC91 light chain VLCL |
| SEQ ID NO:40 | CEACAM5 binding part AC100 light chain VLCL |
| SEQ ID NO:41 | CEACAM5 binding part AC117 light chain VLCL |
| SEQ ID NO:42 | CEACAM5 binding part AC22 light chain VLCL |
| SEQ ID NO:43 | VK_SM3E |
| SEQ ID NO:44 | VH_SM3E |
| SEQ ID NO:45 | Primer |
| SEQ ID NO:46 | Primer |
| SEQ ID NO:47 | Primer |
| SEQ ID NO:48 | Primer |
| SEQ ID NO:49 | Primer |
| SEQ ID NO:50 | Primer |

EXAMPLES

Example 1: Cloning, Expression and Purification of Human CEACAM5; Source of huCEACAM3 and huCD47

The sequence corresponding to the complete extracellular domain (ECD) CEACAM5 were subcloned into the pEAK8 mammalian expression vector (Edge Biosystems, Gaithersburg, Md.). The vectors were modified to introduce an Avitag™ (Avidity, Denver Colo.) and a hexa-histidine tag, a human Fc region or a mouse Fc region at the C-terminus. Constructs were verified by DNA sequencing. Purification of recombinant soluble protein was carried out by IMAC (Immobilized Metal Ion Affinity Chromatography), FcXL or CaptureSelect™ IgG-Fc (ms) Affinity Matrix; Human CEACAM3 and biotinylated CEACAM3 are available from ACROBiosystems, Newark USA (Thermo Ffisher Scientific). Human CD47 and biotinylated CD47 can be produced as described in WO2019234576 or are available from ACROBiosystems, Newark USA.

Example 2: Expression and Purification of Bispecific Antibodies Carrying a Lambda and a Kappa Light Chain Simultaneous expression can be achieved in different ways such as the transfection of multiple vectors, each expressing one of the chains to be co-expressed, or by using vectors that drive expression of multiple genes. A vector pNovi κHλ was previously generated to allow for the co-expression of one heavy chain, one Kappa light chain and one Lambda light chain as described in US 2012/0184716 and WO 2012/023053, each of which is hereby incorporated by reference in its entirety. The expression of the three genes is driven by human cytomegalovirus promoters (hCMV) and the vector also contains a glutamine synthetase gene (GS) that enables the selection and establishment of stable cell lines. The VL genes of the anti-hCEACAM5 IgGλ or the anti-hCD47 IgGκ were cloned in the vector pNovi κHλ, for transient expression in mammalian cells. Peak cells or CHO cells are cultured in appropriate Flask with suitable cells number and culture medium volume (containing fetal bovine serum). Plasmid DNA is transfected into the cells using Lipofectamine 2000) according to manufacturer's instructions. Antibody concentration in the supernatant of transfected cells is measured during the production using Octet® RED96. According to antibody concentration, supernatants are harvested 5 to 7 days after transfection and clarified by centrifugation at 1300 g for 10 min. The purification process is composed of three affinity steps. First, the FcXL affinity matrix (Thermo Fisher Scientific) is washed with PBS and then added in the clarified supernatant. After incubation overnight at +4° C., supernatants are centrifuged at 2000 g for 10 min, flow through is stored and resin washed twice with PBS. Then, the resin is transferred on Amicon® Pro columns and a solution containing 50 mM glycine at pH 3.0 is used for elution. Several elution fractions are generated, pooled and desalted against PBS using 50 kDa Amicon® Ultra Centrifugal filter units (Merck KGaA, Darmstadt, Germany). The eluted product, containing total human IgGs from the supernatant, is quantified using a NanoDrop™ spectrophotometer (NanoDrop Technologies, Wilmington, Del.) and incubated for 15 min at RT and 20 rpm with the appropriate volume of Kappa select affinity matrix (GE Healthcare). Incubation, resin recovery, elution and desalting steps are performed as described previously. The last affinity purification step is performed using the lambda Fab select affinity matrix (GE Healthcare) applying the same process as for the two previous purifications. The final product is quantified using the NanoDrop™ spectrophotometer. Purified bispecific antibodies are analyzed by electrophoresis in denaturing and reducing conditions. The Agilent 2100 Bioanalyzer is used with the Protein 80 kit as described by the manufacturer (Agilent Technologies, Santa Clara, Calif., USA). 4 µL of purified samples are mixed with sample buffer supplemented with dithiothreitol (DTT; Sigma Aldrich, St. Louis, Mo.). Samples are heated at 95° C. for 5 min and then loaded on the chip. All samples are tested for endotoxin contamination using the Limulus Amebocyte Lysate test (LAL; Charles River Laboratories, Wilmington, Mass.).

Example 3: KD Measurement a) Experimental Procedure to Measure the KD of an Ab to Recombinant Human CEACAM5 (Octet®)

The affinity of the anti-human CEACAM5 arm of the CD47xCEACAM5 bispecific antibodies of the invention for recombinant soluble human CEACAM5 was determined using the Octet® Bio-Layer Interferometry (BLI) technology. An Octet® RED96 instrument and Protein A biosensors were used (Sartorius). The measurement was performed at 30° C. After hydration, pre-conditioning and a baseline step in Octet® Kinetics Buffer (PBS, 0.002% Tween 20, 0.01% BSA, Kathon; Sartorius), biosensors were loaded for 5 min with the κλ body at 0.5 µg/mL in Octet® Kinetics Buffer. Then, biosensors were dipped into a serial dilution of recombinant human CEACAM5 Extra Cellular Domain (ECD) soluble protein (produced in house), starting at 50 nM with a 2× dilution factor. The association and dissociation phases were monitored for 600 seconds each. Biosensors were regenerated using 10 mM glycine pH 1.7. A standard acquisition rate was applied (5.0 Hz, averaging by 20). Curves were processed with a reference well subtraction, a Y alignment on the baseline, without interstep correction. The affinity was measured applying a 1:1 global fitting model on the full association and dissociation steps. The binding affinity (KD) of the bispecific antibodies of the invention to recombinant human CD47 was determined by the same experimental procedure. The KD's of exemplary bispecific antibodies of the invention to CEACAM5, as determined by this procedure, are shown in Table 2 below.

b) Experimental Procedure to Measure the KD of an Ab to Recombinant Human CEACAM3 (Octet®)

The affinity of the anti-human CEACAM5 arms of the CD47xCEACAM5 bispecific antibodies of the invention for recombinant soluble human CEACAM3 was determined using the Octet® Bio-Layer Interferometry (BLI) technology and an Octet® RED96 instrument. Octet® HIS1K biosensors (Sartorius), loaded with an anti-His tag antibody, were used to capture his-tagged recombinant huCEACAM3 (R&D Systems, #9868-CM). The measurement was performed at 30° C. After hydration, pre-conditioning and a baseline step in Octet® Kinetics Buffer (PBS, 0.002% Tween 20, 0.01% BSA, Kathon; Sartorius), biosensors were loaded for 5 min with the recombinant huCEACAM3 at 5 µg/mL in Octet® Kinetics Buffer. Then, biosensors were dipped into a serial dilution of κλ bodies, starting at 667 nM with a 2× dilution factor. The association and dissociation phases were monitored for 60 seconds and 120 seconds respectively. Biosensors were regenerated using 10 mM glycine pH 1.7. A standard acquisition rate was applied (5.0 Hz, averaging by 20). Curves were processed with a double reference subtraction, a Y alignment on the baseline and an interstep correction. The affinity was measured applying a 1:1 global fitting model on the full association step and the first 5 seconds of the dissociation step. The KD's of exemplary bispecific antibodies of the invention to CEACAM3, as determined by this procedure, are shown in Table 2 below.

TABLE 2

Binding affinities (KD; nM) of the anti-CEACAM5 arm for the 3 (three) CD47xCEACAM5 bispecific antibodies, K2AC84, K2AC100, and K2AC22 (comparison) measured by Octet.

|  | Affinity to rec. hCEACAM5 (KD; nM) | Affinity to rec. hCEACAM3 (KD; nM) | Fold difference hCEACAM3/ hCEACAM5 |
|---|---|---|---|
| K2AC22 | 120 (+/−13) | 10'000 (+/−3000) | 83 |
| K2AC84 | 2.63 (+/−0.12) | 360 (+/−42) | 137 |
| K2AC100 | 4.8 (+/−1) | 700 (+/−270) | 146 |

Example 4: Epitope Binning of CD47xCEACAM5 Bispecific Antibodies by Competition with Reference Antibody SM3E Epitope binning is a competitive immunoassay used to characterize the binding of antibodies according to the invention or e.g. the alternatively the binding of the related bivalent anti-CEA (target protein) antibodies of the first binding part of the bispecific antibodies of the invention. A competitive blocking profile of a new antibody binding to the target protein is created against antibodies also binding to this target protein and for which the binding epitope has already been established/published. Competition to this reference antibody indicate that the antibody has the same or a closely located epitope and they are "binned" together. The ability of the CD47xCEACAM5 bispecific antibodies of the present invention to compete with CEACAM5 reference antibodies is tested by ELISA on recombinant human CEACAM5 with reference antibody derived from SM3E (US20050147614) carrying a mouse Fc region (mAb produced using standard methods). SM3E binds more to the N-terminal, cell membrane distal part of CEA.

Biotinylated human CEACAM5 is coated at 0.5 µg/ml in a Streptavidin-coated 96-well plate and incubated with serial dilutions of the reference mAb (from 0.09 nM to 67 nM) or an unrelated mAb carrying a mouse Fc region for 1 hour. The CD47xCEACAM5 bispecific antibodies of the present invention are added at 0.1 µg/ml for 1 hour at room temperature. The plate is washed and the bound CD47xCEACAM5 bispecific antibodies are detected with an anti-human IgG(Fc)-HRP (Jackson ImmunoResearch). After washing, the plate is revealed with Amplex™ Red reagent. The fluorescence signal is measured on a Synergy™ HT plate reader (Biotek).

Competition experiments were performed with the CD47 x CEACAM5 bispecific antibodies of the present invention. Binding of K2AC82, K2AC84, K2AC91, K2AC100, and K2AC117 were reduced by the respective competitive (i.e., tool) antibody by 80% or more. A CD47xCEACAM5 bispecific antibody is identified herein as competitive with SM3E antibody when binding of the bispecific antibody is reduced by 80% or more with the highest concentration of the reference tool antibody. A CD47xCEACAM5 bispecific antibody is identified as non-competitive with a tool antibody in case binding to CEACAM5 is reduced by less than 20% if the results with and w/o addition of a tool antibody are compared.

Example 5: Quantification of the Target Density (i.e. Number) of CEACAM5 and CD47 at the Cell Surface of 6 Different Cancer Cell Lines The target density (i.e. number) of CEACAM5 and CD47 at the cell surface of 6 different cancer cell lines was measured. The cell lines tested were human gastric adenocarcinoma cells (MKN-45, DSMZ ACC 409), human colorectal cancer cells (SK-CO-1 (ATCC; HTB-39); SNU-C1 (ATCC; CRL-5972); Ls174T (ATCC; CL-188) and LoVo (ATCC; CCL-229)), or pancreatic adenocarcinoma cells (HPAF-II, ATCC, CRL-1997).

QIFIKIT® (Agilent Dako) was used for the quantitative determination of cell surface antigens by flow cytometry using indirect immunofluorescence assay. QIFIKIT® consists of a series of 6 bead populations coated with different, but well-defined quantities of a mouse monoclonal antibody (Mab). The beads mimic cells labeled with a specific primary mouse monoclonal antibody. Different cell specimens may be labeled with different primary antibodies and then quantitated using the same set of calibration beads.

Cells were cultured in their adapted medium, detached with trypsin-EDTA (Sigma Aldrich), centrifuged (3 min, 350 g) and resuspended in cold FACS buffer (PBS, 2% BSA—from Sigma Aldrich), filtered through 0.22 µm (Stericup™, Millipore)) to obtain 3.106 cells/mL. $3.10^5$ cells of each sample was plated in a V-bottom plate. 1 µL of FcγR blocking reagent was added to each well and the plate incubated at 4° C. for 10 min. 10 µL of primary antibody against human CEACAM5 (#sc-23928; mIgG1 (Santa Cruz)) and human CD47 (internal production; B6H12; mouse backbone), at a final concentration 20 µg/mL, were added to the cells and incubated 30 min at 4° C. Cells were washed twice with 200 µL of PBS BSA 2% and centrifuged at 400 g for 3 min. 100 µL of beads (Setup or Calibration from QIFIKIT®) were washed along with the cells and treated identically. 100 µL of secondary antibody from the kit (⅕₀ in PBS BSA 2%) were added to each well and incubated for 30 to 45 min at 4° C. Cells were centrifuged (3 min, 400 g at 4° C.) to discard the supernatant and washed twice. After the last centrifugation, cells were resuspended in 130 µL of CellFix™ (BD Biosciences and acquired on CytoFlex cytometer (Beckman Coulter). Analysis was done using FlowJo™ software and Geometric means exported to an Excel file. A linear regression was performed using MFI values from the calibration beads. Antibody Binding Capacity (ABC) of cells were extrapolated from this regression line. Specific Antibody Binding Capacity (sABC) was obtained by subtracting ABC from isotype control to the one of the specific staining. Data from this analysis is presented in Table 3 below.

TABLE 3

Target density of CEACAM5 and CD47 at the cell surface of 6 cancer cell lines.

| | Origin | CEACAM5 (x10³) | CD47 (x10³) |
|---|---|---|---|
| SK-CO-1 | Colorectal | 257 | 105 |
| MKN-45 | Gastric | 155 | 135 |
| HPAF-II | Pancreas | 120 | 114 |
| SNU-Cl | Colorectal | 85 | 68 |
| Ls174T | Colorectal | 26 | 57 |
| LoVo | Colorectal | 4 | 25 |

Example 6: Measurement of the Binding of CEAxCD47 Bispecific Antibodies to CEACAM5 Expressing Cancer Cell Lines (EC50 and Maximal Binding Emax)

The binding of CD47xCEACAM5 bispecific antibodies was tested on CEACAM5-expressing human gastric adenocarcinoma cells (e.g. MKN-45), on CEACAM5-expressing human colorectal cancer cells (SK-CO-1, SNU-C1, Ls174T, and LoVo), and on CEACAM5-expressing pancreatic adenocarcinoma cells (HPAF-II).

Cells were harvested, counted, checked for viability and resuspended at $3\times10^6$ cells/ml in FACS buffer (PBS 2% BSA, 0.1% NaN3). 100 µl of the cell suspension was distributed in V-bottom 96-well plates ($3\times10^5$ cells/well). The supernatant was removed by centrifugation 3 minutes at 4° C., 1300 rpm. Increasing concentrations of the antibody according to the invention were then added into the wells and incubated for 15 minutes at 4° C. Cells were washed twice with cold FACS buffer and re-incubated for further 15 minutes at 4° C. with the PE (R-phycoerythrin)-conjugated mouse anti-human IgG Fc secondary antibody (SouthernBiotech, pre-diluted 1:100 in FACS buffer). Cells were washed twice with cold FACS buffer and resuspended in 300 µl FACS buffer with 1:15000-diluted Sytox® Blue (Life Technologies). Fluorescence, specifically mean fluorescence activity (MFI), was determined using a Cytoflex (Millipore) flow cytometer. Binding curves and EC50 and Emax values were obtained and calculated using GraphPad Prism® 7 software. Data from this analysis is presented in Table 4 below.

TABLE 4

EC50 (nM) and $E_{max}$ (MFI) binding of 6 CD47xCEACAM5 bispecific antibodies on human cancer cell lines expressing CEACAM5 and CD47 (K2AC22 comparison).

| Cell lines | | CD47xCEACAM5 bispecific antibodies | | | | | |
|---|---|---|---|---|---|---|---|
| | | K2AC22 | K2AC82 | K2AC84 | K2AC91 | K2AC100 | K2AC117 |
| SK-CO-1 | EC50 (nM) | 24 | 17.3 | 12 | 12.7 | 14.7 | 14.7 |
| | Emax (MFI*;x10⁶) | 0.52 | 0.9 | 1 | 1.3 | 0.9 | 1.1 |
| MKN-45 | EC50 (nM) | 21.3 | 10 | 7.3 | 8 | 8.7 | 8 |
| | Emax (MFI*;x10⁶) | 1.16 | 1.18 | 1.52 | 1.64 | 1.3 | 1.35 |
| HPAF-II | EC50 (nM) | 19.3 | 11.3 | 8.7 | N/A | 8 | 7.3 |
| | Emax (MFI*;x10⁶) | 0.67 | 0.94 | 1.27 | N/A | 1.1 | 1.2 |
| SNU-C1 | EC50 (nM) | 10.7 | 4.4 | 2.47 | 2.53 | 3.27 | 3.13 |
| | Emax (MFI*;x10⁶) | 0.24 | 0.28 | 0.37 | 0.4 | 0.3 | 0.37 |
| Ls174T | EC50 (nM) | 28 | 11.3 | 5.6 | 6 | 4.5 | 6.7 |
| | Emax (MFI*;x10⁶) | 0.073 | 0.077 | 0.089 | 0.1 | 0.07 | 0.07 |
| LoVo | EC50 (nM) | 44 | 22 | 16 | 16 | 18.7 | 20 |
| | Emax (MFI*;x10⁶) | 0.23 | 0.26 | 0.36 | 0.38 | 0.28 | 0.32 |

*MFI—Mean Fluorescence Intensity
N/A—Not Applicable—no available data for this Ab on this cell line The data in Table 4 show that all bispecific antibodies according to the invention show considerably lower EC50 and higher Emax compared to K2AC22.

As shown in Table 4, the bispecific antibodies according to the invention bind to SK-CO1 cells with an EC50 value of 10 to 30 nM, to MKN-45 cells with an EC50 value of 5 to 15 nM, to HPAF-II cells with an EC50 value of 5 to 15 nM, to SNU-C1 cells with an EC50 value of 1 to 10, to LS174T cells with an EC50 value of 3 to 15 nM, and/or to LoVo cells with an EC50 value of 15 to 25 nM.

Also as shown in Table 4, the bispecific antibodies according to the invention binds to SK-CO1 cells with an Emax value of 0.5 to 1.5 (MFI×10$^6$), to MKN-45 cells with an Emax value of 1 to 2 (MFI×10$^6$), to HPAF-II cells with an Emax value of 0.5 to 1.5 (MFI×10$^6$), to SNU-C1 cells with an Emax value of 0.2 to 0.6 (MFI×10$^6$), to LS174T cells with an Emax value of 0.05 to 0.2 (MFI×10$^6$), and/or to LoVo cells with an Emax value of 0.2 to 0.5 (MFI×10$^6$).

Example 7: Measurement of Phagocytosis (Phagocytosis Index) Respectively of Antibody Dependent Cellular Phagocytosis (ADCP)

The phagocytic in vitro activity of the CEACAM5×CD47 bispecific antibodies of the invention was assessed using 6 CEACAM5-expressing cancer cell lines (MKN-45, SK-CO-1, SNU-C1, Ls174T, LoVo and HPAF-II). K2AC22 was assessed for comparison using the same cell lines and experimental procedures.

The assay relies on an imaging-based method, which makes use of the CellInsight™ CX5 High Content Screening Platform. The assessed readout is the phagocytosis index, defined as the average number of target cells engulfed by 100 macrophages.

1. Preparation of the Macrophages:

Human peripheral blood mononuclear cells (PBMCs) were isolated from buffy coats, from different healthy donors (from 5 to 7 different donors, depending on the cell line), by Ficoll gradient. Macrophages were generated by culturing PBMCs for 7 to 9 days in complete medium (RPMI 1640, 10% heat-inactivated fetal calf serum [Invitrogen]), 2 mM L-glutamine, 1 mM sodium pyruvate, 10 mM HEPES buffer, 25 mg/mL gentamicin (all from Sigma-Aldrich), and 50 mM 2-mercaptoethanol (Thermo Fisher Scientific)) in the presence of 20 ng/mL of human macrophage colony-stimulating factor (M-CSF) (PeproTech). Non-adherent cells were subsequently eliminated in the differentiation phase (day+1) by exchanging the cell culture medium, and adherent cells representing macrophages were detached using cell dissociation buffer (Sigma-Aldrich) and washed in complete medium the day of use (day 7, day 8, or day 9) for ADCP experiment based on cytometry. For ADCP based on cell imaging, macrophages were detached at day 6 using cell dissociation buffer and seeded at 30'000 per well in 96 optical plate (Costar®).

2. Assessment of the Phagocytosis Activity (CellInsight™ Based Assay)

Macrophages (stained with calcein red orange) adhering to microplate wells were co-incubated with Calcein AM-labeled target tumor cells at an effector:target cells ratio of 1:3 for 30 min (MKN45 and SNU-C1) or 2.5 hours (LoVo and Ls174T) at 37 degree C. in the presence of different concentrations of the tested antibodies. At the end of the incubation period, supernatants were replaced by complete culture medium and the microplates were imaged with the CellInsight™ CX5 High Content Screening Platform. 1500 macrophages were acquired and analyzed per well. Phagocytosis was evidenced as double-positive events (macrophage+target tumor cell) and the phagocytosis indexes were calculated by the CellInsight™ manufacturer's software.

All the results shown in FIG. 2 and Tables 5, 6, 7, 8, 9 were obtained with 4 CEACAM5-expressing cancer cell lines (MKN-45, SNU-C1, Ls174T, LoVo); with an effector cell to target/tumor cell ratio of 1:3.

TABLE 5

Percentage of increase in the maximum of phagocytosis index assessed for 5 CEACAM5×CD47 bispecific antibodies in comparison to bispecific Ab K2AC22.

|  | CEACAM5 levels | K2AC82 | K2AC84 | K2AC91 | K2AC100 | K2AC117 |
|---|---|---|---|---|---|---|
| MKN-45 | 155,000 | 6.1 | 1.8 | 4.6 | 1.8 | 0 |
| SNU-C1 | 85,000 | 0 | 0 | 0 | 0 | 0 |
| Ls174T | 26,000 | 8.7 | 14.4 | 20.6 | 14.4 | 11.2 |
| LoVo | 4,000 | 13.2 | 17 | 9.3 | 18.6 | 8.5 |

All five bispecific antibodies according to the invention showed better binding compared to K2AC22 (lower EC50 and higher Emax, see Example 6, Table 4). Surprisingly the percent increase of the maximal achieved phagocytosis index Emax ADCP of the antibodies of the invention compared to K2AC22 was strongest in the low CEACAM5 expressing cell lines LoVo and Ls174T.

These results were obtained in experiments using macrophages obtained from different human donors. The data obtained from such experiments are shown in Table 6 (for MKN-45 cells), Table 7 (for SNU-C1 cells), in Table 8 (for Ls174T cells) and Table 9 (for LoVo cells).

TABLE 6

In vitro assessment of EC50 (μg/mL) and E$_{max}$ from phagocytosis activity 6 CEACAM5xCD47 bispecific antibodies (K2AC82, K2AC84, K2AC91, K2AC100, K2AC117, and K2AC22 (comparison)) using MKN-45 human cancer cell line as target with 7 different donors (D) of macrophages.

| Donors (D) | | CD47xCEACAM5 bispecific antibodies | | | | | |
| --- | --- | --- | --- | --- | --- | --- | --- |
| | | K2AC22 | K2AC82 | K2AC84 | K2AC91 | K2AC100 | K2AC117 |
| D854 | EC50 (μg/mL) | 0.2 | 0.14 | 0.1 | 0.04 | 0.3 | 0.1 |
| | Max index of phagocytosis | 57 | 61 | 47 | 45 | 53 | 48 |
| D860 | EC50 (μg/mL) | 0.2 | 0.13 | 0.25 | 0.23 | 0.25 | 0.36 |
| | Max index of phagocytosis | 41 | 47 | 40 | 50 | 47 | 41 |
| D864 | EC50 (μg/mL) | 0.82 | 0.42 | 0.28 | 0.25 | 0.53 | 0.34 |
| | Max index of phagocytosis | 54 | 71 | 67 | 66 | 67 | 67 |
| D867 | EC50 (μg/mL) | 0.5 | 0.15 | 0.21 | 0.13 | 0.21 | 0.2 |
| | Max index of phagocytosis | 62 | 60 | 64 | 65 | 60 | 62 |
| D868 | EC50 (μg/mL) | 0.65 | 0.19 | 0.64 | 0.3 | 0.16 | 0.26 |
| | Max index of phagocytosis | 31 | 30 | 38 | 36 | 33 | 31 |
| D870 | EC50 (μg/mL) | 0.35 | 0.17 | 0.14 | 0.35 | 0.1 | 0.12 |
| | Max index of phagocytosis | 40 | 37 | 36 | 38 | 32 | 34 |
| D871 | EC50 (μg/mL) | 0.4 | 0.15 | 0.14 | 0.2 | 0.2 | 0.2 |
| | Max index of phagocytosis | 41 | 40 | 40 | 41 | 40 | 40 |
| Mean (+/−SD) | EC50 | 0.45 (+/−0.2) | 0.19 (+/−0.1) | 0.25 (+/−0.2) | 0.21 (+/−0.1) | 0.25 (+/−0.1) | 0.23 (+/−0.1) |
| | Max index of phagocytosis | 46.6 (+/−11) | 49.4 (+/−15) | 47.4 (+/−15) | 48.7 (+/−12) | 47.4 (+/−13) | 46.1 (+/−14) |

TABLE 7

In vitro assessment of EC50 and Emax from phagocytosis activity 6 CEACAM5xCD47 bispecific antibodies (K2AC82, K2AC84, K2AC91, K2AC100 & K2AC117, and K2AC22) using SNU-C1 human cancer cell line as target with 5 different donors (D) of macrophages.

| Donors (D) | | CD47xCEACAM5 bispecific antibodies | | | | | |
| --- | --- | --- | --- | --- | --- | --- | --- |
| | | K2AC22 | K2AC82 | K2AC84 | K2AC91 | K2AC100 | K2AC117 |
| D860 | EC50 (μg/mL) | 0.02 | 0.05 | 0.02 | 0.003 | 0.02 | 0.02 |
| | Max index of phagocytosis | 26 | 22 | 22 | 17 | 22 | 20 |
| D868 | EC50 (μg/mL) | 0.6 | 0.08 | 0.35 | 0.09 | 0.3 | 0.2 |
| | Max index of phagocytosis | 20 | 17 | 22 | 19 | 21 | 19 |
| D870 | EC50 (μg/mL) | 0.07 | 0.13 | 0.06 | 0.05 | 0.07 | 0.06 |
| | Max index of phagocytosis | 14 | 15 | 13 | 13 | 14 | 14 |
| D871 | EC50 (μg/mL) | 0.96 | 0.2 | 0.18 | 0.27 | 1.28 | 0.38 |
| | Max index of phagocytosis | 17 | 15 | 15 | 17 | 17 | 17 |
| D875 | EC50 (μg/mL) | 0.18 | 0.12 | 0.15 | 0.06 | 0.08 | 0.08 |
| | Max index of phagocytosis | 22 | 16 | 16 | 15 | 16 | 14 |
| Mean (+/−SD) | EC50 | 0.37 (+/−0.4) | 0.12 (+/−0.06) | 0.15 (+/−0.13) | 0.09 (+/−0.1) | 0.35 (+/−0.53) | 0.15 (+/−0.15) |
| | Max index of phagocytosis | 19.8 (+/−4.6) | 17 (+/−2.9) | 17.6 (+/−4.2) | 16.2 (+/−2.3) | 18 (+/−3.4) | 16.8 (+/−2.8) |

TABLE 8

EC50 and $E_{max}$ phagocytosis activity of 6 CD47xCEACAM5 bispecific antibodies on Ls174T human cancer cell line with 5 different donors of macrophages.

| | | CD47xCEACAM5 bispecific antibodies | | | | | |
|---|---|---|---|---|---|---|---|
| Donors (D) | | K2AC22 | K2AC82 | K2AC84 | K2AC91 | K2AC100 | K2AC117 |
| D862 | EC50 (µg/mL) | 0.25 | 0.17 | 0.29 | 0.84 | 0.56 | 0.22 |
| | Max index of phagocytosis | 37 | 44 | 47 | 45 | 46 | 41 |
| D863 | EC50 (µg/mL) | N/A | N/A | N/A | N/A | N/A | N/A |
| | Max index of phagocytosis | 32 | 40 | 40 | 37 | 40 | 41 |
| D866 | EC50 (µg/mL) | 1.57 | 0.15 | N/A | N/A | 0.07 | 0.48 |
| | Max index of phagocytosis | 15 | 14 | 19 | 29 | 14 | 16 |
| D874 | EC50 (µg/mL) | 0.33 | 0.04 | 0.03 | 0.03 | 0.05 | 0.09 |
| | Max index of phagocytosis | 51 | 44 | 47 | 47 | 48 | 50 |
| D875 | EC50 (µg/mL) | 0.25 | 0.19 | 0.098 | 0.45 | 0.35 | 0.15 |
| | Max index of phagocytosis | 25 | 32 | 30 | 35 | 35 | 30 |
| Mean (+/−SD) | EC50 | 0.6 (+/−0.65) | 0.14 (+/−0.07) | 0.14 (+/−0.13) | 0.44 (+/−0.41) | 0.26 (+/−0.24) | 0.24 (+/−0.17) |
| | Max index of phagocytosis | 32 (+/−13.5) | 34.8 (+/−12.6) | 36.6 (+/−12.1) | 36.8 (+/−7.4) | 36.6 (+/−13.6) | 35.6 (+/−13) |

TABLE 9

EC50 and $E_{max}$ phagocytosis activity of 6 CD47xCEACAM5 bispecific antibodies on LoVo human cancer cell line with 6 different donors of macrophages.

| | | CD47xCEACAM5 bispecific antibodies | | | | | |
|---|---|---|---|---|---|---|---|
| Donors (D) | | K2AC22 | K2AC82 | K2AC84 | K2AC91 | K2AC100 | K2AC117 |
| D862 | EC50 (µg/mL) | 0.14 | 0.05 | 0.05 | 0.045 | 0.054 | 0.31 |
| | Max index of phagocytosis | 30 | 27 | 27 | 26 | 27 | 28 |
| D863 | EC50 (µg/mL) | 0.28 | 0.12 | 0.3 | 0.09 | 0.37 | 0.19 |
| | Max index of phagocytosis | 19 | 28 | 31 | 30 | 30 | 27 |
| D866 | EC50 (µg/mL) | 0.24 | 0.054 | 0.042 | 0.044 | 0.08 | 0.07 |
| | Max index of phagocytosis | 29 | 31 | 31 | 34 | 34 | 34 |
| D872 | EC50 (µg/mL) | 1.14 | 5.6 | 3 | 0.65 | 2.34 | 2.43 |
| | Max index of phagocytosis | 10 | 17 | 17 | 10 | 13 | 13 |
| D873 | EC50 (µg/mL) | N/A | N/A | N/A | N/A | N/A | N/A |
| | Max index of phagocytosis | 11 | 12 | 13 | 10 | 17 | 8 |
| D874 | EC50 (µg/mL) | 0.14 | 0.05 | 0.036 | 0.054 | 0.052 | 0.038 |
| | Max index of phagocytosis | 30 | 31 | 32 | 31 | 32 | 30 |
| Mean (+/−SD) | EC50 | 0.39 (+/−0.42) | 1.17 (+/−2.47) | 0.69 (+/−1.3) | 0.18 (+/−0.27) | 0.58 (+/−1) | 0.61 (+/−1) |
| | Max index of phagocytosis | 21.5 (+/−9.5) | 24.3 (+/−7.9) | 25.2 (+/−8.2) | 23.5 (+/−10.8) | 25.5 (+/−8.5) | 23.3 (+/−10.3) |

Example 8: Measurement of the Competition for Binding to CEACAM5 Between the Bispecific Antibodies of the Invention and Other Therapeutic Antibodies Binding to CEACAM5

A binding assay to cells expressing CEACAM5 was performed as described in Example 6. This assay can be used to measure the shift of the binding curve of the bispecific antibodies of the invention to MKN-45 and LS174T cancer cell lines if CEAxCD3 bispecific antibodies like cibisatamab or TCB2014 are added to the binding assay. An antibody was regarded as non-competitive if 300 nM of the antibody shifts the binding curve of a bispecific antibody of the invention by less than a factor of 3.

Figure 5:
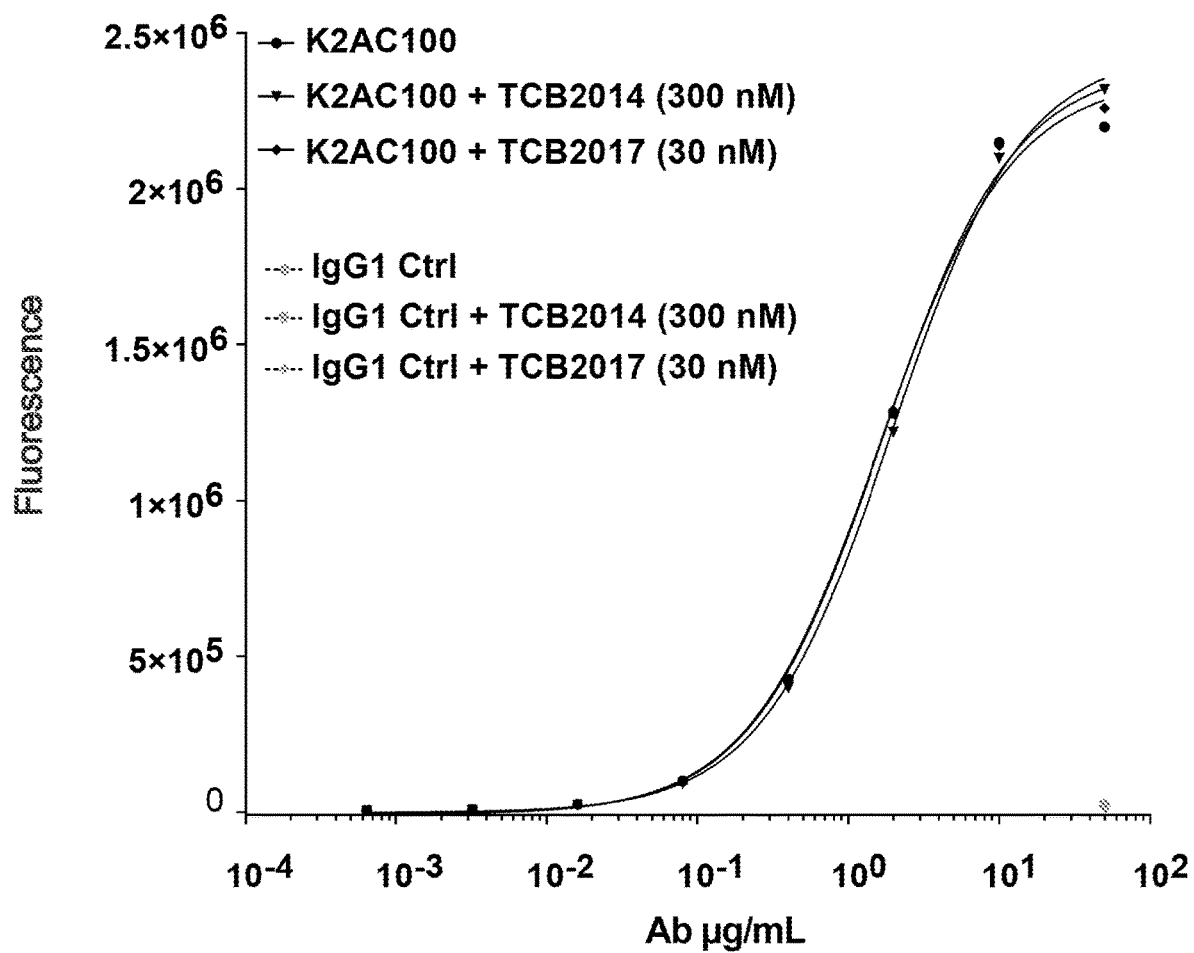
FIG. 5. Concentration dependent binding of CD47xCEACAM5 bispecific antibody K2AC100 in presence of anti-CEACAM5 mAbs, TCB2014 and TCB 2017, at the cell surface of CEACAM5-expressing cells, MKN-45. K2AC100 was directly labeled with a fluorochrome to follow its binding on MKN-45 cells alone (dark line, dark circles), in presence of 300 nM of TCB2014 (dark line, dark triangles) or 30 nM of TCB2017 (dark line, black diamonds). Negative controls (Ctrl) were used (IgG1 in presence of TCB2014 or TCB2017).

In this experiment, the concentration-dependent binding of CD47xCEACAM5 bispecific antibody K2AC100 was measured in the presence of an anti-CEACAM5 mAbs, either TCB2014 or TCB 2017. This binding was measured at the cell surface of CEACAM5-expressing MKN-45 cells. K2AC100 was directly labeled with a fluorochrome to follow its binding on MKN-45 cells alone (dark line, dark circles), in presence of 300 nM of TCB2014 (dark line, dark triangles) or 30 nM of TCB2017 (dark line, black diamonds). Negative controls (Ctrl) were used (IgG1 in presence of TCB2014 or TCB2017). The results of this experiment are shown in FIG. 5. These data show that there was no or minimal shift of the binding curve of the CEAxCD47 bispecific antibody K2AC100 of this invention to MKN-45 tumor cells if 300 nM of TCB2014 are added. Therefore, the K2AC100 antibody is non-competitive with the TCB2014 and TCB2017 antibodies with respect to CEACAM5 binding.

Example 9: Production of Afucosylated Bispecific Antibodies of the Invention Tables 10 and 11 show the results for the phagocytosis of two cell lines (MKN-45 and SNU-C1) by afucosylated versions of the bispecific antibodies of the invention (EC50 and Emax). The afucosylated versions of the bispecific antibodies of the invention were produced and purified by the following methods:

1. Production

CHO pool transfected with the plasmid for the respective bispecific antibody of the invention (for vectors respectively plasmids see Example 2) was inoculated at a viable cell concentration of $0.3 \times 10^6$ cells/mL in a Thomson erlen device with a working volume of 700 mL or 100 mL for the production of fucosylated and afucosylated antibodies, respectively. All the pools were operated in a 15 days duration fed-batch mode using CDACF medium CDCHO and an adapted feeding regime. For the production of afucosylated antibodies, bolus of 200 µM fucose inhibitor (1,3,4-Tri-O-acetyl-2-deoxy-2-fluoro-L-fucose) were added at day 0, 5, 8 and 11 during the fed batch process based on afucosylation strategy described by Rillahan et al. Nature Chem. Biol. 2012 July; 8(7):661-8 and based on EP2282773. Harvest of the bispecific antibodies of the invention pools supernatants containing fucosylated or afucosylated antibodies was performed after 15 days of Fed batch culture. Harvests of CHO pools supernatants was clarified using the Sartoclear Dynamics® Lab V Cell Harvesting Sartorius system (see supplier instructions).

2. Purification

Purification of fucosylated and afucosylated bispecific antibodies of the invention was accomplished by a three-step affinity purification process. Before starting purification, antibody concentration in the supernatant of bispecific antibody pools was measured using Octet® RED96 in order to use columns with appropriate volume of affinity matrix. Each clarified CHO pool supernatant containing fucosylated or afucosylated bispecific antibodies was loaded onto a MabSelect SuRe™ (MSS) column (GE Healthcare) without prior adjustment, to remove a major part of cell culture contaminants. The MSS eluate was then treated by low pH hold to inactivate viruses, and neutralized at pH 6 with Tris 1M pH9. The MSS eluate was then loaded onto the Lambda-FabSelect (LFS) column (GE Healthcare) to remove monospecific κ (mono κ). The LFS eluate was then pH adjusted at pH 6. The LFS was loaded onto the Capto™ L (CL) column (GE Healthcare) to remove monospecific λ (mono λ). The CL Eluate was pH adjusted before storage. The final material was then concentrated and diafiltered into the final formulation buffer, with its concentration adjusted using the NanoDrop™ spectrophotometer. Fucosylated and afucosylated bispecific antibodies were aliquoted and stored at −80° C. until delivery. Purified bispecific antibodies were analyzed for sizing by electrophoresis in denaturing and reducing conditions with the Agilent 2100 Bioanalyzer using the Protein 80 kit as described by the manufacturer (Agilent Technologies, Santa Clara, Calif., USA). Aggregation level was assessed by size exclusion chromatography (SEC-UPLC) using the ACQUITY UPLC H-Class Bio System (Waters). Charge variant analysis of purified bispecific antibodies was achieved by isoelectric focusing technique (IEF) using the Multiphor™ II Electrophoresis System (GE Healthcare). The relative distribution of N-linked complex biantennary glycoforms of fucosylated and afucosylated K2AC5 and K2AC22 antibodies was determined using the throughput microchip-CE method on the LabChip® GXII Touch (Perkin Elmer). All antibodies were tested for endotoxin contamination using the Limulus Amebocyte Lysate test (LAL; Charles River Laboratories, Wilmington, Mass.). The afuc bispecific antibodies of the invention showed afucosylation of >70%.

Figure 3A:
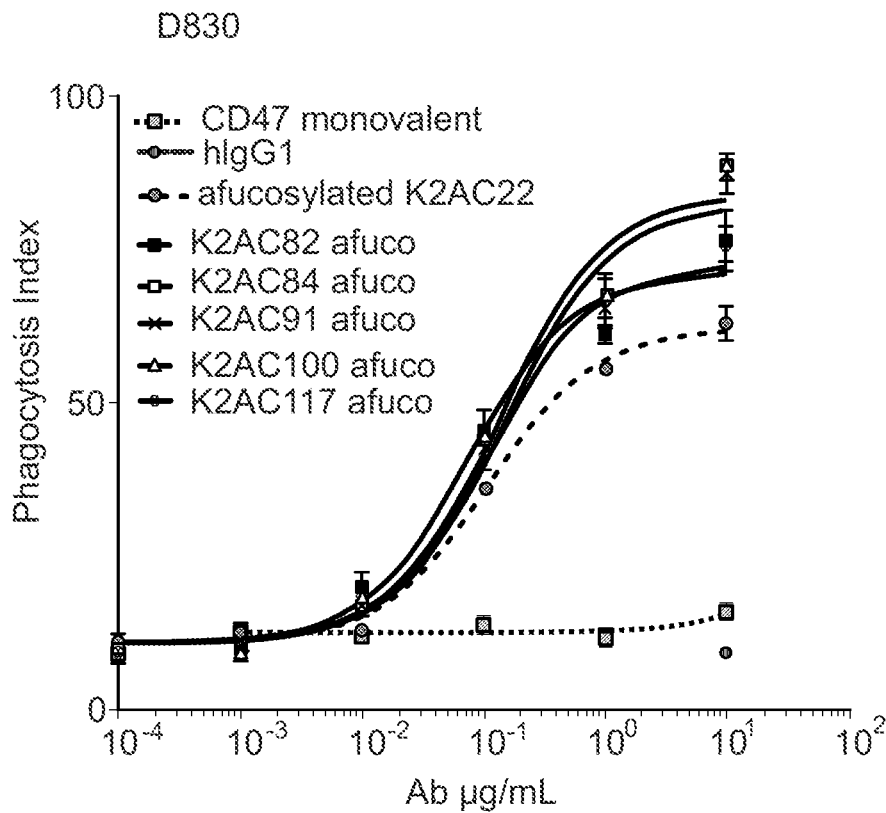
FIGS. 3A-3B. Concentration dependent phagocytosis of CEACAM5-expressing cancer cells induced by four to five afucosylated CEACAM5xCD47 bispecific antibodies according to the invention (K2AC82 afuco, K2AC84 afuco, K2AC91 afuco, K2AC100 afuco and K2AC177 afuco) as compared to the state of the art afucosylated CEACAM5xCD47 bispecific antibody K2AC22. These figures also show the phagocytosis induced by the corresponding anti-CD47 monovalent antibody and a hIgG1 isotype control (hIgG1).
Figure 3A:
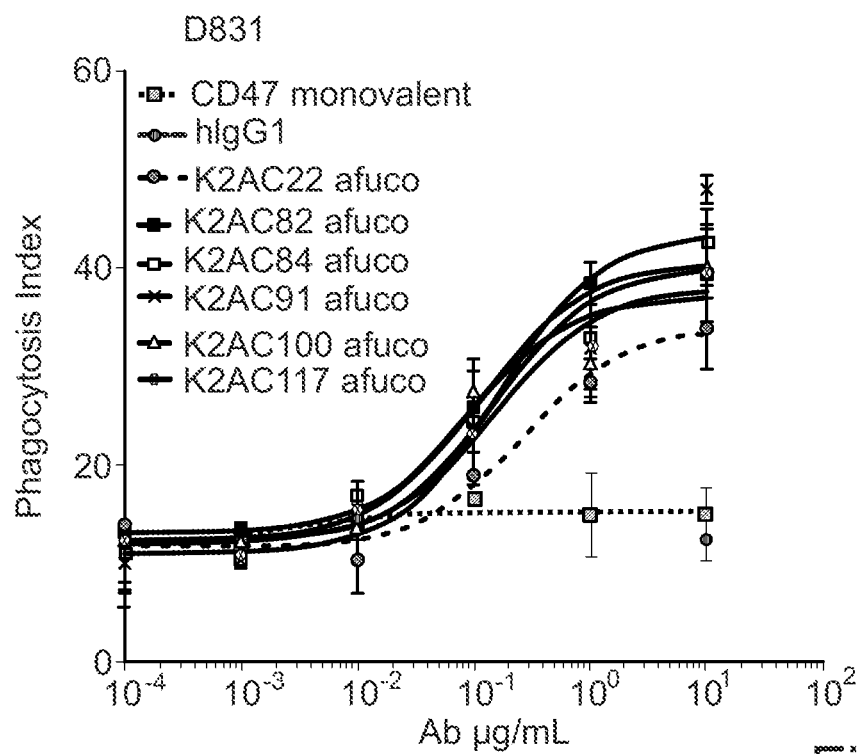
Figure 3B:
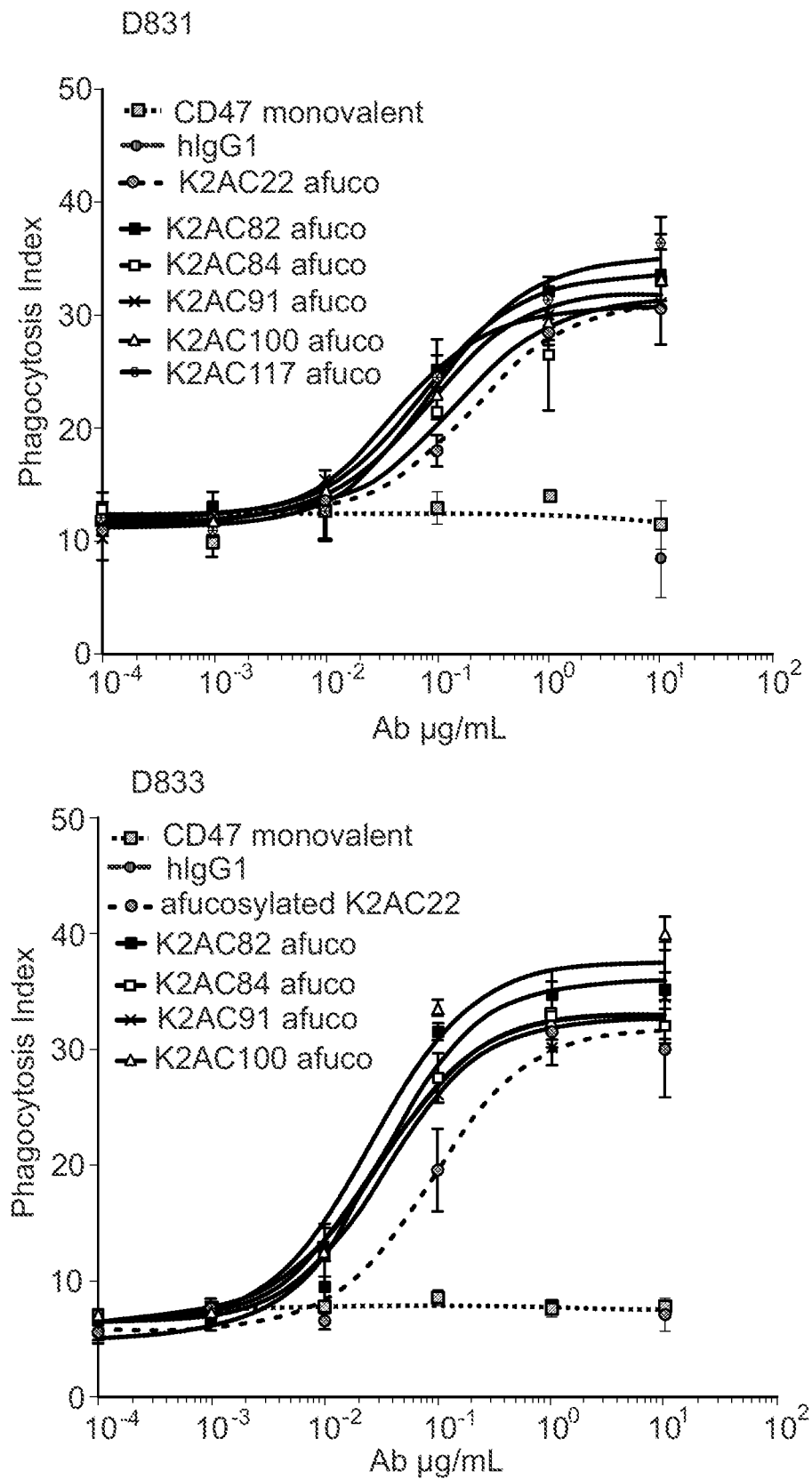

These afucosylated CEAxCD47 bispecific antibodies were used to obtain the results shown in Tables 10 and 11 and in FIGS. 3A and 3B.

3. Other Methods to Produce Afucosylated Bispecific Antibodies of the Invention 3.1 By Using FUT 8 Negative Production Cell Line Alternatively, and according to the knowledge of the inventors, afucosylated bispecific antibodies according to the invention can be produced also according to the method as follows:

Material and Methods are according to Naoko Yamane-Ohnuki et al., Biotech. Bioeng.; 87 (2004) 614-622.

Isolation of Chinese Hamster FUT8 cDNA

According to the knowledge of the inventors, total RNA is isolated from CHO/DG44 cells using the RNeasy® Mini Kit (Qiagen, Hilden, Germany) and reverse transcribed with oligo-dT using a Superscript™ first-strand synthesis system for reverse transcript-polymerase chain reaction (RT-PCR) (Invitrogen, Carlsbad, Calif.). A Chinese hamster FUT8 cDNA is amplified from single-stranded CHO/DG44 cell cDNAs by PCR using primers

```
                                              (SEQ ID NO: 45)
5V-GTCTGAAGCATTATGTGTTGAAGC-3V
and (SEQ ID NO: 46)
5V-GTGAGTACATTCATTGTACTGTG-3V, designed from the murine FUT8 cDNA
(Hayashi, 2000; DNA Seq 11:91-96).
```

Targeting Construct of FUT8 Locus

According to the knowledge of the inventors, the targeted disruption of the FUT8 gene in CHO/DG44 cells is carried out using two replacement vectors, pKOFUT8Neo and pKOFUT8Puro. The 9.0-kb fragment of the FUT8 gene including the first coding exon is isolated by screening the CHO-K1 cell E-genomic library (Stratagene, La Jolla, Calif.) with the Chinese hamster FUT8 cDNA as a probe to establish the targeting constructs. A 234-bp segment containing the translation initiation site is replaced with the neomycin-resistance gene (Neor) cassette or the puromycin-resistance gene (Puror) cassette from plasmid pKOSelect-Neo or pKOSelectPuro (Lexicon, Tex.), respectively, flanked by loxP sites. The diphtheria toxin gene (DT) cassette from plasmid pKOSelectDT (Lexicon) is inserted at the 5V homologous region. The resulting targeting constructs, pKOFUT8Neo and pKOFUT8Puro, included the 1.5-kb 5V homologous sequence and the 5.3-kb 3V homologous sequence. Before transfection, the targeting constructs are linearized at a unique SalI site.

Transfection and Screening for Homologous Recombinants

According to the knowledge of the inventors, subconfluent CHO/DG44 cells (1.6 106) are electroporated with 4 Ag of linearized pKOFUT8Neo at 350 V and 250 AF using a Bio-Rad GenePulser® II. After electroporation, transfectants are selected with 600 Ag/mL G418 (Nacalai Tesque, Kyoto, Japan). Genomic PCR is performed in 96-well plates by the modified microextraction method reported previously (Ramirez-Solis et al., 1992; Anal Biochem 201:331-335.) using the following primers:

```
                                              (SEQ ID NO: 47)
5V-TTGTGTGACTCTTAACTCTCAGAG-3V
and (SEQ ID NO: 48)
5V-GAGGCCACTTGTGTAGCGCCAAGTG-3V.
```

Homologous recombinants are identified by the 1.7-kb fragment obtained using genomic PCR and confirmed by Southern blot analysis using the 221-bp fragment amplified with the following primers:

```
                                              (SEQ ID NO: 49)
5V-GTGAGTCCATGGCTGTCACTG-3V
and (SEQ ID NO: 50)
5V-CCTGACTTGGCTATTCTCAG-3V.
```

The hemizygous clone is subject to a second round of homologous recombination using linearized pKOFUT8Puro and drug selection with 15 Ag/mL puromycin (Sigma-Aldrich, St. Louis, Mo.) as described earlier. The identified homozygous disruptants are electroporated with the Cre-recombinase expression vector pBS185 (Invitrogen) to remove drug-resistance gene cassettes from both FUT8 alleles.

Monoclonal Antibody Production by FUT8(−) Cells

According to the knowledge of the inventors, FUT8(−) cell lines are electroporated with an expression vector encoding a bispecific antibody according to the invention and selected in media lacking hypoxanthine and thymidine. The confluent transfectants are cultured in Ex-Cell® 301 Medium (JRH Biosciences, Lenexa, Kans.) for 1 week. The antibody is purified from culture supernatants using Mab-Select™ (Amersham Biosciences, Piscataway, N.J.). Further purification steps can be anion/cation exchange chromatography, size exclusion chromatography and especially purification using kappa respectively lambda selective resins as described above.

3.2. By Retrieval of Extracellular Fucose from Production Cell Medium Plus Enzymatic Intervention with the Intracellular Fucose Biosynthesis Preferably, and according to the knowledge of the inventors, afucosylated bispecific antibodies of the invention can be produced also according to the method/technology as follows and described in, U.S. Pat. No. 8,642,292. This technology is designed to configure the stable integration of a heterologous bacterial enzyme into an antibody producer cell line like a CHO cell line or others. By this, the de novo synthesis of fucose from D-mannose is blocked. If in addition production cells are cultivated in fucose free medium, as a result antibodies with a stable level of afucosylation are produced.

In eukaryotic cells fucose is generated through two routes, a) from the extracellular space or lysosome through the salvage pathway and b) by de novo synthesis of fucose from D-mannose in the de novo synthesis pathway of fucose.

The salvage pathway can be completely blocked by omission of fucose from the culture medium. The de novo biosynthesis pathway can be blocked by converting the intermediate GDP-4-keto-6-deoxy-D-mannose of this pathway to GDP-D-rhamnose instead of GDP-4-keto-6-deoxy-D-galactose. This is achieved by bringing the bacterial enzyme GDP-6-deoxy-D-lyxo-4-hexulose reductase (RMD) into the production cell line, respectively by stable integration of the gene encoding for RMD into the production cell line. Even rather low amounts of RMD expressed in the production cell line completely block the de novo synthesis pathway of the production cell.

This technology will be used to construct production cell lines, e.g. CHO based cell lines, designed for the production of afucosylated antibodies of the invention as well as to existing production cell lines which already produce antibodies of the invention and are engineered to produce the antibodies with fucose content reduced by 80% to 100%.

All the results shown in FIGS. 3A and 3B and Tables 10 and 11 were obtained with 2 CEACAM5-expressing cancer cell lines (MKN-45 and SNU-C1); with an effector cell to target/tumor cell ratio of 1:3. These results were obtained in experiments using macrophages obtained from three different human donors. The data obtained from such experiments are shown in Table 10 (for MKN-45 cells) and Table 11 (for SNU-C1 cells).

TABLE 10

In vitro assessment of EC50 (µg/mL) and $E_{max}$ (max index of phagocytosis) from phagocytosis activity 6 afucosylated CEACAM5xCD47 bispecific antibodies (K2AC82 afuco, K2AC84 afuco, K2AC91 afuco, K2AC100 afuco, K2AC117 afuco, and K2AC22 afuco (comparison)) using MKN45 human cancer cell line as target with 2 different donors (D) of macrophages.

| | | CD47xCEACAM5 bispecific antibodies | | | | | |
|---|---|---|---|---|---|---|---|
| Donors (D) | | K2AC22 afuco | K2AC82 afuco | K2AC84 afuco | K2AC91 afuco | K2AC100 afuco | K2AC117 afuco |
| D830 | EC50 (µg/mL) | 0.11 | 0.077 | 0.13 | 0.15 | 0.14 | 0.11 |
| | Max index of phagocytosis | 62 | 72 | 84 | 82 | 84 | 72 |
| D831 | EC50 (µg/mL) | 0.26 | 0.12 | 0.14 | 0.16 | 0.08 | 0.15 |
| | Max index of phagocytosis | 34 | 40 | 40 | 44 | 37 | 38 |
| Mean (+/−SD) | EC50 | 0.2 (+/−0.11) | 0.1 (+/−0.03) | 0.1 (+/−0.01) | 0.2 (+/−0.01) | 0.1 (+/−0.04) | 0.1 (+/−0.03) |
| | Max index of phagocytosis | 48 (+/−19.8) | 56 (+/−22.6) | 62 (+/−31.1) | 63 (+/−26.9) | 60.5 (+/−33) | 55 (+/−24) |

TABLE 11

In vitro assessment of EC50 (µg/mL) and $E_{max}$ from phagocytosis activity 6 afucosylated CEACAM5xCD47 bispecific antibodies (K2AC82 afuco, K2AC84 afuco, K2AC91 afuco, K2AC100 afuco, K2AC117 afuco, and K2AC22 afuco (comparison)) using SNU-C1 human cancer cell line as target with 2 different donors (D) of macrophages.

| | | CD47xCEACAM5 bispecific antibodies | | | | | |
|---|---|---|---|---|---|---|---|
| Donors (D) | | K2AC22 afuco | K2AC82 afuco | K2AC84 afuco | K2AC91 afuco | K2AC100 afuco | K2AC117 afuco |
| D831 | EC50 (µg/mL) | 0.2 | 0.07 | 0.14 | 0.04 | 0.08 | 0.09 |
| | Max index of phagocytosis | 31 | 34 | 31 | 31 | 32 | 35 |
| D833 | EC50 (µg/mL) | 0.09 | 0.03 | 0.03 | 0.034 | 0.027 | N/A |
| | Max index of phagocytosis | 32 | 36 | 33 | 33 | 38 | N/A |
| Mean (+/−SD) | EC50 | 0.15 (+/−0.08) | 0.05 (+/−0.03) | 0.09 (+/−0.08) | 0.04 (+/−0.004) | 0.05 (+/−0.04) | 0.09 |
| | Max index of phagocytosis | 31.5 (+/−0.7) | 35 (+/−1.4) | 32 (+/−1.4) | 32 (+/−1.4) | 35 (+/−4.2) | 35 |

Example 10

Blocking the Interaction of SIRPα with CD47 on Tumor Cells

Experimental set-up for the measurement of the SIRPα inhibition potency (IC50) of the bispecific antibodies of this invention:

The cell-based assay monitoring the interaction of soluble SIRPα with human CD47 expressed at the surface of MKN-45 cells as described below was used for the detection of the blocking activity. Concentration-response experiments with bispecific antibodies according to the invention allowed determination of inhibition curves (see FIG. 4) and of IC50 values (see Table 12).

MKN-45 cancer cells, expressing both CD47 and CEACAM5, were stained with CFSE violet to allow the imaging system (CX5) to detect the cells. Briefly, 3'000 stained MKN-45 cells per well were seeded in a 384 optical well plate (Costar®) and incubated for 50 minutes with increased concentrations of bispecific antibodies of the invention (1.9 pM to 333 nM, in quadruplicates). Then, a fixed concentration of SIRPα-mouseFc premixed with anti-mouse IgG-Fc Alexa Fluor™ 647 coupled antibody (Jackson Immunoresearch diluted 1:2000) was added at 50 ng/mL final. After an incubation of 3 hours and 30 minutes, images of the fluorescence signals emitted by the detected bound SIRPα on the plates were acquired with the imaging system (CX5, Thermo Fisher). Fluorescence signals (mean fluorescence intensity MFI) were plotted according to the dose range tested, and IC50 was calculated by the software (GraphPad Prism®). Results are shown in Table 12:

TABLE 12

IC50 (nM) measured with the CD47/SIRPα blocking assay for 5 CEACAM5 × CD47 bispecific antibodies of the present invention (K2AC82, K2AC84, K2AC91, K2AC100 and K2AC117) as compared to state of the art bispecific CEA × CD47 antibody K2AC22 (using MKN-45 as hCD47-expressing cells).

| Antibody name | SIRPα inhibition potency (nM)[#] |
|---|---|
| K2AC22 | 1.2 |
| K2AC82 | 0.07 |
| K2AC84 | 0.04 |
| K2AC91 | 0.05 |
| K2AC100 | 0.09 |
| K2AC117 | 0.08 |

Example 11: Organoid Procedure to a. Obtain CEACAM5 Expression in Cancer Cells from Fresh Samples from Cancer Patients (Qifikit Data) and b. To Obtain Phagocytosis Data Organoids derived from primary samples of patients were prepared as single cell suspension by standard methods (enzymatic digestion and/or mechanical dissociation). 10 µL of anti-human CEACAM5 primary antibody ((#sc-23928; mIgG1 (Santa Cruz); final concentration 20 µg/mL) were added to the cells and incubated 30 min at 4° C. Cells were washed, and centrifuged. 100 µL of beads (Setup or Calibration from QIFIKIT®) were washed along with the cells and treated identically. 100 µL of secondary antibody from the kit (1/50 in PBS BSA 2%) were added to each well and incubated for 30 to 45 min at 4° C. Cells were centrifuged to discard the supernatant and washed twice. After the last centrifugation, cells were resuspended acquired on a cytometer. Analysis was done using specific software and Geometric means exported to an Excel file. A linear regression was performed using MFI values from the calibration beads. Antibody Binding Capacity (ABC) of cells were extrapolated from this regression line. Specific Antibody Binding Capacity (sABC) was obtained by subtracting ABC from isotype control to the one of the specific staining.

The average expression of CEACAM5 of these primary organoids has been found to be 28,000 CEACAM5 targets per cell, i.e. a factor of approximately 4-fold lower than average expression on the cell lines in Table 5.

The organoids derived from primary samples of cancer patients can also be used to study concentration dependent phagocytosis/phagocytosis index if bispecific antibodies of the invention and macrophages from human donors are added (see Example 7). By using the same methods, according to the knowledge of the inventors, also combinations of the bispecific antibodies of the invention with CEAxCD3 bispecific antibodies can be studied if also T-cells from human donors are added.

Example 12: Anti-Tumor Activity: Tissue Slice Cultures

According to the knowledge of the inventors, anti-tumor activity of a bispecific antibody according to the invention can be evaluated as single agent as well as in combination treatment, respectively, in tumor tissue slice cultures (see Sonnichsen et al., Clinical Colorectal Cancer 2018) from patients diagnosed with CEA-expressing tumors.

1. Tissue Slice Culture and Treatment

Fresh tumor tissue samples are cut and handled as previously published (Sonnichsen et al., Clinical Colorectal Cancer 2018). In brief, immediately after surgical resection and first macroscopic pathologic assessment, tumor samples are cut into slices of 350 µm using a tissue chopper. Tissue slice diameter is then standardized by using a 3-mm coring tool. Three tissue slices are randomly pooled, placed on membrane inserts, and cultivated in 6-well plates. Slices are incubated under standardized conditions of 37° C. and 5% CO2. After pre-cultivation in standard cell culture medium, slice triplets are exposed to bispecific antibodies according to the invention alone or in combination (e.g. with PD-L1 inhibitors), respectively, for up to 120 hours. After compound exposure, tumor slices are fixed overnight using 4% paraformaldehyde.

2. Staining

Paraformaldehyde fixed slices are embedded in paraffin and processed to 5-µm sections. Hematoxylin & eosin (HE) staining is performed to assess histopathologic aspects and tumor cell proportion. Overall cell count, tumor cell count, and proliferation are analyzed by immunofluorescent staining. In brief, paraffin sections are deparaffinized. After antigen retrieval, sections are washed with 0.3% PBS/Triton™ X and blocked with 5% normal goat serum for 30 minutes. Primary antibodies against cytokeratins (AE1þ3), Ki67, and cleaved-PARP, respectively, are diluted in 0.5% bovine serum albumin and incubated at 4° C. overnight. Sections are rinsed with 0.3% phosphate buffered saline/Triton™ X and labeled with secondary antibodies. Nuclei are stained with Hoechst 33342. Additional stainings (e.g. for CEA expression) may be included.

3. Data Analysis

Five pictures (20×) per tissue slice are taken from fluorescent-stained sections using a fluorescent microscope. The positive pixel count is determined for Hoechst 33342, cytokeratin, Ki67, and cleaved-PARP stains with stain-specific segmentation algorithms. Proliferating/apoptotic tumor area is calculated by analyzing pixels of Ki67/cleaved PARP positive nuclei surrounded by cytokeratin-positive pixels. For every picture, the total cell count (Hoechst-positive), tumor cell count (Hoechst- and cytokeratin-positive), and proliferating tumor cell count (Hoechst-, cytokeratin-, and Ki67-positive/cleaved-PARP) is calculated. Tumor cell count is normalized to total cell count and proliferating tumor cell count is normalized to tumor cell count to consider different tumor cell fractions per picture. Mean slice values are then calculated from single image values. Mean values for conditions are calculated using mean slice values.

Example 13: In Vivo Anti-Tumor Activity

According to the knowledge of the inventors, anti-tumor activity of a bispecific antibody according to the invention can be evaluated as single agent as well as in combination treatment, respectively, in transgenic mice.

1. Cell Line Generation and Growth Testing

A hCEACAM5(Tg)hCD47(Tg)mCD47(ko) cell line, e.g. based on the murine colon cancer cell lines CT26 or MC38, will be generated. Knock-out (KO) of the endogenous mouse CD47 gene is performed by using CRISPR/Cas9 with subsequent isolation of KO clones by cell sorting. Transfection of the KO clones with a cassette driving the expression of both hCD47 and hCEACAM5 using an internal ribosome entry site (IRES) is performed followed by isolation of engineered clones based on e.g. overall expression levels and ratio. Three validated clones will be selected to subsequently test their engraftment/tumorigenicity in vivo for selection of the final clone.

2. In Vivo Anti-Tumor Activity

Mice strains of BALB/cJGpt background expressing human CD3e (T001550 heterozygous BALB/c-hCD3ET/Wt mice) and human CD47/human SIRPα (T037264 homozygous BALB/c-hCD47/hSIRPα mice) are available at GemPharmatech.

Alternatively, mice strains of C57BL/6/Bcgen background expressing human CD3e (homozygous B-hCD3E mice) and human CD47/human SIRPα (homozygous B-hSIRPα/hCD47 mice) are available at Biocytogen. The two mouse strains will be crossed to obtain triple humanized hCD3e/hSIRPα/hCD47 mice, and the offspring used for subsequent experiments to test a bispecific antibody according to the invention either as single agent or in combination treatment.

Triple humanized hCD3e/hSIRPα/hCD47 mice are inoculated with either CT26-hCEACAM5(Tg)hCD47(Tg)mCD47(ko) cell line (BALB/c background) or MC38-hCEACAM5(Tg)hCD47(Tg)mCD47(ko) cell line (C57BL/6 background) at day 0. Once medium tumor size in the cohort reaches e.g. 200 mm³, treatment with a bispecific antibody according to the invention as single agent as well as in combination is initiated as i.v. bolus at an interval of e.g. 2 treatments/week until one mouse shows a tumor volume of e.g. over 3000 mm³ or any one or more of the pre-specified animal protection and care endpoints occur. Tumor volume and body weight are measured three times per week. Tumor volume is given in mm³ using the following formula: TV=0.5a×b2, where a and b are the long and short diameters of the tumor, respectively.

All references cited herein are incorporated by reference to the same extent as if each individual publication, database entry, patent application or patent was specifically indicated to be incorporated by reference.

The invention claimed is:

1. A bispecific antibody molecule comprising a first binding part that binds specifically to human CEACAM5 and a second binding part that binds specifically to human CD47 wherein:
   a) the first binding part comprises a heavy chain variable region comprising CDRH1, CDRH2, and CDRH3, wherein CDRH1 is SEQ ID NO:1, CDRH2 is SEQ ID NO:2 and CDRH3 is SEQ ID NO:3,
   b) the first binding part comprises a light chain variable region comprising CDRL1, CDRL2, and CDRL3, wherein CDRL1, CDRL2, and CDRL3 are selected from the group consisting of
      b1) SEQ ID NO:14, SEQ ID NO:15, and SEQ ID NO:16, respectively;
      b2) SEQ ID NO:17, SEQ ID NO:18, and SEQ ID NO:19, respectively;
      b3) SEQ ID NO:20, SEQ ID NO:21, SEQ ID NO:22, respectively;
      b4) SEQ ID NO:23, SEQ ID NO:24, and SEQ ID NO:25, respectively; and
      b5) SEQ ID NO:26, SEQ ID NO:27, and SEQ ID NO:28, respectively; and
   c) the second binding part comprises a heavy chain variable region comprising CDRH1, CDRH2, and CDRH3, wherein CDRH1 is SEQ ID NO:1, CDRH2 is SEQ ID NO:2 and CDRH3 is SEQ ID NO:3,
   and a light chain variable region comprising CDRL1, CDRL2, and CDRL3, wherein CDRL1 is SEQ ID NO:7, CDRL2 is SEQ ID NO:8, and CDRL3 is SEQ ID NO:9.

2. The bispecific antibody molecule according to claim 1, comprising in the first binding part a variable heavy chain region comprising SEQ ID NO:4 and a variable light chain region selected from the group consisting of SEQ ID NO:32, SEQ ID NO:33, SEQ ID NO:34, SEQ ID NO:35, and SEQ ID NO:36, and comprising in the second binding part a variable heavy chain region comprising SEQ ID NO:4 and a variable light chain region comprising SEQ ID NO:10.

3. The bispecific antibody molecule according to claim 1, comprising in the first binding part a heavy chain comprising SEQ ID NO:5 and a light chain selected from the group consisting of SEQ ID NO:37, SEQ ID NO:38, SEQ ID NO:39, SEQ ID NO:40, and SEQ ID NO:41, and comprising in the second binding part a heavy chain region comprising SEQ ID NO:5 and a light chain comprising SEQ ID NO:11.

4. The bispecific antibody molecule according to claim 1, wherein the first and second binding parts comprise a common heavy chain, wherein the common heavy chain is SEQ ID NO:6.

5. The bispecific antibody molecule of claim 1, wherein said antibody is monovalent for the first binding part and monovalent for the second binding part.

6. The bispecific antibody molecule of claim 1, wherein the constant and variable framework region sequences are human.

7. The bispecific antibody molecule of claim 1, wherein the light chain of the first binding part is a lambda light chain (VLCL) and the light chain of the second binding part is a kappa light chain (VKCK).

8. The bispecific antibody molecule of claim 1 wherein the antibody is human IgG1 type.

9. The bispecific antibody molecule of claim 1, wherein said antibody comprises a Fc region that has been glycoengineered to have a reduced number of fucose residues as compared to the same bispecific antibody that has not been glycoengineered.

10. A pharmaceutical composition comprising a bispecific antibody molecule of claim 1 and a pharmaceutically acceptable excipient or pharmaceutically acceptable carrier.

* * * * *